(12) United States Patent
Scherzinger et al.

(10) Patent No.: US 10,655,113 B2
(45) Date of Patent: May 19, 2020

(54) METHODS OF GENERATING AND SCREENING FOR LYTIC CHIMERIC POLYPEPTIDES

(71) Applicant: HYPHARM GMBH, Bernried (DE)

(72) Inventors: Anna Scherzinger, Bernried (DE); Sonja Molinaro, Weilheim (DE); Bernd Buchberger, Zeitlarn/Laub (DE)

(73) Assignee: HYPHARM GMBH, Bernried (DE)

( * ) Notice: Subject to any disclaimer, the term of this patent is extended or adjusted under 35 U.S.C. 154(b) by 0 days.

(21) Appl. No.: 16/390,576

(22) Filed: Apr. 22, 2019

(65) Prior Publication Data

US 2019/0249156 A1 Aug. 15, 2019

Related U.S. Application Data

(62) Division of application No. 15/001,455, filed on Jan. 20, 2016, now Pat. No. 10,301,607, which is a division of application No. 13/704,759, filed as application No. PCT/EP2011/003022 on Jun. 17, 2011, now Pat. No. 9,249,447.

(30) Foreign Application Priority Data

Jun. 18, 2010 (EP) .................................... 10006360

(51) Int. Cl.
| | |
|---|---|
| *C12N 9/16* | (2006.01) |
| *C12N 9/36* | (2006.01) |
| *C12N 9/50* | (2006.01) |
| *C12N 9/80* | (2006.01) |
| *C12N 15/62* | (2006.01) |
| *C12Q 1/37* | (2006.01) |
| *G01N 33/68* | (2006.01) |
| *C12Q 1/18* | (2006.01) |
| *C40B 30/08* | (2006.01) |

(52) U.S. Cl.
CPC ............ *C12N 9/16* (2013.01); *C12N 9/2462* (2013.01); *C12N 9/50* (2013.01); *C12N 9/80* (2013.01); *C12N 15/62* (2013.01); *C12Q 1/18* (2013.01); *C12Q 1/37* (2013.01); *G01N 33/6845* (2013.01); *C07K 2319/00* (2013.01); *C12Y 301/00* (2013.01); *C12Y 302/01017* (2013.01); *C12Y 304/24* (2013.01); *C12Y 305/01028* (2013.01); *C40B 30/08* (2013.01); *G01N 2333/4722* (2013.01); *G01N 2333/952* (2013.01)

(58) Field of Classification Search
None
See application file for complete search history.

(56) References Cited

U.S. PATENT DOCUMENTS

| | | |
|---|---|---|
| 6,995,017 B1 | 2/2006 | Stemmer |
| 8,481,289 B2 | 7/2013 | Donovan et al. |

FOREIGN PATENT DOCUMENTS

| | | |
|---|---|---|
| WO | WO 2003/040342 | 5/2003 |
| WO | WO 2004/016811 | 2/2004 |
| WO | WO 2007/130655 | 11/2007 |
| WO | WO 2010/020657 | 2/2010 |

OTHER PUBLICATIONS

Baba et al., "Target cell specificity of a bacteriocin molecule: a C-terminal signal directs lysostaphin to the cell wall of *Staphylococcus aureus*," *EMBO Journal*, 15(18):4789-4797, 1996.
Becker et al., "Differentially conserved staphylococcal SH3b_5 cell wall binding domains confer increased staphylolytic and streptolytic activity to a streptococcal prophage endolysin domain," *Gene*, 443(1-2):32-41, 2009.
Briers et al., "The high-affinity peptidoglycan binding domain of *Pseudomonas* phage endolysin KZ144," *Biochemical and Biophysical Research Communications*, 383(2):187-191, 2009.
Donovan et al., "Peptidoglycan hydrolase fusions maintain their parental specificities," *Applied and Environmental Microbiology*, 72(4):2988-2996, 2006.
Kitamura et al., "Construction of block-shuffled libraries of DNA for evolutionary protein engineering: Y-ligation-based block shuffling," *Protein Engineering*, 15(10):843-853, 2002.
Loessner et al., "C-terminal domains of *Listeria monocytogenes* bacteriophage murein hydrolases determine specific recognition and high-affinity binding to bacterial cell wall carbohydrates," *Molecular Microbiology*, 44(2):335-349, 2002.
Office Communication issued in European Patent Application No. 11726355.8, dated Apr. 15, 2014.
Office Communication issued in European Patent Application No. 11726355.8, dated Mar. 3, 2015.
Office Communication issued in U.S. Appl. No. 13/704,759, dated Jun. 16, 2015.
Office Communication issued in U.S. Appl. No. 15/001,455, dated Jan. 10, 2019.
Office Communication issued in U.S. Appl. No. 15/001,455, dated Aug. 24, 2018.
Office Communication issued in U.S. Appl. No. 15/001,455, dated Apr. 12, 2018.

(Continued)

*Primary Examiner* — Suzanne M Noakes
*Assistant Examiner* — Jae W Lee
(74) *Attorney, Agent, or Firm* — Parker Highlander PLLC

(57) ABSTRACT

The present invention relates to novel methods of generating and screening for chimeric polypeptides, which can be used in the treatment and prophylaxis of pathogenic bacterial contamination, colonisation and infection. The novel methods are based on random recombination of protein domains, and the chimeric polypeptides obtainable by the methods according to the invention are characterized in that they comprise at least one enzymatic active domain (EAD) and at least one cell binding domain (CBD). The present invention also relates to a library of chimeric polypeptides obtainable by the methods of the present invention.

11 Claims, 11 Drawing Sheets

Specification includes a Sequence Listing.

(56) References Cited

OTHER PUBLICATIONS

Padgett et al., "Creating seamless junctions independent of restriction sites in PCR cloning," *Gene*, 168(1):31-35, 1996.
PCT International Search Report and Written Opinion issued in International Patent Application No. PCT/EP2011/003022, dated Jul. 19, 2011.
Response to Office Communication dated Apr. 15, 2014 submitted in European Patent Application No. 11726355.8, dated Oct. 21, 2014.
Soderlind et al., "Domain libraries: synthetic diversity for de novo design of antibody V-regions," *Gene*, 160(2):269-272, 1995.
Tominaga et al., "Development of innovative pediocin PA-1 by DNA shuffling among class IIa bacteriocins," *Applied and Environmental Microbiology*, 73(16):5292-5299, 2007.
Villiers et al., "USER friendly DNA recombination (USERec): a simple and flexible near homology-independent method for gene library construction," *Protein Engineering Design and Selection*, 23(1):1-8, 2010.
Yamabhai, "Sticky PCR: a PCR-based protocol for targeted protein engineering," *Biotechnology Journal*, 4(4):544-553, 2009.

| EAD | CBD |
|---|---|
| EAD511 | CBD006 |
| EAD511 | CBD500 |
| EAD511 | CBD511 |
| EAD511 | CBDP40 |
| EADP35 | CBD006 |
| EADP35 | CBD500 |
| EADP35 | CBD511 |
| EADP35 | CBDP40 |
| EADP40 | CBD006 |
| EADP40 | CBD500 |
| EADP40 | CBD511 |
| EADP40 | CBDP40 |
| EADPSA | CBD006 |
| EADPSA | CBD500 |
| EADPSA | CBD511 |
| EADPSA | CBDP40 |

|   | EAD    | CBD    | kDa |
|---|--------|--------|-----|
| A | EADP40 | CBD511 | 43  |
| B | EADP40 | CBD500 | 44  |
| C | EADP40 | CBDP40 | 40  |
| I | EADP40 | CBD006 | 36  |
| D | EAD511 | CBD511 | 39  |
| E | EAD511 | CBD500 | 40  |
| H | EAD511 | CBDP40 | 36  |
| M | EAD511 | CBD006 | 32  |
| F | EADPSA | CBD511 | 37  |
| G | EADPSA | CBD500 | 39  |
| J | EADPSA | CBDP40 | 35  |
| O | EADPSA | CBD006 | 30  |
| K | EADP35 | CBD511 | 34  |
| L | EADP35 | CBD500 | 36  |
| N | EADP35 | CBDP40 | 32  |
| P | EADP35 | CBD006 | 27  |

|   | EAD | CBD | sv 6a | sv 1/2a | sv 4b |
|---|---|---|---|---|---|
| A | EADP40 | CBD511 | ++ | ++ | ++ |
| B | EADP40 | CBD500 | ++ |  | ++ |
| C | EADP40 | CBDP40 |  |  |  |
| D | EAD511 | CBD511 | ++ | ++ | ++ |
| E | EAD511 | CBD500 | ++ |  | ++ |
| F | EADPSA | CBD511 | (+) | + | + |
| G | EADPSA | CBD500 | (+) |  | (+) |
| H | EAD511 | CBDP40 |  |  |  |
| I | EADP40 | CBD006 |  | + | (+) |
| J | EADPSA | CBDP40 |  |  |  |
| K | EADP35 | CBD511 | (+) | + | + |
| L | EADP35 | CBD500 | (+) |  | + |
| M | EAD511 | CBD006 |  | + |  |
| N | EADP35 | CBDP40 |  |  |  |
| O | EADPSA | CBD006 |  | + |  |
| P | EADP35 | CBD006 |  | (+) |  |

Expected binding spectrum
CBD500: sv 4,5,6
CBD511: all
CBD006: sv 1/2, 3, 7
CBDP40: nearly all, (not this 6a)

FIG. 12

SEQUENCE LISTING

<160> NUMBER OF SEQ ID NOS: 23

<210> SEQ ID NO 1
<211> LENGTH: 341
<212> TYPE: PRT
<213> ORGANISM: Bacteriophage A511

<400> SEQUENCE: 1

| | | | | | | | | | | | | | | |
|---|---|---|---|---|---|---|---|---|---|---|---|---|---|---|
| Met | Val | Lys | Tyr | Thr | Val | Glu | Asn | Lys | Ile | Ile | Ala | Gly | Leu | Pro | Lys |
| 1 | | | | 5 | | | | | 10 | | | | | 15 | |

| Gly | Lys | Leu | Lys | Gly | Ala | Asn | Phe | Val | Ile | Ala | His | Glu | Thr | Ala | Asn |
|---|---|---|---|---|---|---|---|---|---|---|---|---|---|---|---|
| | | | 20 | | | | | 25 | | | | | 30 | | |

| Ser | Lys | Ser | Thr | Ile | Asp | Asn | Glu | Val | Ser | Tyr | Met | Thr | Arg | Asn | Trp |
|---|---|---|---|---|---|---|---|---|---|---|---|---|---|---|---|
| | | | 35 | | | | | 40 | | | | | 45 | | |

| Lys | Asn | Ala | Phe | Val | Thr | His | Phe | Val | Gly | Gly | Gly | Arg | Val | Val |
|---|---|---|---|---|---|---|---|---|---|---|---|---|---|---|
| | 50 | | | | | 55 | | | | | 60 | | | |

| Gln | Val | Ala | Asn | Val | Asn | Tyr | Val | Ser | Trp | Gly | Ala | Gly | Gln | Tyr | Ala |
|---|---|---|---|---|---|---|---|---|---|---|---|---|---|---|---|
| 65 | | | | | 70 | | | | | 75 | | | | | 80 |

| Asn | Ser | Tyr | Ser | Tyr | Ala | Gln | Val | Glu | Leu | Cys | Arg | Thr | Ser | Asn | Ala |
|---|---|---|---|---|---|---|---|---|---|---|---|---|---|---|---|
| | | | | 85 | | | | | 90 | | | | | 95 | |

| Thr | Thr | Phe | Lys | Lys | Asp | Tyr | Glu | Val | Tyr | Cys | Gln | Leu | Leu | Val | Asp |
|---|---|---|---|---|---|---|---|---|---|---|---|---|---|---|---|
| | | | | 100 | | | | | 105 | | | | | 110 | |

| Leu | Ala | Lys | Lys | Ala | Gly | Ile | Pro | Ile | Thr | Leu | Asp | Ser | Gly | Ser | Lys |
|---|---|---|---|---|---|---|---|---|---|---|---|---|---|---|---|
| | | | 115 | | | | | 120 | | | | | 125 | | |

| Thr | Ser | Asp | Lys | Gly | Ile | Lys | Ser | His | Lys | Trp | Val | Ala | Asp | Lys | Leu |
|---|---|---|---|---|---|---|---|---|---|---|---|---|---|---|---|
| 130 | | | | | 135 | | | | | 140 | | | | | |

| Gly | Gly | Thr | Thr | His | Gln | Asp | Pro | Tyr | Ala | Tyr | Leu | Ser | Ser | Trp | Gly |
|---|---|---|---|---|---|---|---|---|---|---|---|---|---|---|---|
| 145 | | | | | 150 | | | | | 155 | | | | | 160 |

| Ile | Ser | Lys | Ala | Gln | Phe | Ala | Ser | Asp | Leu | Ala | Lys | Val | Ser | Gly | Gly |
|---|---|---|---|---|---|---|---|---|---|---|---|---|---|---|---|
| | | | | 165 | | | | | 170 | | | | | 175 | |

| Gly | Asn | Thr | Gly | Thr | Ala | Pro | Ala | Lys | Pro | Ser | Thr | Pro | Ala | Pro | Lys |
|---|---|---|---|---|---|---|---|---|---|---|---|---|---|---|---|
| | | | 180 | | | | | 185 | | | | | 190 | | |

| Pro | Ser | Thr | Pro | Ser | Thr | Asn | Leu | Asp | Lys | Leu | Gly | Leu | Val | Asp | Tyr |
|---|---|---|---|---|---|---|---|---|---|---|---|---|---|---|---|
| | | 195 | | | | | 200 | | | | | 205 | | | |

| Met | Asn | Ala | Lys | Lys | Met | Asp | Ser | Ser | Tyr | Ser | Asn | Arg | Asp | Lys | Leu |
|---|---|---|---|---|---|---|---|---|---|---|---|---|---|---|---|
| 210 | | | | | 215 | | | | | 220 | | | | | |

| Ala | Lys | Gln | Tyr | Gly | Ile | Ala | Asn | Tyr | Ser | Gly | Thr | Ala | Ser | Gln | Asn |
|---|---|---|---|---|---|---|---|---|---|---|---|---|---|---|---|
| 225 | | | | | 230 | | | | | 235 | | | | | 240 |

| Thr | Thr | Leu | Leu | Ser | Lys | Ile | Lys | Gly | Gly | Ala | Pro | Lys | Pro | Ser | Thr |
|---|---|---|---|---|---|---|---|---|---|---|---|---|---|---|---|
| | | | | 245 | | | | | 250 | | | | | 255 | |

| Pro | Ala | Pro | Lys | Pro | Ser | Thr | Ser | Thr | Ala | Lys | Lys | Ile | Tyr | Phe | Pro |
|---|---|---|---|---|---|---|---|---|---|---|---|---|---|---|---|
| | | | 260 | | | | | 265 | | | | | 270 | | |

| Pro | Asn | Lys | Gly | Asn | Trp | Ser | Val | Tyr | Pro | Thr | Asn | Lys | Ala | Pro | Val |
|---|---|---|---|---|---|---|---|---|---|---|---|---|---|---|---|
| | 275 | | | | | 280 | | | | | 285 | | | | |

| Lys | Ala | Asn | Ala | Ile | Gly | Ala | Ile | Asn | Pro | Thr | Lys | Phe | Gly | Gly | Leu |
|---|---|---|---|---|---|---|---|---|---|---|---|---|---|---|---|
| | 290 | | | | | 295 | | | | | 300 | | | | |

| Thr | Tyr | Thr | Ile | Gln | Lys | Asp | Arg | Gly | Asn | Gly | Val | Tyr | Glu | Ile | Gln |
|---|---|---|---|---|---|---|---|---|---|---|---|---|---|---|---|
| 305 | | | | | 310 | | | | | 315 | | | | | 320 |

| Thr | Asp | Gln | Phe | Gly | Arg | Val | Gln | Val | Tyr | Gly | Ala | Pro | Ser | Thr | Gly |
|---|---|---|---|---|---|---|---|---|---|---|---|---|---|---|---|
| | | | | 325 | | | | | 330 | | | | | 335 | |

| Ala | Val | Ile | Lys | Lys |
|---|---|---|---|---|
| | | | 340 | |

<210> SEQ ID NO 2
<211> LENGTH: 289

```
<212> TYPE: PRT
<213> ORGANISM: Bacteriophage A500

<400> SEQUENCE: 2

Met Ala Leu Thr Glu Ala Trp Leu Ile Glu Lys Ala Asn Arg Lys Leu
1               5                   10                  15

Asn Ala Gly Gly Met Tyr Lys Ile Thr Ser Asp Lys Thr Arg Asn Val
            20                  25                  30

Ile Lys Lys Met Ala Lys Glu Gly Ile Tyr Leu Cys Val Ala Gln Gly
        35                  40                  45

Tyr Arg Ser Thr Ala Glu Gln Asn Ala Leu Tyr Ala Gln Gly Arg Thr
    50                  55                  60

Lys Pro Gly Ala Ile Val Thr Asn Ala Lys Gly Gln Ser Asn His
65                  70                  75                  80

Asn Tyr Gly Val Ala Val Asp Leu Cys Leu Tyr Thr Asn Asp Gly Lys
                85                  90                  95

Asp Val Ile Trp Glu Ser Thr Thr Ser Arg Trp Lys Lys Val Val Ala
            100                 105                 110

Ala Met Lys Ala Glu Gly Phe Lys Trp Gly Gly Asp Trp Lys Ser Phe
        115                 120                 125

Lys Asp Tyr Pro His Phe Glu Leu Cys Asp Ala Val Ser Gly Glu Lys
    130                 135                 140

Ile Pro Ala Ala Thr Gln Asn Thr Asn Thr Asn Ser Asn Arg Tyr Glu
145                 150                 155                 160

Gly Lys Val Ile Asp Ser Ala Pro Leu Leu Pro Lys Met Asp Phe Lys
                165                 170                 175

Ser Ser Pro Phe Arg Met Tyr Lys Val Gly Thr Glu Phe Leu Val Tyr
            180                 185                 190

Asp His Asn Gln Tyr Trp Tyr Lys Thr Tyr Ile Asp Asp Lys Leu Tyr
        195                 200                 205

Tyr Met Tyr Lys Ser Phe Cys Asp Val Val Ala Lys Lys Asp Ala Lys
    210                 215                 220

Gly Arg Ile Lys Val Arg Ile Lys Ser Ala Lys Asp Leu Arg Ile Pro
225                 230                 235                 240

Val Trp Asn Asn Ile Lys Leu Asn Ser Gly Lys Ile Lys Trp Tyr Ala
                245                 250                 255

Pro Asn Val Lys Leu Ala Trp Tyr Asn Tyr Arg Arg Gly Tyr Leu Glu
            260                 265                 270

Leu Trp Tyr Pro Asn Asp Gly Trp Tyr Tyr Thr Ala Glu Tyr Phe Leu
        275                 280                 285

Lys

<210> SEQ ID NO 3
<211> LENGTH: 344
<212> TYPE: PRT
<213> ORGANISM: Bacteriophage P40

<400> SEQUENCE: 3

Met Val Leu Val Leu Asp Ile Ser Lys Trp Gln Pro Thr Val Asn Tyr
1               5                   10                  15

Ser Gly Leu Lys Glu Asp Val Gly Phe Val Val Ile Arg Ser Ser Asn
            20                  25                  30

Gly Thr Gln Lys Tyr Asp Glu Arg Leu Glu Gln His Ala Lys Gly Leu
        35                  40                  45

Asp Lys Val Gly Met Pro Phe Gly Leu Tyr His Tyr Ala Leu Phe Glu
```

```
            50                  55                  60
Gly Gly Gln Asp Thr Ile Asn Glu Ala Asn Met Leu Val Ser Ala Tyr
 65                  70                  75                  80

Lys Lys Cys Arg Gln Leu Gly Ala Glu Pro Thr Phe Leu Phe Leu Asp
                 85                  90                  95

Tyr Glu Glu Val Lys Leu Lys Ser Gly Asn Val Val Asn Glu Cys Gln
                100                 105                 110

Arg Phe Ile Asp His Val Lys Gly Gln Thr Gly Val Lys Val Gly Leu
            115                 120                 125

Tyr Ala Gly Asp Ser Phe Trp Lys Thr His Asp Leu Asp Lys Val Lys
            130                 135                 140

His Asp Leu Arg Trp Val Ala Arg Tyr Gly Val Asp Asn Gly Lys Pro
145                 150                 155                 160

Ser Thr Lys Pro Ser Ile Pro Tyr Asp Leu Trp Gln Tyr Thr Ser Lys
                165                 170                 175

Gly Arg Ile Lys Ala Ile Ala Ser Pro Val Asp Met Asn Thr Cys Ser
                180                 185                 190

Ser Asp Ile Leu Asn Lys Leu Lys Gly Ser Lys Ala Pro Val Lys Pro
            195                 200                 205

Ala Pro Lys Pro Thr Pro Ser Lys Pro Ala Pro Ala Lys Pro Ala Pro
210                 215                 220

Lys Thr Thr Thr Lys Tyr Val Asn Thr Ala His Leu Asn Ile Arg Glu
225                 230                 235                 240

Lys Ala Ser Ala Asp Ser Lys Val Leu Gly Val Leu Asp Leu Asn Asp
                245                 250                 255

Ser Val Gln Val Ile Ser Glu Ser Gly Gly Trp Ser Lys Leu Lys Ser
                260                 265                 270

Gly Asn Lys Gln Val Tyr Val Ser Ser Lys Tyr Leu Ser Lys Ser Lys
            275                 280                 285

Thr Thr Pro Lys Ala Lys Pro Ser Ser Lys Gln Tyr Tyr Thr Ile Lys
            290                 295                 300

Ser Gly Asp Asn Leu Ser Tyr Ile Ala Lys Lys Tyr Lys Thr Val
305                 310                 315                 320

Lys Gln Ile Gln Asn Trp Asn Gly Ile Lys Asp Ala Asn Lys Ile Tyr
                325                 330                 335

Ala Gly Gln Lys Ile Arg Val Lys
            340

<210> SEQ ID NO 4
<211> LENGTH: 291
<212> TYPE: PRT
<213> ORGANISM: Bacteriophage P35

<400> SEQUENCE: 4

Met Ala Arg Lys Phe Thr Lys Ala Glu Leu Val Ala Lys Ala Glu Lys
 1                5                  10                  15

Lys Val Gly Gly Leu Lys Pro Asp Val Lys Ala Val Leu Ser Ala
                 20                  25                  30

Val Lys Glu Ala Tyr Asp Arg Tyr Gly Ile Gly Ile Ile Val Ser Gln
             35                  40                  45

Gly Tyr Arg Ser Ile Ala Glu Gln Asn Gly Leu Tyr Ala Gln Gly Arg
         50                  55                  60

Thr Lys Pro Gly Asn Ile Val Thr Asn Ala Lys Gly Gly Gln Ser Asn
 65                  70                  75                  80
```

His Asn Phe Gly Val Ala Val Asp Phe Ala Ile Asp Leu Ile Asp Asp
                85                  90                  95

Gly Lys Ile Asp Ser Trp Gln Pro Ser Ala Thr Ile Val Asn Met Met
            100                 105                 110

Lys Arg Arg Gly Phe Lys Trp Gly Asp Trp Lys Ser Phe Thr Asp
        115                 120                 125

Leu Pro His Phe Glu Ala Cys Asp Trp Tyr Arg Gly Glu Arg Lys Tyr
    130                 135                 140

Lys Val Asp Thr Ser Glu Trp Lys Lys Lys Glu Asn Ile Asn Ile Val
145                 150                 155                 160

Ile Lys Asp Val Gly Tyr Phe Gln Asp Lys Pro Gln Phe Leu Asn Ser
                165                 170                 175

Lys Ser Val Arg Gln Trp Lys His Gly Thr Lys Val Lys Leu Thr Lys
            180                 185                 190

His Asn Ser His Trp Tyr Thr Gly Val Val Lys Asp Gly Asn Lys Ser
        195                 200                 205

Val Arg Gly Tyr Ile Tyr His Ser Met Ala Lys Val Thr Ser Lys Asn
    210                 215                 220

Ser Asp Gly Ser Val Asn Ala Thr Ile Asn Ala His Ala Phe Cys Trp
225                 230                 235                 240

Asp Asn Lys Lys Leu Asn Gly Gly Asp Phe Ile Asn Leu Lys Arg Gly
                245                 250                 255

Phe Lys Gly Ile Thr His Pro Ala Ser Asp Gly Phe Tyr Pro Leu Tyr
            260                 265                 270

Phe Ala Ser Arg Lys Lys Thr Phe Tyr Ile Pro Arg Tyr Met Phe Asp
        275                 280                 285

Ile Lys Lys
    290

<210> SEQ ID NO 5
<211> LENGTH: 321
<212> TYPE: PRT
<213> ORGANISM: Bacteriophage B054

<400> SEQUENCE: 5

Met Ala Lys Lys Leu Lys Leu Ala Ile Tyr Ala Gly His Gly Gly Val
1               5                   10                  15

Asp Ser Gly Ala Thr Gly Glu Gly Tyr Arg Glu Asp Asp Leu Thr Leu
            20                  25                  30

Asp Ile Ala Lys Arg Thr Thr Lys Val Leu Arg Gly Ala Gly His Thr
        35                  40                  45

Val Ile Asn Asn Arg Thr Thr Asp Val Asn Arg Asn Ile Ser Ala Asp
    50                  55                  60

Ala Lys Leu Ala Asn Arg Glu Lys Val Asp Ala Val Ile Glu Phe His
65                  70                  75                  80

Phe Asp Ala Ala Gly Ala Ser Ala Glu Gly Thr Thr Gly Phe Tyr Cys
                85                  90                  95

Glu Gly Ser Ser Ser Lys Lys Leu Ala Gln Cys Val Asn Asp Lys
            100                 105                 110

Leu Asp Asp Val Phe Lys Asp Arg Asn Val Lys Pro Asp Thr Ser Thr
        115                 120                 125

Arg His Gly Arg Leu Gly Ile Leu Arg Glu Thr Asn Ala Val Ala Thr
    130                 135                 140

Leu Gln Glu Val Ala Phe Ile Thr Asn Lys Asn Asp Met Ile Lys Tyr
145                 150                 155                 160

```
Asn Gln Arg Ala Asp Glu Ile Ala Lys Lys Ala Ala Glu Gly Ile Leu
                165                 170                 175

Ser Tyr Phe Asn Glu Lys Leu Pro Glu Gln Asn Pro Asn Arg His Asp
            180                 185                 190

Gly Ala Val Val Asp Ser Ile Pro Ala Leu Pro Lys Pro Asp Phe Lys
        195                 200                 205

Thr Val Pro Ser Lys Met Tyr Lys Ala Gly Ser Glu Leu Leu Val Tyr
    210                 215                 220

Asp His Asn Lys Tyr Trp Tyr Lys Thr Tyr Ile Asn Asp Lys Leu Cys
225                 230                 235                 240

Tyr Ile Tyr Lys Ser Phe Cys Ile Ser Asn Gly Lys Lys Asp Ser Lys
                245                 250                 255

Gly Arg Ile Pro Ile Lys Ile Lys Ser Val Lys Asp Leu Arg Ile Pro
            260                 265                 270

Val Trp Asp Asn Thr Lys Leu Ser Ser Gly Lys Ile Lys Trp Tyr Ala
        275                 280                 285

Pro Asn Thr Lys Leu Ser Trp Tyr Asn Asn Lys Lys Gly Tyr Leu Glu
    290                 295                 300

Leu Tyr Tyr Pro Asn Gln Gly Trp Tyr Tyr Thr Ala Asn Tyr Phe Leu
305                 310                 315                 320

Lys

<210> SEQ ID NO 6
<211> LENGTH: 314
<212> TYPE: PRT
<213> ORGANISM: Bacteriophage PSA

<400> SEQUENCE: 6

Met Ser Asn Tyr Ser Met Ser Arg Gly His Ser Asp Lys Cys Val Gly
1               5                   10                  15

Ala Glu Asp Ile Leu Ser Glu Ile Lys Glu Ala Glu Lys Val Leu Asn
            20                  25                  30

Ala Ala Ser Asp Glu Leu Lys Arg Glu Gly His Asn Val Lys Thr Phe
        35                  40                  45

Ile Asp Arg Thr Ser Thr Thr Gln Ser Ala Asn Leu Asn Lys Ile Val
    50                  55                  60

Asn Trp His Asn Ala Asn Pro Ala Asp Val His Ile Ser Val His Leu
65                  70                  75                  80

Asn Ala Gly Lys Gly Thr Gly Val Glu Val Trp Tyr Tyr Ala Gly Asp
                85                  90                  95

Glu Lys Gly Arg Lys Leu Ala Val Glu Ile Ser Ala Lys Met Ala Lys
            100                 105                 110

Ala Leu Gly Leu Pro Asn Arg Gly Ala Lys Ala Thr Lys Asp Leu Arg
        115                 120                 125

Phe Leu Asn Ser Thr Lys Gly Thr Ala Val Leu Leu Glu Val Cys Phe
    130                 135                 140

Val Asp Arg Lys Glu Asp Ala Asn Ala Ile His Lys Ser Gly Met Tyr
145                 150                 155                 160

Asp Lys Leu Gly Ile Ala Ile Ala Glu Gly Leu Thr Gly Lys Thr Val
                165                 170                 175

Ala Ala Lys Asn Pro Asn Arg His Ser Gly Ala Val Val Asp Ser Val
            180                 185                 190

Pro Met Leu Ser Lys Met Asp Phe Lys Ser Ser Pro Ile Lys Met Tyr
        195                 200                 205
```

```
Lys Ala Gly Ser Ser Leu Leu Val Tyr Glu His Asn Lys Tyr Trp Tyr
        210                 215                 220

Lys Ala Tyr Ile Asn Asp Lys Leu Cys Tyr Ile Tyr Lys Ser Phe Cys
225                 230                 235                 240

Ile Ser Asn Gly Lys Lys Asp Ala Lys Gly Arg Ile Lys Val Arg Ile
                245                 250                 255

Lys Ser Ala Lys Asp Leu Arg Ile Pro Val Trp Asn Asn Thr Lys Leu
            260                 265                 270

Asn Ser Gly Lys Ile Lys Trp Tyr Ser Pro Gly Thr Lys Leu Ser Trp
        275                 280                 285

Tyr Asp Asn Lys Lys Gly Tyr Leu Glu Leu Trp Tyr Glu Lys Asp Gly
290                 295                 300

Trp Tyr Tyr Thr Ala Asn Tyr Phe Leu Lys
305                 310
```

<210> SEQ ID NO 7
<211> LENGTH: 235
<212> TYPE: PRT
<213> ORGANISM: Bacteriophage A006

<400> SEQUENCE: 7

```
Met Ala Leu Thr Glu Ala Trp Leu Ile Glu Lys Ala Asn Arg Lys Leu
1               5                   10                  15

Asn Val Ser Gly Met Asn Lys Ser Val Ala Asp Lys Thr Arg Asn Val
            20                  25                  30

Ile Lys Lys Met Ala Lys Lys Gly Ile Tyr Leu Cys Val Ala Gln Gly
        35                  40                  45

Tyr Arg Ser Ser Ala Glu Gln Asn Ala Leu Tyr Ala Gln Gly Arg Thr
    50                  55                  60

Lys Pro Gly Ala Val Val Thr Asn Ala Lys Gly Gln Ser Asn His
65                  70                  75                  80

Asn Tyr Gly Val Ala Val Asp Leu Cys Leu Tyr Thr Ser Asp Gly Lys
                85                  90                  95

Asn Val Ile Trp Glu Ser Thr Thr Ser Arg Trp Lys Thr Val Val Ser
            100                 105                 110

Ala Met Lys Ala Glu Gly Phe Glu Trp Gly Gly Asp Trp Lys Ser Phe
        115                 120                 125

Lys Asp Tyr Pro His Phe Glu Leu Tyr Asp Ala Ala Gly Gly Glu Lys
    130                 135                 140

Ala Pro Ser Thr Ser Ala Ser Lys Pro Ala Thr Ser Thr Ser Ser Asn
145                 150                 155                 160

Lys Asn Val Tyr Tyr Thr Glu Asn Pro Arg Lys Val Lys Thr Leu Val
                165                 170                 175

Gln Cys Asp Leu Tyr Asn Ser Val Asp Phe Thr Glu Lys His Lys Thr
            180                 185                 190

Gly Gly Thr Tyr Pro Ala Gly Thr Val Phe Thr Ile Ser Gly Met Gly
        195                 200                 205

Lys Thr Lys Gly Gly Thr Pro Arg Leu Lys Thr Lys Ser Gly Tyr Tyr
    210                 215                 220

Leu Thr Ala Asn Lys Lys Phe Val Lys Lys Ile
225                 230                 235
```

<210> SEQ ID NO 8
<211> LENGTH: 276
<212> TYPE: PRT

<213> ORGANISM: Bacteriophage B025

<400> SEQUENCE: 8

```
Met Thr Met Tyr Tyr Glu Glu Arg Ser Arg Asn Asn Ile Ala Lys Leu
1               5                   10                  15

Ala Ala Asn Thr Arg Ala Lys Ala Leu Glu Trp Phe Asn Trp Cys Cys
            20                  25                  30

Lys Asn Gly Ile Glu Val Leu Val Tyr Glu Thr Ile Arg Thr Lys Glu
        35                  40                  45

Gln Gln Ala Ala Asn Val Ala Asn Gly Lys Ser Gln Thr Met Arg Ser
    50                  55                  60

Tyr His Ile Val Gly Gln Ala Phe Asp Phe Val Met Ala Lys Gly Lys
65                  70                  75                  80

Thr Val Asp Trp Gly Gly Tyr Lys Thr Ala Lys Ala Lys Lys Val Ile
                85                  90                  95

Ala Lys Ala Lys Ala Leu Gly Phe Ser Trp Gly Gly Asp Trp Ser Gly
            100                 105                 110

Phe Val Asp Cys Pro His Met Gln Tyr Glu Tyr Lys Gly Tyr Gly Thr
        115                 120                 125

Asp Lys Phe Thr Ala Asp Lys Leu Val Ala Asn Asn Lys Thr Gly Lys
    130                 135                 140

Gln Gly Val Tyr Ala Arg Asp Phe Leu Asn Ile Arg Thr Lys Ala Thr
145                 150                 155                 160

Trp Asp Ser Pro Val Ala Phe Lys Val Pro Ile Tyr Tyr Ala Gln
                165                 170                 175

Ile Leu Trp Asp Thr Lys Asn Gly Asp Trp Val Gln Ile Glu Phe Gln
            180                 185                 190

Gly Lys Lys Gly Trp Tyr Lys Pro Ser Phe Lys Glu Tyr Trp Tyr Glu
        195                 200                 205

Lys Asp Pro Cys Thr Ser Tyr Ile Cys Val Ala Asp Val Asn Phe Arg
    210                 215                 220

Lys Ser Ser Lys Trp Asp Ser Pro Val Ala Gln Lys Lys Lys Gly
225                 230                 235                 240

Glu Thr Val Arg Met Val Lys Lys Ala Lys Asn Gly Trp Leu Glu Phe
                245                 250                 255

Gly Leu Thr Asn Gly Val Ile Gly Tyr Ile Pro Asn Ser Ala Lys Tyr
            260                 265                 270

Val Lys Lys Lys
        275
```

<210> SEQ ID NO 9
<211> LENGTH: 795
<212> TYPE: PRT
<213> ORGANISM: Bacteriophage P100

<400> SEQUENCE: 9

```
Met Thr Thr Val Lys Arg Met Pro Glu Phe Asp Leu Lys Phe Val Thr
1               5                   10                  15

Glu Lys Asn Asp Tyr Leu Ile Arg Tyr Asp Ala Arg Asn Pro Ser Ser
            20                  25                  30

Asp Thr Leu Ala Glu Lys Val Ile Ser Val Thr Thr Lys Asn Ala Met
        35                  40                  45

Ser Asp Asp Ser Ala Val Phe Ser Ile Val Ala Gly Asp Met Glu
    50                  55                  60

Trp Asp Lys Ile Leu Asp Ser Asn Asp Val Val Ile Leu Lys Ile Tyr
```

```
                65                  70                  75                  80
Pro Asn Leu Arg Val Met Met Pro Asp Asn Val Val Leu Val Gly
                    85                  90                  95

Leu Ile Ser Glu Val Arg Arg Glu Gly Asp Tyr Ser Asn Asn Ser Ile
                100                 105                 110

Ile Tyr Arg Ile Thr Gly Gln Ser Phe Ala Lys Ser Phe Met Gln Phe
                115                 120                 125

Gln Leu Gly Val Ile Gln Glu Val Ser Val Ile Thr Asp Ile Gly
                130                 135                 140

Trp Leu Pro Asp Ser Lys Ala Asp Gly Val Glu Phe Thr Gly Lys Thr
145                 150                 155                 160

Ala Ala Glu Ile Gly Lys Ser Ile Thr Asp Arg Phe Lys Lys Tyr Met
                165                 170                 175

Lys Tyr Asn Phe Asn Arg Glu Tyr Thr Met Glu Asn Phe Leu Asp Tyr
                180                 185                 190

Ser Phe Ser Ser Trp Lys Asp Tyr Glu Lys Leu Ala Asp Pro Thr Pro
                195                 200                 205

Phe Ile Asn Tyr Glu Gly Ser Leu Lys Gln Leu Leu Asp Asp Val Thr
                210                 215                 220

Ala Lys Pro Phe Asn Glu Leu Phe Phe Glu Ser Thr Ser Asp Glu Lys
225                 230                 235                 240

Cys Lys Met Ile Met Arg Arg Thr Pro Phe Asn Lys Glu Asp Trp Asp
                245                 250                 255

Lys Leu Pro Ser Tyr Lys Ile Ser Thr Glu Ala Val Ile Ser Asp Ser
                260                 265                 270

Leu Ala Lys Gly Asp Thr Glu Ala Tyr Ser Ile Phe Asn Val Thr Ser
                275                 280                 285

Gly Asn Met Ala Gly Ala Thr Ser Val Asp Leu Asn Ser Phe Pro Gln
                290                 295                 300

Tyr His Gln Ala Leu Val Asp Lys Tyr Gly Tyr Lys Lys Leu Glu Val
305                 310                 315                 320

Asp Asn Arg Tyr Leu Phe Glu Ser Ser Thr Asp Gly Ser Ser Thr Thr
                325                 330                 335

Glu Lys Ala Asp Val Gly Ser Lys Glu Lys Thr Lys Thr Val Ile Thr
                340                 345                 350

Tyr Ser Lys Phe Asn Ser Phe Met Arg Ser Tyr Thr Ser Asp Gln Val
                355                 360                 365

Arg Met Asn Gln Ser Ser Ile Ala Lys Ser Leu Val Asp Ser Tyr Asp
                370                 375                 380

Lys Leu Thr Thr Ser Gln Ala Asn Gln Leu Leu Ala Lys Tyr Ser Ala
385                 390                 395                 400

Val Gly Ala Ile Ser Glu Ala Asp Phe Lys Lys Ile Val Gly Asp Ile
                405                 410                 415

Ala Glu Gly Asp Asn Thr Gly Thr Ala Thr Leu Asp Phe Asp Ser Val
                420                 425                 430

Asn Ser Trp Phe Ser Leu Asn Tyr Ser Ser Leu Ser Glu Val Ser Thr
                435                 440                 445

Asn Arg Asp Ala Thr Ile Lys Ala Phe Val Lys Asn Phe Ala Asn Thr
                450                 455                 460

Asp Glu Asp Gln Ala Thr Lys Ile Val Ala Leu Tyr Ile Ser Ser Gln
465                 470                 475                 480

Gly Val Met Thr Lys Glu Lys Phe Asp Ala Ile Ile Lys Glu Ser Thr
                485                 490                 495
```

-continued

Ser Ser Ser Thr Lys Asp Pro Asp Asn Thr Thr Gly Asn Ser Ser Ser
                500                 505                 510

Ala Leu Gln Tyr Phe Ser Lys Thr Ile Tyr Asn Trp Tyr Ser Glu Asn
            515                 520                 525

Ala Asn Phe Tyr Ala Gly Asp Ile Lys Val Ile Gly Ser Pro Val Tyr
            530                 535                 540

Arg Leu Gly Ser Lys Leu Leu Val Glu Asp Lys Gln Gln Gly Asp Glu
545                 550                 555                 560

Trp Glu Phe Tyr Ile Glu Ser Val Ser His Glu Tyr Ser Tyr Thr Ala
                565                 570                 575

Gly Tyr Thr Thr Thr Leu Gly Val Thr Arg Gly Leu Asn Asn Lys Gly
                580                 585                 590

Lys Asp Arg Phe Thr His Leu Trp Gly Lys Ser Ser Asp Phe Lys Gly
            595                 600                 605

Gly Leu Leu Gly Glu Lys Thr Ser Ala Glu Leu Ile Gln Glu Ala Gly
            610                 615                 620

Ser Thr Ser Ser Gly Ser Asp Gly Ser Gly Asp Val Ser Ala Pro Asp
625                 630                 635                 640

Val Gln Gly Ser Asp Val Ala Val Ala Ala Leu Arg Tyr Gly Leu Ala
                645                 650                 655

His Lys Lys Pro Glu Lys Lys Ser Val Tyr Ser Phe Gly Gly Gly Arg
                660                 665                 670

Gly Ser Ser Asn Pro Met Glu Gly Lys Glu Pro Tyr Ala Met Asp Cys
            675                 680                 685

Ser Ser Phe Val Trp Trp Cys Tyr Lys Ala Cys Gly Val Thr Leu Ala
            690                 695                 700

Gly Ala Gln Thr Gln Ala Ile Leu Gly Asp Asp Arg Phe Asn Thr Val
705                 710                 715                 720

Ser Ser Arg Gly Ser Lys Ser Lys Glu Ile Phe Lys Lys Met Gln Val
                725                 730                 735

Gly Asp Leu Val Tyr Phe Tyr Asp Asn Asn Thr His Ile Gly Met Tyr
            740                 745                 750

Ala Gly Glu Gly Lys Phe Leu Gly Cys Asn Gly Asp Gly Ser Trp Asp
            755                 760                 765

Thr Asn Gly Gly Val Gln Leu Lys Pro Met Asp Ser Gly Tyr Trp Trp
770                 775                 780

Thr Gln Phe Gln Gly His Val Ile Arg Phe Val
785                 790                 795

<210> SEQ ID NO 10
<211> LENGTH: 590
<212> TYPE: PRT
<213> ORGANISM: Listeria monocytogenes

<400> SEQUENCE: 10

Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
            35                  40                  45

Ile Val Ser Ala Asp Glu Thr Ala Pro Ala Asp Glu Ala Ser Lys Ser
        50                  55                  60

Ala Glu Ala Asn Thr Thr Lys Glu Ala Ser Ala Thr Ala Thr Pro Glu

```
                65                  70                  75                  80
Asn Thr Ala Lys Gln Thr Val Gly Pro Gln Gln Thr Glu Thr Lys Glu
                    85                  90                  95

Gln Thr Lys Thr Pro Glu Glu Lys Gln Ala Ala Thr Asn Gln Val Glu
                100                 105                 110

Lys Ala Pro Ala Glu Pro Ala Thr Val Ser Asn Pro Asp Asn Ala Thr
                115                 120                 125

Ser Ser Ser Thr Pro Ala Thr Tyr Asn Leu Leu Gln Lys Ser Ala Leu
            130                 135                 140

Arg Ser Gly Ala Thr Val Gln Ser Phe Ile Gln Thr Ile Gln Ala Ser
145                 150                 155                 160

Ser Ser Gln Ile Ala Ala Glu Asn Asp Leu Tyr Ala Ser Val Met Ile
                    165                 170                 175

Ala Gln Ala Ile Leu Glu Ser Ala Tyr Gly Thr Ser Glu Leu Gly Ser
                180                 185                 190

Ala Pro Asn Tyr Asn Leu Phe Gly Ile Lys Gly Ala Tyr Asn Gly Gln
                195                 200                 205

Ser Tyr Thr Lys Gln Thr Leu Glu Asp Asp Gly Lys Gly Asn Tyr Tyr
    210                 215                 220

Thr Ile Thr Ala Lys Phe Arg Lys Tyr Pro Ser Tyr His Gln Ser Leu
225                 230                 235                 240

Glu Asp Tyr Ala Gln Val Ile Arg Lys Gly Pro Ser Trp Asn Pro Asn
                    245                 250                 255

Tyr Tyr Ser Lys Ala Trp Lys Ser Asn Thr Thr Ser Tyr Lys Asp Ala
                260                 265                 270

Thr Lys Ala Leu Thr Gly Thr Tyr Ala Thr Asp Thr Ala Tyr Ala Thr
            275                 280                 285

Lys Leu Asn Asp Leu Ile Ser Arg Tyr Asn Leu Thr Gln Tyr Asp Ser
290                 295                 300

Gly Lys Thr Thr Gly Gly Asn Ser Gly Ser Thr Gly Asn Ser Ser Asn
305                 310                 315                 320

Thr Gly Asn Thr Asn Thr Ser Asn Ala Lys Ile Tyr Thr Val Val Lys
                    325                 330                 335

Gly Asp Ser Leu Trp Arg Ile Ala Asn Asn His Lys Val Thr Val Ala
                340                 345                 350

Asn Leu Lys Ala Trp Asn Asn Leu Lys Ser Asp Phe Ile Tyr Pro Gly
            355                 360                 365

Gln Lys Leu Lys Val Ser Ala Gly Ser Thr Thr Ser Asp Thr Asn Thr
    370                 375                 380

Ser Lys Pro Ser Thr Gly Thr Ser Thr Ser Lys Pro Ser Thr Gly Thr
385                 390                 395                 400

Ser Thr Asn Ala Lys Val Tyr Thr Val Val Lys Gly Asp Ser Leu Trp
                    405                 410                 415

Arg Ile Ala Asn Asn Lys Val Thr Ile Ala Asn Leu Lys Ala Trp
                420                 425                 430

Asn Asn Leu Lys Ser Asp Phe Ile Tyr Pro Gly Gln Lys Leu Lys Val
            435                 440                 445

Ser Ala Gly Ser Thr Ser Asn Thr Asn Thr Ser Lys Pro Ser Thr Asn
    450                 455                 460

Thr Asn Thr Ser Lys Pro Ser Thr Asn Thr Asn Thr Asn Ala Lys Val
465                 470                 475                 480

Tyr Thr Val Ala Lys Gly Asp Ser Leu Trp Arg Ile Ala Asn Asn
                    485                 490                 495
```

```
Lys Val Thr Ile Ala Asn Leu Lys Ala Trp Asn Asn Leu Lys Ser Asp
                500                 505                 510

Phe Ile Tyr Pro Gly Gln Lys Leu Lys Val Ser Ala Gly Ser Thr Thr
            515                 520                 525

Asn Thr Asn Thr Ala Lys Pro Ser Thr Asn Asn Pro Ser Asn Ser Thr
        530                 535                 540

Val Lys Thr Tyr Thr Val Lys Lys Gly Asp Ser Leu Trp Ala Ile Ser
545                 550                 555                 560

Arg Gln Tyr Lys Thr Thr Val Asp Asn Ile Lys Ala Trp Asn Lys Leu
                565                 570                 575

Thr Ser Asn Met Ile His Val Gly Gln Lys Leu Thr Ile Lys
            580                 585                 590

<210> SEQ ID NO 11
<211> LENGTH: 774
<212> TYPE: PRT
<213> ORGANISM: Listeria monocytogenes

<400> SEQUENCE: 11

Met Ile Asn Lys Lys Trp Met Lys Ile Val Met Ile Pro Met Leu Val
1               5                   10                  15

Val Pro Met Tyr Gly Leu Thr Thr Val Gly Gly Gln Leu Gln Asp Ser
            20                  25                  30

Leu Thr Gly Glu Asn Ser Phe Val Lys Glu Val Glu Ala Thr Thr
        35                  40                  45

Ala Ser Gln Gln Ala Phe Ile Asp Lys Ile Ala Pro Ala Ala Gln Ala
    50                  55                  60

Ser Gln Glu Lys Tyr His Leu Leu Ser Ser Ile Thr Leu Ala Gln Ala
65                  70                  75                  80

Ile Leu Glu Ser Gly Trp Gly Lys Ser Gly Leu Ala Thr Gln Gly Tyr
                85                  90                  95

Asn Leu Phe Gly Ile Lys Gly Lys Tyr Asn Gly Gln Ser Val Ile Met
            100                 105                 110

Thr Thr Ser Glu Tyr Val Asn Gly Glu Trp Ile Lys Ile Asp Ala Glu
        115                 120                 125

Phe Arg Lys Tyr Pro Ser Trp Asn Glu Ser Val Thr Asp His Thr Leu
    130                 135                 140

Leu Leu Val Asn Gly Thr Ser Trp Asn Lys Asp Leu Tyr Lys Lys Val
145                 150                 155                 160

Val Asp Ala Thr Asp Tyr Lys Val Thr Ala Met Glu Pro Gln Lys Ala
                165                 170                 175

Gly Tyr Ala Thr Ser Pro Thr Tyr Gly Ala Ser Leu Ile Gln Val Ile
            180                 185                 190

Glu Asn Tyr Asp Leu Ala Lys Tyr Asp Val Leu Tyr Asp Lys Ile Leu
        195                 200                 205

Thr Gln Lys Ser Thr Ser Gly Lys Ala Thr Val Thr Ser Pro Thr Gly
    210                 215                 220

Asn Gly Val Trp Thr Leu Pro Tyr Lys Val Lys Gly Val Gln Ser Val
225                 230                 235                 240

Ser Pro Ala Ser Thr Tyr Ala Asn Lys Asp Ile Asp Leu Val Ser Val
                245                 250                 255

Ala Thr Thr Lys Arg Gly Thr Tyr Tyr Gln Phe Lys Tyr Asn Gly Lys
            260                 265                 270

Val Val Gly Trp Val Asp Gly Lys Ala Leu Thr Ile Tyr Asp Ser Val
```

```
                        275                 280                 285
    Asn Tyr Asp Lys Val Asn Val Gly Arg Ala Lys Ile Thr Ser Pro Val
        290                 295                 300

Ser Asn Gly Ile Trp Ser Lys Pro Tyr Asn Val Tyr Gly Arg Glu Phe
    305                 310                 315                 320

Val Thr Asn Ala Thr Thr Tyr Ala Gln Gln Glu Ile Lys Leu Leu Arg
                    325                 330                 335

Glu Ala Gln Thr Ala Lys Gly Thr Tyr Tyr Gln Phe Ser Ile Asn Asn
                340                 345                 350

Lys Thr Ile Gly Trp Ile Asp Lys Arg Ala Leu Thr Ile Tyr Pro Tyr
            355                 360                 365

Asp Ser Ile Ile Ser Ser Lys Asn Val Asn Leu Asp Gly Gln Ile Thr
        370                 375                 380

Asn Pro Thr Gly Asn Gly Ile Trp Thr Lys Ala Tyr Lys Leu Glu Gly
    385                 390                 395                 400

Thr Thr Ser Val Ala Gln Ala Thr Lys Tyr Ala Asn Lys Asp Val Lys
                    405                 410                 415

Ile Ser Gln Gln Ile Glu Thr Gln His Gly Thr Tyr Tyr Asn Ile Ser
                420                 425                 430

Ile Asp Gly Lys Ala Ile Gly Trp Leu Asp Arg Asn Ala Ile Thr Leu
            435                 440                 445

Tyr Asp Gln Glu Glu Tyr Asn Lys Thr Val Ala Ile Asp Ala Val Val
        450                 455                 460

Lys Asn Val Lys Gly Asn Ala Val Trp Thr Glu Pro Tyr Arg Thr Val
    465                 470                 475                 480

Gly Thr Lys Leu Ile Gly Pro Ala Glu Thr Tyr Leu Asn Lys Glu Val
                    485                 490                 495

Glu Val Val Arg Glu Ala Lys Thr Pro Lys Gly Thr Tyr Tyr Gln Phe
                500                 505                 510

Lys Ser Gly Gly Lys Val Ile Gly Trp Leu Asp Lys Lys Ala Phe Asp
            515                 520                 525

Val Tyr Asp Asn Ile Asn Tyr Asn Lys Ala Val Asn Leu Asp Ala Val
        530                 535                 540

Val Glu Asn Val Thr Gly Asn Ala Val Trp Thr Ala Pro Tyr Lys Ser
    545                 550                 555                 560

Lys Gly Val Lys Leu Val Thr Ser Ala Ala Thr Tyr Lys Gly Lys Ala
                    565                 570                 575

Thr Lys Ile Thr Arg Glu Ala Gln Thr Ser Arg Gly Thr Tyr Tyr Glu
                580                 585                 590

Phe Ser Val Asp Gly Lys Val Ile Gly Trp Leu Asp Lys Lys Ala Phe
            595                 600                 605

Asp Val Tyr Asp Asn Ile Asn Tyr Asn Lys Ala Val Asn Leu Asp Ala
        610                 615                 620

Val Val Glu Asn Val Thr Gly Asn Ala Val Trp Thr Ala Pro Tyr Lys
    625                 630                 635                 640

Ser Lys Gly Val Lys Leu Val Thr Ser Ala Ala Thr Tyr Lys Asp Lys
                    645                 650                 655

Ala Thr Lys Ile Thr Arg Glu Ala Gln Thr Ser Arg Gly Thr Tyr Tyr
                660                 665                 670

Glu Phe Ser Val Asn Gly Lys Val Ile Gly Trp Leu Asp Lys Lys Ala
            675                 680                 685

Phe Asp Val Tyr Asp Ser Ile Glu Tyr Asn Lys Ala Ile Asn Met Thr
        690                 695                 700
```

-continued

Gly Leu Leu Ser Asn Ala Pro Gly Asn Gly Ile Trp Thr Glu Pro Tyr
705                 710                 715                 720

Arg Val Ile Gly Thr Lys Asn Val Gly Gln Ala Thr Ala Tyr Ala Asn
                725                 730                 735

Lys Thr Val Gln Leu Ile Arg Glu Ala Lys Thr Thr Arg Ala Thr Tyr
                740                 745                 750

Tyr Gln Met Ser Val Asn Gly Lys Ile Val Gly Trp Val Asp Lys Arg
            755                 760                 765

Ala Phe Thr Asn Val Lys
    770

<210> SEQ ID NO 12
<211> LENGTH: 294
<212> TYPE: PRT
<213> ORGANISM: Streptomyces coelicolor

<400> SEQUENCE: 12

Met Pro Ala Tyr Ser Ser Leu Ala Arg Arg Gly Arg Arg Pro Ala Val
1               5                   10                  15

Val Leu Leu Gly Gly Leu Val Ser Ala Ser Leu Ala Leu Thr Leu Ala
                20                  25                  30

Pro Thr Ala Ala Ala Ala Pro Leu Ala Pro Pro Gly Lys Asp Val
            35                  40                  45

Gly Pro Gly Glu Ala Tyr Met Gly Val Gly Thr Arg Ile Glu Gln Gly
        50                  55                  60

Leu Gly Ala Gly Pro Asp Glu Arg Thr Ile Gly Pro Ala Asp Thr Ser
65                  70                  75                  80

Gly Val Gln Gly Ile Asp Val Ser His Trp Gln Gly Ser Ile Asn Trp
                85                  90                  95

Ser Ser Val Lys Ser Ala Gly Met Ser Phe Ala Tyr Ile Lys Ala Thr
                100                 105                 110

Glu Gly Thr Asn Tyr Lys Asp Asp Arg Phe Ser Ala Asn Tyr Thr Asn
                115                 120                 125

Ala Tyr Asn Ala Gly Ile Ile Arg Gly Ala Tyr His Phe Ala Arg Pro
        130                 135                 140

Asn Ala Ser Ser Gly Thr Ala Gln Ala Asp Tyr Phe Ala Ser Asn Gly
145                 150                 155                 160

Gly Gly Trp Ser Arg Asp Asn Arg Thr Leu Pro Gly Val Leu Asp Ile
                165                 170                 175

Glu His Asn Pro Ser Gly Ala Met Cys Tyr Gly Leu Ser Thr Thr Gln
                180                 185                 190

Met Arg Thr Trp Ile Asn Asp Phe His Ala Arg Tyr Lys Ala Arg Thr
            195                 200                 205

Thr Arg Asp Val Val Ile Tyr Thr Thr Ala Ser Trp Trp Asn Thr Cys
210                 215                 220

Thr Gly Ser Trp Asn Gly Met Ala Ala Lys Ser Pro Phe Trp Val Ala
225                 230                 235                 240

His Trp Gly Val Ser Ala Pro Thr Val Pro Ser Gly Phe Pro Thr Trp
                245                 250                 255

Thr Phe Trp Gln Tyr Ser Ala Thr Gly Arg Val Gly Val Ser Gly
            260                 265                 270

Asp Val Asp Arg Asn Lys Phe Asn Gly Ser Ala Ala Arg Leu Leu Ala
                275                 280                 285

Leu Ala Asn Asn Thr Ala

<210> SEQ ID NO 13
<211> LENGTH: 334
<212> TYPE: PRT
<213> ORGANISM: Staphylococcus aureus

<400> SEQUENCE: 13

Met Gln Lys Lys Val Ile Ala Ala Ile Ile Gly Thr Ser Ala Ile Ser
1               5                   10                  15

Ala Val Ala Ala Thr Gln Ala Asn Ala Ala Thr Thr His Thr Val Lys
            20                  25                  30

Pro Gly Glu Ser Val Trp Ala Ile Ser Asn Lys Tyr Gly Ile Ser Ile
        35                  40                  45

Ala Lys Leu Lys Ser Leu Asn Asn Leu Thr Ser Asn Leu Ile Phe Pro
    50                  55                  60

Asn Gln Val Leu Lys Val Ser Gly Ser Ser Asn Ser Thr Ser Asn Ser
65                  70                  75                  80

Ser Arg Pro Ser Thr Asn Ser Gly Gly Ser Tyr Tyr Thr Val Gln
                85                  90                  95

Ala Gly Asp Ser Leu Ser Leu Ile Ala Ser Lys Tyr Gly Thr Thr Tyr
            100                 105                 110

Gln Asn Ile Met Arg Leu Asn Gly Leu Asn Asn Phe Phe Ile Tyr Pro
        115                 120                 125

Gly Gln Lys Leu Lys Val Ser Gly Thr Ala Ser Ser Ser Asn Ala Ala
    130                 135                 140

Ser Asn Ser Ser Arg Pro Ser Thr Asn Ser Gly Gly Gly Ser Tyr Tyr
145                 150                 155                 160

Thr Val Gln Ala Gly Asp Ser Leu Ser Leu Ile Ala Ser Lys Tyr Gly
                165                 170                 175

Thr Thr Tyr Gln Lys Ile Met Ser Leu Asn Gly Leu Asn Asn Phe Phe
            180                 185                 190

Ile Tyr Pro Gly Gln Lys Leu Lys Val Thr Gly Asn Ala Ser Thr Asn
        195                 200                 205

Ser Gly Ser Ala Thr Thr Thr Asn Arg Gly Tyr Asn Thr Pro Val Phe
    210                 215                 220

Ser His Gln Asn Leu Tyr Thr Trp Gly Gln Cys Thr Tyr His Val Phe
225                 230                 235                 240

Asn Arg Arg Ala Glu Ile Gly Lys Gly Ile Ser Thr Tyr Trp Trp Asn
                245                 250                 255

Ala Asn Asn Trp Asp Asn Ala Ala Ala Asp Gly Tyr Thr Ile Asp
            260                 265                 270

Asn Arg Pro Thr Val Gly Ser Ile Ala Gln Thr Asp Val Gly Tyr Tyr
        275                 280                 285

Gly His Val Met Phe Val Glu Arg Val Asn Asn Asp Gly Ser Ile Leu
    290                 295                 300

Val Ser Glu Met Asn Tyr Ser Ala Ala Pro Gly Ile Leu Thr Tyr Arg
305                 310                 315                 320

Thr Val Pro Ala Tyr Gln Val Asn Asn Tyr Arg Tyr Ile His
                325                 330

<210> SEQ ID NO 14
<211> LENGTH: 15
<212> TYPE: PRT
<213> ORGANISM: Artificial
<220> FEATURE:

<223> OTHER INFORMATION: amino acid sequence designed to act as a linker

<400> SEQUENCE: 14

Gly Gly Ser Lys Pro Gly Gly Thr Lys Pro Gly Gly Ser Lys Pro
1               5                   10                  15

<210> SEQ ID NO 15
<211> LENGTH: 14
<212> TYPE: DNA
<213> ORGANISM: Artificial
<220> FEATURE:
<223> OTHER INFORMATION: nucleotide sequence designed to act as a primer

<400> SEQUENCE: 15
cacacaccat ggcg                                                        14

<210> SEQ ID NO 16
<211> LENGTH: 12
<212> TYPE: DNA
<213> ORGANISM: Artificial
<220> FEATURE:
<223> OTHER INFORMATION: nucleotide sequence designed to act as a primer

<400> SEQUENCE: 16
tgtgtgacta gt                                                          12

<210> SEQ ID NO 17
<211> LENGTH: 12
<212> TYPE: DNA
<213> ORGANISM: Artificial
<220> FEATURE:
<223> OTHER INFORMATION: nucleotide sequence designed to act as a primer

<400> SEQUENCE: 17
tgtgtgggat cc                                                          12

<210> SEQ ID NO 18
<211> LENGTH: 32
<212> TYPE: DNA
<213> ORGANISM: Artificial
<220> FEATURE:
<223> OTHER INFORMATION: nucleotide sequence designed to act as a primer

<400> SEQUENCE: 18
gtttaacttt aagaaggaga tataccatgg cg                                    32

<210> SEQ ID NO 19
<211> LENGTH: 29
<212> TYPE: DNA
<213> ORGANISM: Artificial
<220> FEATURE:
<223> OTHER INFORMATION: nucleotide sequence designed to act as a primer

<400> SEQUENCE: 19
cctttcgggc tttgttactg cagggatcc                                        29

<210> SEQ ID NO 20
<211> LENGTH: 32
<212> TYPE: DNA
<213> ORGANISM: Artificial
<220> FEATURE:
<223> OTHER INFORMATION: nucleotide sequence designed to act as a primer

<400> SEQUENCE: 20
gtttaacttt aagaaggaga ctgcagatgg cg                                    32

```
<210> SEQ ID NO 21
<211> LENGTH: 29
<212> TYPE: DNA
<213> ORGANISM: Artificial
<220> FEATURE:
<223> OTHER INFORMATION: nucleotide sequence designed to act as a primer

<400> SEQUENCE: 21
cctttcgggc tttgttagtc gacggatcc                                    29

<210> SEQ ID NO 22
<211> LENGTH: 32
<212> TYPE: DNA
<213> ORGANISM: Artificial
<220> FEATURE:
<223> OTHER INFORMATION: nucleotide sequence designed to act as a primer

<400> SEQUENCE: 22
gtttaacttt aagaaggaga gtcgacatgg cg                                32

<210> SEQ ID NO 23
<211> LENGTH: 29
<212> TYPE: DNA
<213> ORGANISM: Artificial
<220> FEATURE:
<223> OTHER INFORMATION: nucleotide sequence designed to act as a primer

<400> SEQUENCE: 23
cctttcgggc tttgttagat atcggatcc                                    29
```

METHODS OF GENERATING AND SCREENING FOR LYTIC CHIMERIC POLYPEPTIDES

This application is a divisional application of U.S. patent application Ser. No. 15/001,455, filed Jan. 20, 2016, which is a divisional application of U.S. patent application Ser. No. 13/704,759, filed Apr. 8, 2013, now issued as U.S. Pat. No. 9,249,447, which is a national phase application under 35 U.S.C. § 371 of International Application No. PCT/EP2011/003022, filed Jun. 17, 2011, which claims priority to European Patent Application No. 10006360.1, filed Jun. 18, 2010, the entire contents and disclosures of which are specifically incorporated herein without disclaimer.

BACKGROUND INFORMATION

Pursuant to 37 C.F.R. 1.821(c), a sequence listing is submitted herewith as an ASCII compliant text file named GRUNP0004USD2_ST25.txt created on Apr. 22, 2019 and having a size of ~47 kilobytes. The content of the aforementioned file is hereby incorporated by reference in its entirety.

TECHNICAL FIELD OF THE INVENTION

The present invention relates to methods of generating and screening for chimeric polypeptides, which comprise at least one cell binding domain (CBD) and at least one enzymatic active domain (EAD) having bacterial cell wall lytic activity. Lytic chimeric polypeptides obtainable by the methods of the present invention are useful in therapy and prophylaxis of pathogenic bacterial colonisation, including bacterial infections and bacterial diseases. The present invention also relates to a library of chimeric polypeptides obtainable by the methods of the present invention.

BACKGROUND OF THE INVENTION

The rapidly increasing number of antibiotic resistant bacteria is a growing challenge for medicine and health care systems worldwide. The use of bacteriophage-derived endolysins for the treatment of bacterial infections is one promising alternative to overcome the increasing number of antibiotic resistance in bacteria. Bacteriophage lysins have been designated using various names including lysins, phage-lysins, virolysins, and endolysins. Structurally, lysins are commonly found as modular proteins with at least one domain that confers the enzymatic activity for hydrolysing specific bonds in the murein or peptidoglycan layer of the bacterial cell wall (enzymatic active domain—EAD), and one domain that confers binding specificity to a cell surface epitope (cell binding domain—CBD). Thus, lysin family members (cell wall or peptidoglycan hydrolases) exhibit a modular design in which a catalytic domain is fused to a specificity mediating or binding domain.

The use of endolysins to kill bacteria was disclosed for the first time by Gasson in 1991 (GB 2 255 561). Further therapeutic and prophylactic applications, including animal model systems, have been described by Nelson et al. 2001. This work describes a topical application of endolysins against group A streptococci and pneumococci in oral and nasopharyngeal treatment. In the field of staphylococcal treatment with bacteriophage derived lysins, Rashel et al. 2007 have shown that endolysin from phage phiMR11 is able to eradicate MRSA in nares of mice and protects mice by intraperitoneal injection from septic death. Further regimes of treatment and pharmaceutical compositions to treat and prevent bacterial infections using phage derived lysins are described in U.S. Pat. No. 5,997,862. However, in all so far published examples using bacteriophage derived endolysins for the treatment of bacterial infections, the amount of protein for an effective treatment is very high. This is due the poor stability of the enzymes and due to inhibition of the activity in application relevant matrices.

In case of lysins against *Staphylococcus* bacteria, a number of wild-type endolysins have been cloned and characterized. For example, protein 17 from phage P68 is a staphylococcal endolysin, which is reported to exhibit antimicrobial activity against *S. aureus* isolates including clinical isolates (Takác and Blasi 2005). Various groups investigated the endolysin of *S. aureus* bacteriophage phi11 in antimicrobial applications. Navarre et al. 1999 identified two enzymatic active domains (amidase and endopeptidase) in phi11 lysin and showed that a mutant with deletion of the amidase domain is still active. Mutants of phi11 (and phi12) endolysin have been characterized by different activity assays on *S. aureus* cell walls, heat inactivated bacteria and on bacterial biofilms (Sass and Bierbaum 2007). All these investigations have in common that they are using artificial experimental conditions for functional characterization of the endolysins. Therefore, no evidences regarding efficacy on living cells under application-relevant conditions can be drawn from these publications. Another staphylolytic enzyme is derived from bacteriophage phiK. This endolysin, called lysK, has been characterized in more detail by the groups of David M. Donavan and R. Paul Ross (O'Flaherty et al. 2005; WO 2008/001342; Becker et al. 2008; Horgan et al. 2009). They have been able to show, that lysK has a broad bactericidal activity against living *staphylococcus* bacteria without discriminating between the different genera. LysK consists of one CBD and two EADs, a cysteine-histidine amino peptidase (CHAP) and an amidase domain. Expressing the individual EADs, they were able to show that the CHAP domain alone is sufficient for killing but not the amidase domain. A deletion mutant, without amidase domain (lysKA221-390), possesses the same killing activity as the wild type protein. Determining MIC values for the truncation/deletion constructs, only MIC values for the wild type LysK and the lysKA221-390 were measurable in TSB medium. The CHAP domain alone showed no measurable activity within such a complex matrix. The determined MIC values are considerably high, 78 µg/ml and 63 µg/ml for wild type lysK and lysKA221-390, respectively. No chimeric lysin based on lysK domains has been described so far. All published data using wild type endolysins clearly show that these molecules are quite effective in killing bacteria in buffer solutions. The advantage of these molecules is the very fast onset time (minutes to hours), and the mode of action from outside without involvement of metabolic processes within the cell. As a matter of fact, for endolysins induction/acquisition of resistance has not been described in literature. On the other hand, wild type endolysins tend to be quite unstable at elevated temperatures and functionality is reduced in complex compositions like culture media or biological fluids. All published MIC values (minimal inhibitory concentration) or MBC values (minimal bactericidal concentration) are in the range >50 µg/ml. It can be speculated that in many cases MIC values are not reported for experimental reasons.

Enzymes with cell wall degrading properties similar to bacteriophage lysins (endolysins) can also be found in bacteria. Autolysins are bacteriolytic enzymes that digest the cell-wall peptidoglycan of the bacteria that produce them.

Autolysins are involved in cell wall reconstruction during bacterial cell division. Although potentially lethal, autolysins appear to be universal among bacteria that possess peptidoglycan. "Autolysin" is the term used for lysins, which are produced by bacteria and involved in cell division, while the term "lysin" or "endolysin" refers to lytic enzymes, which are involved in phage release, as described herein above. Bacteriocins are molecules also produced and secreted by microorganisms. They are antibacterial substances of a proteinaceous nature that are produced by different bacterial species. A subclass of bacteriocins consists of enzymes (proteinaceous toxins) which are produced by bacteria to inhibit the growth of similar or closely related concurrence bacterial strain(s) in their habitat. They also contain CBDs and EADs. Bacteriocins target prokaryotes but not eukaryotes, making them safe for human consumption.

The bacteriocin lysostaphin is naturally produced by *Staphylococcus simulans* to combat *Staphylococcus aureus*. It is highly effective in vitro and capable of killing bacteria in complex media (Kumar J. 2008). Lysostaphin consists of one CBD and one glycyl-glycine endopeptidase domain, which cleaves the characteristic penta-glycine cross bridge in *S. aureus* cell walls. This molecule has been tested in various animal models and exhibit good efficacy even in complex matrices (Kokai-Kun et al. 2007; Kusuma et al. 2007). The reported MIC values of lysostaphin are more than 1000-fold lower compared to lysK (<0.02 µg/ml). The major disadvantage of lysostaphin is the occurrence of resistance in *S. aureus*. Two different genetic escape mechanisms have been described so far: First, incorporation of serine into the penta-glycine bridge (DeHart et al. 1995). Secondly, shortening of the glycine bridge; gly3 or gly2 (Ehlert et al. 1997; Stranden et al. 1997). It can be assumed that such monogenic resistance marker will rapidly be selected under selection pressure.

Enzymatic active domains (EADs) can further be found in structural bacteriophage proteins (tail associated muralytic enzymes). They are part of the early infection machinery of the bacteriophage, locally hydrolyzing the cell wall prior to DNA injection.

In order to deal with the fact of resistance development, groups started to investigate the combination of different lysins. For example, synergistic effects between lysK and lysostaphin (Becker et al. 2008) have been described, resulting in reduced effective concentrations for killing *S. aureus*. The drawback of this concept is, that in case of occurrence of resistance against one component (for example, lysostaphin), the concentration of the second component will not be effective anymore. Furthermore, a composition with two active components is difficult to develop and expensive in production. While Staphylococci and Streptococci belong to the most common human pathogenic bacteria, *Listeria* are likewise widespread human and animal pathogenic bacteria, eliciting the disease pattern of listeriosis. *Listeria* phage lysins have been proven as antimicrobial substances for decontamination of *listeria*. For example, WO 2004/004495 describes the *Listeria*-phage lysine PlyP100 from the *Listeria* phage P100 and its successful application in *Listeria* contamination of food. WO 96/07756 describes phage lysins from *Listeria*-infecting phages exhibiting lytic activity on the cell wall of *Listeria* bacteria. In particular, WO 96/07756 discloses *Listeria* phage lysins Ply118, Ply500 and Ply511 from *Listeria* phages A118, A500 and A511, respectively. Specifically, Ply511 has been shown to have a broad host range against a multitude of *Listeria* serovars. WO 2010/010192 describes the *Listeria* lysine PlyP40 from *Listeria* phage P40 and its use as antimicrobial substance in decolonisation of *Listeria*.

Sanz et al. 1996 describes the construction of a chimeric trifunctional pneumococcal peptidoglycan hydrolase by fusing a choline-binding domain with two catalytic modules that provide lysozyme and amidase activity. It was demonstrated that the three modules can acquire the proper folding conformation in the three-domain chimeric enzyme and that the activity of the chimeric enzyme is comparable to that of the parent enzymes.

It is known that a combination of domains (CBDs and EADs) from different source organisms is possible. However, the purpose of such domain exchange experiments was always to alter or broaden the host specificity of the lysins (Diaz et al. 1990; Croux et al. 1993; Donovan et al. 2006). So far, no systematic domain exchange experiments have been performed with endolysin-derived EADs to obtain lytic molecules with improved properties with respect to efficacy, resistance potential and stability.

The present invention successfully provides methods of generating and screening for lytic chimeric polypeptides, which can be used in the control of bacterial contamination, colonization and infection. The methods according to the present invention allow the generation and identification of new and highly effective lytic chimeric polypeptides as a substitute for antibiotics or bacteria killing substances.

SUMMARY OF THE INVENTION

The use of lytic domains of a bacteriophage endolysin, a bacteriocin or a bacterial autolysin, specifically lytic domains of bacteriophage derived endolysins, for the treatment of bacterial infections is a promising alternative to overcome the increasing number of antibiotic resistance in bacteria. As shown in principle by a number of investigators, it is possible to kill bacteria in vitro and in animal models. Advantage of such lytic proteins is the fast onset of action and the lower risk of resistance development against these enzymes.

In accordance with, inter alia, Sanz et al. 1996 and based on the modular theory of protein evolution, the inventors of the present application were aiming at constructing fully active lytic chimeric enzymes with improved biological properties, which can be used in the treatment and prophylaxis of pathogenic bacterial contamination, colonisation and infection. The methods of the present invention provide for means in generating and screening for such improved lytic chimeric polypeptides based on the random assembly of functional cell binding domains and enzymatically active domains exhibiting lytic activity on bacterial cell walls.

The present invention successfully provides novel methods of generating and screening for chimeric polypeptides, which can be used in the treatment and prophylaxis of pathogenic bacterial contamination, colonisation and infection. The novel methods are based on random recombination of protein domains, and the chimeric polypeptides obtainable by the methods according to the invention are characterized in that they comprise at least one enzymatic active domain and at least one cell binding domain. Thus, the present invention provides for novel combinations of EADs and CBDs from different source or origin and allows generating and screening for chimeric lytic polypeptides with improved properties regarding binding and/or lysis of bacterial cells. The present invention also provides a library of chimeric polypeptides obtainable by the methods of the present invention.

The first aspect of the invention comprises the following items:

[1] A method of screening for a lytic chimeric polypeptide comprising the steps of:

(a) providing one or more DNA sequences each encoding at least one cell binding domain (CBD) and one or more DNA sequences each encoding at least one enzymatic active domain (EAD) and optionally one or more DNA sequences each encoding at least one CBD and at least one EAD, wherein the EAD is selected from the group consisting of (i) the lytic domain of a bacteriophage lysin, (ii) the lytic domain of a bacteriocin, (iii) the lytic domain of a bacterial autolysin; and (iv) a bacteriophage tail-associated protein having lytic activity.

(b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second ($2^{nd}$) domain sequence selected from the domain sequences of (a) using a pair of primers designed to introduce:

(i) in case of 5'-end labelling of the $1^{st}$ domain: at the 5'-end the same restriction site as at the 3'-end of the $1^{st}$ domain, and at the 3'-end a restriction site different from the restriction sites introduced into the $1^{st}$ domain sequence, (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;

wherein the pair of primers is further designed such that the restriction sites are different at the 5'-end and the 3'-end of the $3^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;

wherein the pair of primers is further designed such that the restriction sites are different at the 5'-end and the 3'-end of each of said one or more further domain sequences;

(f) performing a restriction digest of the amplified domain sequences of any of steps (b) to (e) with restriction enzymes targeting the restriction sites introduced in any of steps (b) to (e), wherein a restriction digest is not performed on the restriction site introduced to an end carrying a tag labelling;

(g) ligating the digested $1^{st}$ and $2^{nd}$ domain sequence obtained in step (f) to obtain a ligation product comprising the $1^{st}$ and $2^{nd}$ domain sequence;

(h) binding the ligation product of step (g) to a solid support using the tag labeling of the $1^{st}$ domain sequence to obtain a bound ligation product comprising the $1^{st}$ and $2^{nd}$ domain sequence;

(j) optionally ligating the digested $3^{rd}$ domain sequence of (d) obtained in step (f) to the bound ligation product of step (h) to obtain a bound ligation product comprising the $1^{st}$, $2^{nd}$ and $3^{rd}$ domain sequence;

(k) optionally ligating one or more digested domain sequences of (e) obtained in step (f) to the bound ligation product of step (j) to obtain a bound ligation product comprising one or more further domain sequences of (e);

(l) releasing the ligation product obtained in any of steps (h) to (k) from the solid support; (m) cloning the ligation product obtained in step (l) into an expression vector; (n) introducing the vector obtained in step (m) into an expression host, preferably into a bacterial expression host;

(o) culturing the expression host of step (n) carrying the vector obtained in step (m) under conditions suitable to allow expression of a lytic polypeptide encoded by the domain sequences of the cloned ligation product;

(p) selecting and isolating an expression clone expressing a lytic polypeptide according to step (o) using the lytic activity of the polypeptide; and (q) characterizing the lytic polypeptide expressed by the isolated expression clone of step (p) and identifying a lytic chimeric polypeptide.

[2] A method of generating a chimeric polypeptide having at least one cell binding domain (CBD) and at least one enzymatic active domain (EAD), the method comprising the steps of:

(a) providing one or more DNA sequences each encoding at least one CBD and one or more DNA sequences each encoding at least one EAD, and optionally one or more DNA sequences each encoding at least one CBD and at least one EAD, wherein the EAD is selected from the group consisting of (i) the lytic domain of a bacteriophage lysin;

(ii) the lytic domain of a bacteriocin;

(iii) the lytic domain of a bacterial autolysin; and (iv) a bacteriophage tail-associated protein having lytic activity.

(b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second ($2^{nd}$) domain sequence selected from the domain sequences of (a) using a pair of primers designed to introduce:

(i) in case of 5'-end labelling of the $1^{st}$ domain: at the 5'-end the same restriction site as at the 3'-end of the first domain, and at the 3'-end a restriction site different from the restriction sites introduced into the $1^{st}$ domain sequence, (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the 1$^{st}$ domain: at the 3'-end the same restriction site as at the 5'-end of the preceding 2$^{nd}$ domain, and at the 5'-end a restriction site that is different from that at the 3'-end of the 1$^{st}$ domain;

wherein the pair of primers is further designed such that the restriction sites are different at the 5'-end and the 3'-end of the 3$^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the 1$^{st}$ domain: at the 5'-end the same restriction site as at the 3'-end of the preceding domain, and at the 3'-end a restriction site that is different from that at the 5'-end of the 1$^{st}$ domain, (ii) in case of 3'-end labelling of the 1$^{st}$ domain: at the 3'-end the same restriction site as at the 5'-end of the preceding domain, and at the 5'-end a restriction site that is different from that at the 3'-end of the 1$^{st}$ domain;

wherein the pair of primers is further designed such that the restriction sites are different at the 5'-end and the 3'-end of each of said one or more further domain sequences; (f) performing a restriction digest of the amplified domain sequences of any of steps (b) to (e) using restriction enzymes targeting the restriction sites introduced in any of steps (b) to (e), wherein a restriction digest is not performed on the restriction site introduced to an end carrying a tag labelling;

(g) ligating the digested 1$^{st}$ and 2$^{nd}$ domain sequence obtained in step (f) to obtain a ligation product comprising the 1$^{st}$ and 2$^{nd}$ domain sequence;

(h) binding the ligation products of step (g) to a solid support using the tag labeling of the 1$^{st}$ domain sequence to obtain a bound ligation product comprising the 1$^{st}$ and 2$^{nd}$ domain sequence;

(j) optionally ligating the digested 3$^{rd}$ domain sequence of (d) obtained in step (f) to the bound ligation product of step (h) to obtain a bound ligation product comprising the 1$^{st}$, 2$^{nd}$ and 3$^{rd}$ domain sequence;

(k) optionally ligating one or more digested domain sequences of (e) obtained in step (f) to the bound ligation product of step (j) to obtain a bound ligation product comprising one or more further domain sequences of (e);

(l) releasing the ligation product obtained in any one of steps (h) to (k) from the solid support; and (m) characterizing the ligation product obtained in step (l) and identifying chimeric polypeptides having at least one CBD and at least one EAD.

[3] The method of item [1] or [2], further comprising a washing step after binding the first ligation product to the solid support in step (h) to remove unbound ligation products and/or non-ligated domain sequences.

[4] The method of any one of items [1] to [3], wherein steps (g) and (h) are replaced by a step of binding the digested 1$^{st}$ domain sequence to a solid support using the tag labeling at the 5'-end or 3'-end, respectively, and a subsequent step of ligating the digested 2" domain sequence of (c) obtained in step (f) to the bound 1$^{st}$ domain sequence to obtain a bound ligation product comprising the 1$^{st}$ and 2$^{nd}$ domain sequence.

[5] The method of item [4], further comprising a step of removing unbound domain sequences after binding the first ligation product to the solid support, and optionally a further step of removing non-ligated domain sequences after ligating the second domain sequence to the bound first domain sequence.

[6] The method for screening a lytic chimeric polypeptide of any one of items [1] and [3] to [5], further comprising a step of removing non-ligated domain sequences after each ligation step performed in any of steps (j) to (k).

[7] The method for generating chimeric polypeptides having at least one CBD and at least one EAD of any one of items [2] to [5], further comprising a step of removing non-ligated domain sequences after each ligation step performed in steps (j) and (k).

[8] The method of any one of items [1] to [7], wherein the domain sequences of (a) are cloned into a vector prior to amplification.

[9] The method of any one of items [1] to [8], wherein the step of releasing the ligation product or ligation products from the solid support is carried out using a restriction enzyme targeting the restriction site at that end of the 1$^{st}$ domain, which is carrying the tag labelling.

[10]. The method of any one of items [1] to [9], wherein in case of repeated ligation steps optionally after any repeated ligation step part of the obtained bound ligation product is separated from the method prior to performing a subsequent ligation step.

[11] The method of any one of items [1] to [10], wherein the solid support is a particle, a surface of a device, a foil or a fleece.

[12] The method of item [11], wherein the particle is a silica bead or an organic polymer bead being magnetic.

[13] A lytic chimeric polypeptide obtainable by the method for screening a lytic chimeric polypeptide of any one of items [1] and [3] to [12].

[14] A chimeric polypeptide or a plurality of chimeric polypeptides obtainable by the method of generating chimeric polypeptides having at least one CBD and at least one EAD of any one of items [2] to [12].

[15] A DNA library comprising the clones carrying the ligation products obtained in the method of any one of items [1] to [12].

A second aspect of the invention comprises the following items:

1". A method of screening for a lytic chimeric polypeptide comprising the steps of:

(a) providing one or more DNA sequences each encoding at least one cell binding domain (CBD) and one or more DNA sequences each encoding at least one enzymatic active domain (EAD) and optionally one or more DNA sequences each encoding at least one CBD and at least one EAD, wherein the EAD is selected from the group consisting of (i) the lytic domain of a bacteriophage lysin, (ii) the lytic domain of a bacteriocin, (iii) the lytic domain of a bacterial autolysin; and (iv) a bacteriophage tail-associated protein having lytic activity;

(b) amplifying a first (1$^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second (2nd) domain sequence selected from the domain sequences of (a) using a pair of primers designed to introduce:

(i) in case of 5'-end labelling of the 1$^{st}$ domain: at the 5'-end the same restriction site as at the 3'-end of the 1$^{st}$ domain, and at the 3'-end a restriction site different from the restriction sites introduced into the 1$^{st}$ domain sequence, (ii) in case of 3'-end labelling of the 1$^{st}$ domain: at the 3'-end the same restriction site as at the 5'-end of the 1$^{st}$ domain, and at the 5'-end a restriction site different from the restriction sites introduced into the 1$^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;

wherein the pair of primers is further designed such that the restriction sites are different at the 5'-end and the 3'-end of the $3^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;

wherein the pair of primers is further designed such that the restriction sites are different at the 5'-end and the 3'-end of each of said one or more further domain sequences; (f) performing a restriction digest of the domain sequences of any of steps (b) to (e):

(i) in case of 5'-end labelling of the $1^{st}$ domain: performing a restriction digest of the domain sequence of step (b) with a restriction enzyme targeting the restriction site at the 3'-end and performing a restriction digest of the domain sequences of any of steps (c) to (e) with restriction enzymes targeting the restriction sites at the 5'-ends, (ii) in case of 3'-end labelling of the $1^{st}$ domain: performing a restriction digest of the domain sequence of step (b) with a restriction enzyme targeting the restriction site at the 5'-end and performing a restriction digest of the domain sequences of any of steps (c) to (e) with restriction enzymes targeting the restriction sites at the 3'-ends;

(g) ligating the digested $1^{st}$ and $2^{nd}$ domain sequence obtained in step (f) to obtain a ligation product comprising the $1^{st}$ and $2^{nd}$ domain sequence;

(h) binding the ligation product of step (g) to a solid support using the tag labeling of the $1^{st}$ domain sequence to obtain a bound ligation product comprising the $1^{st}$ and $2^{nd}$ domain sequence;

(j) performing a restriction digest of the bound ligation product of step (h):

(i) in case of 5'-end labelling of the $1^{st}$ domain: performing a restriction digest of the bound ligation product of (h) with a restriction enzyme targeting the 3'-end of the $2^{nd}$ domain, (ii) in case of 3'-end labelling of the $1^{st}$ domain: performing a restriction digest of the bound ligation product of (h) with a restriction enzyme targeting the 5'-end of the $2^{nd}$ domain; (k) optionally ligating the digested $3^{rd}$ domain sequence of step (d) obtained in step (f) to the bound ligation product of step (j) to obtain a bound ligation product comprising the $1^{st}$, $2^{nd}$ and $3^{rd}$ domain sequence;

(l) performing a restriction digest of the bound ligation product of step (k):

(i) in case of 5'-end labelling of the $1^{st}$ domain: performing a restriction digest of the bound ligation product of step (k) with a restriction enzyme targeting the 3'-end of the $3^{rd}$ domain.

(ii) in case of 3'-end labelling of the $1^{st}$ domain: performing a restriction digest of the bound ligation product of step (k) with a restriction enzyme targeting the 5'-end of the $3^{rd}$ domain.

(m) optionally ligating one or more digested domain sequences of (e) obtained in step (f) to the bound ligation product of step (l) to obtain a bound ligation product comprising one or more further domain sequences of step (e), thereby performing after each ligation step a restriction digest of the bound ligation product as follows:

(i) in case of 5'-end labelling of the $1^{st}$ domain: performing a restriction digest of the bound ligation product with a restriction enzyme targeting the 3'-end of the said further domain sequence that was ligated to the bound ligation product, (ii) in case of 3'-end labelling of the $1^{st}$ domain: performing a restriction digest of the bound ligation product with a restriction enzyme targeting the 5'-end of the said further domain sequence that was ligated to the bound ligation product;

(n) releasing the ligation product obtained in any of steps (h) to (m) from the solid support;

(o) cloning the ligation product obtained in step (n) into an expression vector;

(p) introducing the vector obtained in step (o) into an expression host, preferably into a bacterial expression host;

(q) culturing the expression host of step (p) carrying the vector obtained in step (o) under conditions suitable to allow expression of a lytic polypeptide encoded by the domain sequences of the cloned ligation product;

(r) selecting and isolating an expression clone expressing a lytic polypeptide according to step (q) using the lytic activity of the polypeptide; and (s) characterizing the lytic polypeptide expressed by the isolated expression clone of step (r) and identifying a lytic chimeric polypeptide.

2". A method of generating a chimeric polypeptide having at least one cell binding domain (CBD) and at least one enzymatic active domain (EAD), the method comprising the steps of:

(a) providing one or more DNA sequences each encoding at least one CBD and one or more DNA sequences each encoding at least one EAD, and optionally one or more DNA sequences each encoding at least one CBD and at least one EAD, wherein the EAD is selected from the group consisting of (i) the lytic domain of a bacteriophage lysin;
(ii) the lytic domain of a bacteriocin;
(iii) the lytic domain of a bacterial autolysin; and
(iv) a bacteriophage tail-associated protein having lytic activity.

(b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second ($2^{nd}$) domain sequence selected from the domain sequences of (a) using a pair of primers designed to introduce:

(i) in case of 5'-end labelling of the $1^{st}$ domain: at the 5'-end the same restriction site as at the 3'-end of the first domain, and at the 3'-end a restriction site different from the restriction sites introduced into the $1^{st}$ domain sequence, (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;

wherein the pair of primers is further designed such that the restriction sites are different at the 5'-end and the 3'-end of the $3^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;

wherein the pair of primers is further designed such that the restriction sites are different at the 5'-end and the 3'-end of each of said one or more further domain sequences;

(f) performing a restriction digest of the domain sequences of any of steps (b) to (e):

(i) in case of 5'-end labelling of the $1^{st}$ domain: performing a restriction digest of the domain sequence of step (b) with a restriction enzyme targeting the restriction site at the 3'-end and performing a restriction digest of the domain sequences of any of steps (c) to (e) with restriction enzymes targeting the restriction sites at the 5'-ends, (ii) in case of 3'-end labelling of the $1^{st}$ domain: performing a restriction digest of the domain sequence of step (b) with a restriction enzyme targeting the restriction site at the 5'-end and performing a restriction digest of the domain sequences of any of steps (c) to (e) with restriction enzymes targeting the restriction sites at the 3'-ends;

(g) ligating the digested $1^{st}$ and $2^{nd}$ domain sequence obtained in step (f) to obtain a ligation product comprising the $1^{st}$ and $2^{nd}$ domain sequence;

(h) binding the ligation product of step (g) to a solid support using the tag labeling of the $1^{st}$ domain sequence to obtain a bound ligation product comprising the $1^{st}$ and $2^{nd}$ domain sequence;

(j) performing a restriction digest of the bound ligation product of step (h):

(i) in case of 5'-end labelling of the $1^{st}$ domain: performing a restriction digest of the bound ligation product of (h) with a restriction enzyme targeting the 3'-end of the $2^{nd}$ domain, (ii) in case of 3'-end labelling of the $1^{st}$ domain: performing a restriction digest of the bound ligation product of (h) with a restriction enzyme targeting the 5'-end of the $2^{nd}$ domain;

(k) optionally ligating the digested $3^{rd}$ domain sequence of (d) obtained in step (f) to the bound ligation product of step (j) to obtain a bound ligation product comprising the $1^{st}$, $2^{nd}$ and $3^{rd}$ domain sequence;

(l) performing a restriction digest of the bound ligation product of step (k):

(i) in case of 5'-end labelling of the $1^{st}$ domain: performing a restriction digest of the bound ligation product of step (k) with a restriction enzyme targeting the 3'-end of the $3^{rd}$ domain.

(ii) in case of 3'-end labelling of the $1^{st}$ domain: performing a restriction digest of the bound ligation product of step (k) with a restriction enzyme targeting the 5'-end of the $3^{rd}$ domain.

(m) optionally ligating one or more digested domain sequences of (e) obtained in step (f) to the bound ligation product of step (l) to obtain a bound ligation product comprising one or more further domain sequences of step (e), thereby performing after each ligation step a restriction digest of the bound ligation product as follows:

(i) in case of 5'-end labelling of the $1^{st}$ domain: performing a restriction digest of the bound ligation product with a restriction enzyme targeting the 3'-end of the said further domain sequence that was ligated to the bound ligation product, (ii) in case of 3'-end labelling of the $1^{st}$ domain: performing a restriction digest of the bound ligation product with a restriction enzyme targeting the 5'-end of the said further domain sequence that was ligated to the bound ligation product;

(n) releasing the ligation product obtained in any of steps (h) to (m) from the solid support;

(o) characterizing the ligation product obtained in step (n) and identifying chimeric polypeptides having at least one CBD and at least one EAD.

3". The method of item 1" or 2", further comprising a washing step after binding the first ligation product to the solid support in step (h) to remove unbound ligation products and/or non-ligated domain sequences.

4". The method of any one of items 1" to 3", wherein steps (g) and (h) are replaced by a step of binding the digested $1^{st}$ domain sequence to a solid support using the tag labeling at the 5'-end or 3'-end, respectively, and a subsequent step of ligating the digested 2" domain sequence of (c) obtained in step (f) to the bound $1^{st}$ domain sequence to obtain a bound ligation product comprising the $1^{st}$ and $2^{nd}$ domain sequence.

5". The method of item 4", further comprising a step of removing unbound domain sequences after binding the first ligation product to the solid support, and optionally a further step of removing non-ligated domain sequences after ligating the second domain sequence to the bound first domain sequence.

6". The method for screening a lytic chimeric polypeptide of any one of items 1" and 3" to 5", further comprising a step of removing non-ligated domain sequences and/or undesired products resulting from the restriction digest after each ligation and restriction step performed in any of steps (h) to (m).

7". The method for generating chimeric polypeptides having at least one CBD and at least one EAD of any one of items 2" to 5", further comprising a step of removing non-ligated domain sequences and/or undesired products resulting from the restriction digest after each ligation and restriction step performed in steps (k) to (m).

8". The method of any one of items 2" to 5", wherein step (o) comprises the steps of:

(o) cloning the ligation product obtained in step (n) into an expression vector;

(p) introducing the vector obtained in step (o) into an expression host, preferably into a bacterial expression host;

(q) culturing the expression host of step (p) carrying the vector obtained in step (o) under conditions suitable to allow expression of a lytic polypeptide encoded by the domain sequences of the cloned ligation product;

(r) selecting and isolating an expression clone expressing a lytic polypeptide according to step (q) using the lytic activity of the polypeptide; and (s) characterizing the lytic polypeptide expressed by the isolated expression clone of step (r) and identifying a lytic chimeric polypeptide having at least one CBD and at least one EAD.

9". The method of any one of items 1" to 8", wherein the domain sequences of (a) are cloned into a vector prior to amplification.

10". The method of any one of items 1" to 9", wherein the step of releasing the ligation product or ligation products from the solid support is carried out using a restriction enzyme targeting the restriction site at that end of the 1$^{st}$ domain, which is carrying the tag labelling.

11". The method of any one of items 1" to 10", wherein in case of repeated ligation steps optionally after any repeated ligation step part of the obtained bound ligation product is separated from the method prior to performing a subsequent ligation step.

12". The method of any one of items 1" to 11", wherein the solid support is a particle, a surface of a device, a foil or a fleece.

13". The method of item 12", wherein the particle is a silica bead or an organic polymer bead being magnetic.

14". A lytic chimeric polypeptide obtainable by the method for screening a lytic chimeric polypeptide of any one of items 1" and 3" to 13".

15". A chimeric polypeptide or a plurality of chimeric polypeptides obtainable by the method of generating chimeric polypeptides having at least one CBD and at least one EAD of any one of items 2" to 13".

16". A library of chimeric polypeptides obtainable by the method of any one of items 2" to 13".

BRIEF DESCRIPTION OF THE DRAWINGS

FIG. 2 shows the cloning vector pET14b with an insert (here: EAD) from NcoI to BamHI site. The forward PCR primer overlaps 3' with the insert and introduces for position 1 a NcoI site and a biotin tag, for position 2 a PstI site and for position 3 a SalI site. The reverse PCR primer overlaps 5' with the insert and introduces for position 1 a PstI site, for position 2 a SalI site and for position 3 a EcoRV site.

FIG. 3 shows the agarose gel with the PCR products of EAD500 of position 1, position 2 and position 3. The products were generated with the position specific PCR primers and the cloned EAD500 as template. The generated fragments have the same size but carry the different, position specific restriction sites.

FIG. 4 shows a binding experiment of biotinylated and non-biotinylated DNA and streptavidin coated beads. The biotin tags can be cut off by NcoI digest. S1 is the supernatant after incubation of DNA with streptavidin coated beads and contains biotinylated DNA with 1400 bp and 600 bp as well as non-biotinylated DNA with 700 bp. The non-biotinylated DNA could not bind to the streptavidin beads because of the lack of a biotin tag. The biotinylated DNA exceeded the binding capacity of the streptavidin beads and was thus in the supernatant. The beads were washed and resuspended in buffer and a restriction digest with NcoI was performed. The supernatant was removed (=S2). S2 contains only DNA with 1400 bp and 600 bp. These fragments were biotinylated and could bind to the beads. The Beads themselves showed no DNA bands at the agarose gel.

FIG. 6 shows an agarose gel with the PCR products of the EADs (E) for position 1 (EAD511: 640 bp, EADP40: 730 bp, EADPSA: 601 bp, EADP35: 505 bp) amplified with the specific primers for position 1 and the CBDs (C) for position 2 (CBD511: 550 bp, CBDP40 variant A: 463 bp, CBD500: 532 bp, CBD006: 337 bp) amplified with the specific primers for position 2.

FIG. 7 shows an agarose gel of the random ligation of the 4 N-terminal EADs and the 4 C-terminal CBDs. About 0.06 pmol of each fragment were applicated in lane D as indicated by the arrows. Lane L shows the ligation products with 0.06 pmol of each fragment. Lane NS shows the ligation products out of 0.06 pmol of each fragment that were captured via biotin tag by streptavidin coated beads and cut off the beads by NcoI.

FIG. 8 shows a scheme of the pQE60-lib vector. The multiple cloning site was adapted for cloning of inserts with an 5' NcoI site and a 3' PstI, SalI or EcoRV site. The translation begins with the ATG of the NcoI site and ends at a vector intrinsic stop codon between the EcoRV site and HindIII site.

FIG. 9 shows a lysis selection plate with induced endolysin expressing *E. coli* M15 tranformants. Transformed *E. coli* cells were plated on lysis plates with heat inactivated *Listeria* cells WSLC 2011 (*Listeria innocua*, serotype 6a). The lysis selection plate contains LB Top Agar, heat inactivated *Listeria* cells WSLC 2011 (*Listeria innocua*, serotype 6a), IPTG and Ampicillin. *E. coli* M15 were transformed with pQE60-lib carrying endolysins and plated. *E. coli* cells that express a soluble and active protein are surrounded by a clearance of the *Listeria* cells.

FIG. 10 shows the confirmation of the 16 possible variants A to P of the 4 N-terminal EADs (EADP40, EADP35, EAD511, EADPSA) and the 4 C-terminal CBDs (CBD511, CBD500, CBDP40 variant A, CBD006). Colony PCR was performed with pQE forward and pQE reverse primer and digested at the PstI site where the domains were ligated together during the cloning procedure. The resulting fragments were analysed by agarose gel electrophoresis. The separated domains can be identified by the individual domain sizes. The domain sizes include also fragments from the domain borders to the priming sites of pQE forward and pQE reverse primer. CBDP40 means CBDP40-A construct of Table 1.

FIG. 12: Lytic spectrum of the 16 variants follows the behaviour of corresponding CBDs.

FIG. 12 shows the lytic behaviour of the variants A-P against *Listeria* serovars 6a (*L. innocua* WSLC2011), 1/2a (*L. monocytogenes* EGDe) and 4b (*L. monocytogenes* ScottA). The proteins behave corresponding to the CBD binding spectra: variants A, D, F and K have CBD511 and lyse all three serovars, the CBD511 binds all three serovars. Variants with CBD500 (B, E, G and L) lyse only serovars 6a and 4b, variants with CBD006 (I, M, O P) lyse mainly serovars 1/2a. Candidates with CBDP40 are not lytic active against the tested *Listeria* cells what means that this CBDP40-variant A is not functionable. Sv 6a: *L. innocua* WSLC2011, 1/2a: *L. monocytogenes* EGDe, 4b: *L. monocytogenes* ScottA.

FIGS. 13A and 13B shows the claimed methods using either 5'-labeling (FIG. 13A) or 3'-labeling (FIG. 13B) of the $1^{st}$ domain according to the first aspect of the invention. According to the first aspect of the invention, the claimed methods comprise performing a restriction digest on the amplified domain sequences of any of steps (b) to (e) with restriction enzymes targeting the restriction sites introduced in any of steps (b) to (e), wherein a restriction digest is not performed on the restriction site introduced to an end carrying a tag labelling.

FIGS. 14A and 14B shows the claimed methods using either 5'-labeling (FIG. 14A) or 3'-labeling (FIG. 14B) of the $1^{st}$ domain according to the second aspect of the invention. According to the second aspect of the invention, the claimed methods comprise performing a restriction digest on the domain sequences of any of steps (b) to (e) as follows:

Figure 14A:
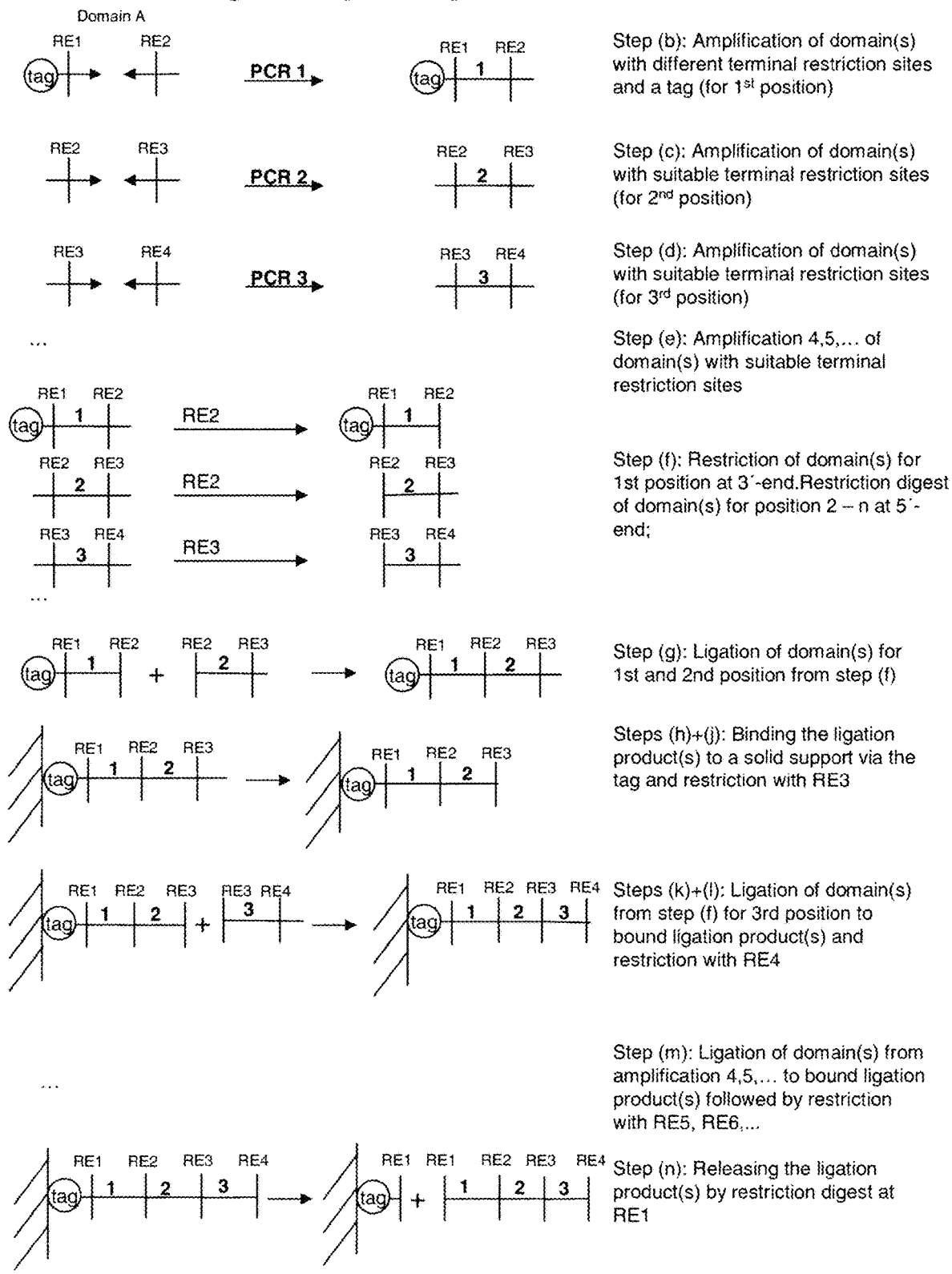
FIG. 14A-B.
Figure 14B:
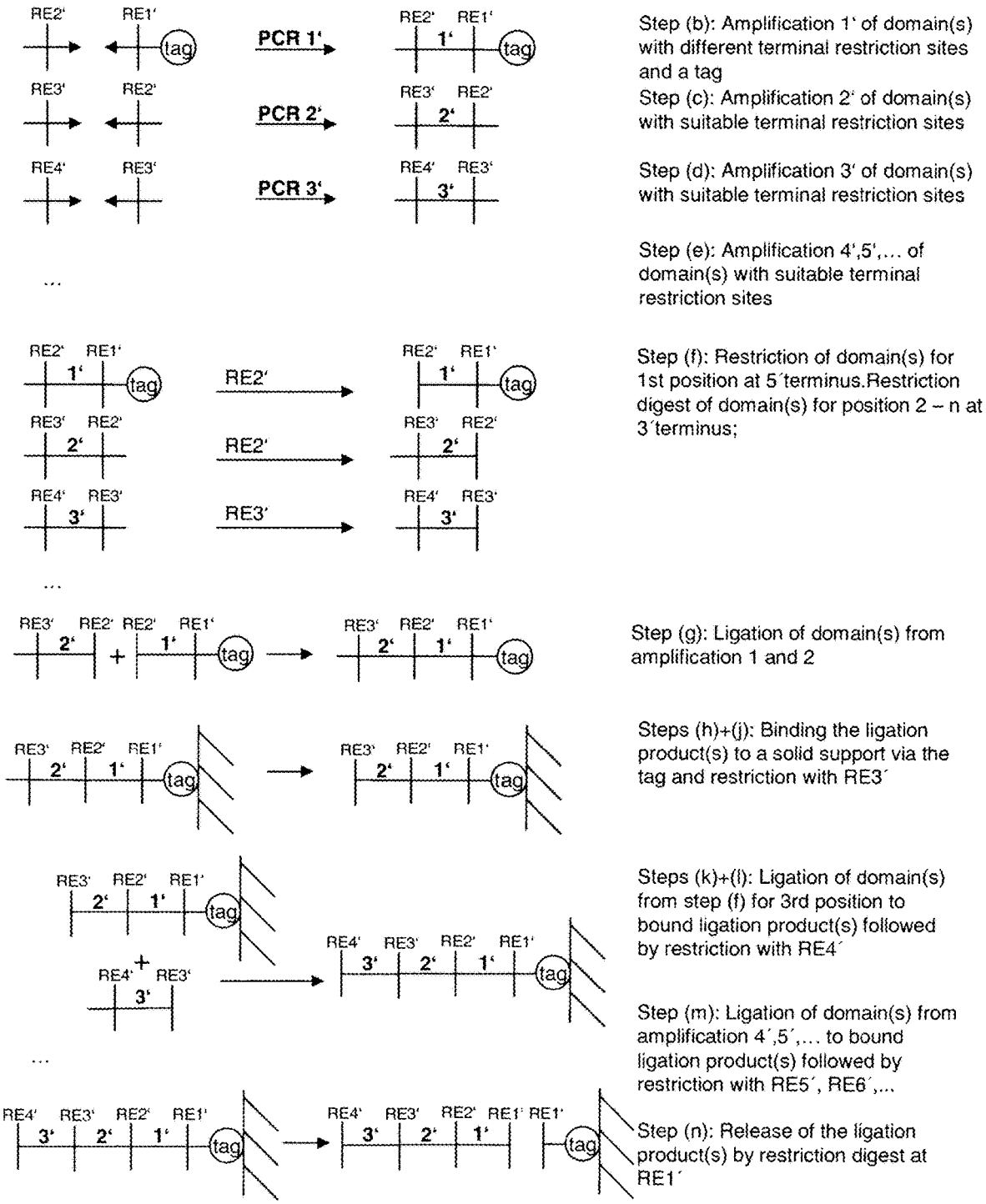

(i) in case of 5'-end labelling of the $1^{st}$ domain (FIG. 14A): performing a restriction digest of the domain sequence of step (b) with a restriction enzyme targeting the restriction site at the 3'-end and performing a restriction digest of the domain sequences of any of steps (c) to (e) with restriction enzymes targeting the restriction sites at the 5'-ends, (ii) in case of 3'-end labelling of the $1^{st}$ domain (FIG. 14B): performing a restriction digest of the domain sequence of step (b) with a restriction enzyme targeting the restriction site at the 5'-end and performing a restriction digest of the domain sequences of any of steps (c) to (e) with restriction enzymes targeting the restriction sites at the 3'-ends.

Furthermore, according to the second aspect of the invention, the claimed methods further comprise performing a further restriction digest on the bound ligation product as follows:

(i) in case of 5'-end labelling of the $1^{st}$ domain: performing a restriction digest of the bound ligation product with a restriction enzyme targeting the 3'-end of the domain ligated to the bound ligation product, (ii) in case of 3'-end labelling of the $1^{st}$ domain: performing a restriction digest of the bound ligation product with a restriction enzyme targeting the 5'-end of the domain ligated to the bound ligation product.

DETAILED DESCRIPTION OF THE INVENTION

The foregoing has outlined the features of various embodiments in order that the detailed description that follows may be better understood. Additional features and advantages of various embodiments will be described hereinafter which form the subject of the claims of the invention.

The prior art describes lytic chimeric polypeptides, which may comprise a CBD and an EAD. WO 2010/020657 describes the combination of different fragments of polypeptides from different wild-type enzymes into new chimeric polypeptide constructs ("shuffling"). As mentioned therein, the fragments are combined by molecular biological methods on the nucleic acid level. There are several differences between WO 2010/020657 and the novel methods of the present invention. In particular, in contrast to WO 2010/020657 the methods of the present invention comprise the use of a solid support. This provides for an improvement of the efficiency and accuracy of the methods of generating and screening for a chimeric polypeptide according to the present invention. In addition, the use of a solid support provides for accelerating the generation of novel chimeric polypeptides. Furthermore, the methods of the present invention follow a cyclic process, which has the effect that only those constructs are formed that have the desired length, i.e., chimeric polypeptides having, for example, 3 or 4 domains. In connection with this it is of note that the constructs as such are not generated in a directed manner. That is, the sequence (i.e., chronological order) of the domains in the chimeric polypeptides obtained from the methods is not predetermined (combinatorial approach). Here, the approach followed in the prior art, in particular in WO 2010/020657, is completely different. In particular, in the chimeric polypeptides generated in the prior art the domains are predetermined (directed cloning approach), and the domains used in the cloning methods were known domains having specific favourable characteristics and advantageous properties/activities. This is not surprising given that it was desired in the prior art to combine EADs, which were known for their favourable lytic activity. In other words, the prior art was following the principle of considering which combination of known fully characterized domains may be desirous. In contrast, the domains applied in the methods of the present invention are independent of any such previous knowledge, even though of course known domain sequences may be applied to the methods of the present invention. However, basically there is no prior knowledge necessary with respect to the characteristics, the relative positions, and activities/properties of the domains applied in the methods of the present invention. The chimeric polypeptides obtained from the methods of the present invention are characterized using the lytic activity of the resulting constructs. Therefore, the claimed methods allow selecting those variants, which have desired superior properties. This approach followed by the methods of the present invention is a hypothesis-free approach (discovery-driven). There is no need to identify and characterize the domain sequences prior to conducting the methods of the present invention. This is in clear contrast to the prior art methods. The prior art neither teaches nor suggest or foreshadows the approach that is underlying the methods of the present invention.

In essence, the methods of the present invention allow generating and screening for improved domain combinations that could not have been expected from considering the single domains in isolation. This effectiveness of the claimed methods has been demonstrated in the examples of the present application (Examples 5 and 6). Therefore, the present application provides evidence for the quality of the claimed methods. There is no method whatsoever in the prior art that would generate results similar to those achieved with the methods of the present invention.

In addition, the following Table shows the number of variants that can be obtained with the methods of the present invention:

| Number of DNA sequences (domains) | possible 2-domain variants | possible 3-domain variants | possible 4-domain variants | Total |
|---|---|---|---|---|
| 5 | 25 | 125 | 625 | 775 |
| 10 | 100 | 1000 | 10000 | 11100 |
| 20 | 400 | 8000 | 160000 | 168400 |
| 25 | 625 | 15625 | 390625 | 406875 |

Therefore, the methods of the present invention provide for a rapid and accurate generation of all variants resulting from a specific number of DNA sequences applied to the methods.

Enormous time-consuming, laborious efforts are required if all possible variants would have to be generated using conventional cloning methods.

Furthermore, the methods of the present invention have the effect that undesired by-products are eliminated during the method steps, thereby providing for a high efficiency of the methods and improving the likelihood that all possible variants are present in the resulting library.

In the present invention, the term "CBD" represents the abbreviation for cell binding domain, more specifically cell wall binding domain. Thus, the term "CBD" may also represent the abbreviation for cell wall binding domain. The terms "cell binding domain" and "cell wall binding domain" may be used interchangeably. The structural and functional definition of a CBD according to the present invention is given elsewhere in the description. In the present invention, "EAD" represents the abbreviation for enzymatic active domain. In the present invention, an EAD has lytic activity against bacteria. Thus, an EAD in accordance with the present invention can also be considered as a lytic domain. A more specific structural and functional definition of an EAD according to the present invention is given elsewhere here in the description. EADs in accordance with the present invention can be isolated from nature or can be produced by recombinant or synthetic means.

In the literature, the terms "bacteriophage lysins", "phage endolysins", "endolysins", "virolysins" and "lysins" are often interchangeably used. Thus, in the present invention, the terms "bacteriophage lysins", "phage endolysins", "endolysins" and "lysins" can be used interchangeably while defining the same kind of enzymes, namely bacterial cell wall-hydrolyzing enzymes synthesized during the late phase of gene expression in the lytic cycle of phage multiplication. By way of another definition, endolysin are enzymes encoded by double stranded (ds) DNA phage genomes that lyse bacterial cell walls. In general, in the present invention the term "bacteriophage" or "phage" means "lytic bacteriophage" or "lysogenic bacteriophage" ("lytic phage" or "lysogenic phage").

A "phage" or "bacteriophage", as used herein, relates to the well-known category of viruses that infect bacteria. Phages include DNA or RNA sequences encapsidated in a protein envelope or coat ("capsid").

In the present invention, the term "bacterium" preferably describes a "target bacterium", and refers to a bacterium that is bound by a chimeric polypeptide of the present invention and and/or whose growth, survival, or replication is inhibited by the enzymatic activity of an EAD in accordance with the present invention. Such a bacterium in accordance with the present invention is preferably a pathogenic bacterium. The inhibition of bacterial growth refers to the slowing or stopping of the rate of a bacteria cell's division or cessation of bacterial cell division, or to death of bacteria. The term "target bacterium" specifically includes both Gram-positive and Gram-negative target bacteria, preferably Gram-positive bacteria.

In the present invention, a polypeptide obtainable by the claimed methods is chimeric because it comprises a combination of domains selected from CBDs and EADs, which is as such not found in nature. Preferably, the domains combined in a chimeric polypeptide obtainable by the methods of the present invention are of different source or origin. Thus, a chimeric polypeptide obtainable by the methods of the present invention may comprise a CBD and an EAD from the same source or origin, provided that the chimeric polypeptide comprises at least one further CBD and/or EAD from a different source or origin.

Furthermore, a chimeric polypeptide obtainable by the methods of the present invention may comprise a CBD and an EAD from the same source or origin if the combination of domains from the same source or origin is as such not found in nature. In the present invention, the term "heterologous" may be used interchangeably with the term "chimeric".

In the present invention, the term "domain(s) of different source or origin" includes "domain(s) of a different source or origin of organism" and "domain(s) of a different source or origin of enzyme".

A chimeric polypeptide obtainable by the methods of the present invention may comprise more than one EAD and, thus, can act on different cell wall structures, and hence has the potential to treat two or more different bacterial infections at the same time.

In the present invention, a pathogenic bacterial species is defined by the similarities found among its members. Properties such as biochemical reactions, chemical composition, cellular structures, genetic characteristics, and immunological features are used in defining a pathogenic bacterial species and thus differentiating different pathogenic bacterial species.

An EAD in accordance with the present invention exhibits lytic activity against a bacterial cell. Thus, an EAD in accordance with the present invention exhibits the activity of inhibition of bacterial growth, including the slowing or stopping of the rate of cell division of bacteria or cessation of bacterial cell division, or to death of bacteria (killing colonizing bacteria).

In various embodiments of the present invention, the EAD is the lytic domain of a bacteriophage endolysin, including bacteriophage endolysins against Gram-positive and Gram-negative bacteria. More preferably, the EAD is the lytic domain of a bacteriophage endolysin, wherein the endolysin is from a bacteriophage that infects a Gram-positive bacterium. In various embodiments the EAD is the lytic domain of a bacteriophage endolysin, wherein the endolysin is from a bacteriophage that infects a Gram-negative bacterium.

As mentioned before, in the present invention bacteriophage lysins (or lysins) are bacterial cell wall-hydrolyzing enzymes synthesized during the late phase of gene expression in the lytic cycle of phage multiplication. As peptidoglycan is the major structural component of bacterial cell walls, in the present invention bacteriophage lysins are preferably peptidoglycan-hydrolysing enzymes. More preferably, in the present invention a bacteriophage lysine is a glycosidase, amidase, or endopeptidase, depending on the type of chemical bond they cleave within the peptidoglycan. Still more preferably, a bacteriophage lysine to be used in the present invention exhibits muramidase activity, glucosaminidase activity, or transglycosylase activity. Thus, in the present invention, a bacteriophage lysine provides at least one of the following enzymatic activities against a peptidoglycan substrate: muramidase activity, glucosaminidase activity, N-acetylmuramyl-L-alanine amidase activity and endopeptidase activity.

By way of another definition, bacteriophage endolysin are enzymes encoded by double stranded (ds) DNA phage genomes that lyse bacterial cell walls. This definition of bacteriophage endolysins is encompassed by the present invention, too.

In various embodiments of the present invention, the EAD is the lytic domain of a bacteriocin, including the lytic domain of a bacteriocin from Gram-positive and Gram-negative bacteria. Preferably, the EAD is the lytic domain of a bacteriocin from a Gram-positive bacterium. In various embodiments, the EAD is the lytic domain of a bacteriocin from a Gram-negative bacterium.

In various embodiments of the present invention, the EAD is the lytic domain of a bacterial autolysin, including autolyins from both Gram-positive and Gram-negative bacteria.

Preferably, the EAD is the lytic domain of an autolysin from a Gram-positive bacterium. In various embodiments, the EAD is the lytic domain of an autolysin from a Gram-negative bacterium.

Bacteriophages are not only known to encode and produce lysins, but also so-called tail associated muralytic enzymes (TAMEs), which are likewise capable of hydrolysing bacterial cell walls. While lysins are produced in the final stage of the phage-life cycle to facilitate the release of progeny phage from the host bacterium, TAMEs are, in contrast, structural proteins necessary during the first stage of the process of infection of a host cell. The first stage of the phage infection process comprises the steps of adsorption to and penetration of the host cell, which is mediated using, inter alia, the TAME. Many but not all phages have tails attached to the phage head. Thus, in various embodiments of the present invention, the EAD is a bacteriophage tail-associated protein having lytic activity. Preferably, the EAD is a tail-associated protein having lytic activity of phages that infect Gram-positive hosts. In various embodiments, the EAD is a tail-associated protein having lytic activity of phages that infect Gram-negative hosts. Bacteriophage tail-associated proteins typically mediate the recognition and attachment of the phage to the target host, and some of them possess cell wall degrading activities, which assist in penetration of phage components into the host.

In various embodiments of the present invention, the EAD is derived from bacteriophage tail-equivalents in caudovirales, which provide means for the phage to enter a bacterial host from the external environment.

A chimeric polypeptide obtainable by the methods of the present invention may comprise more than one CBD and, thus, can bind to different cell wall structures, and hence has the potential to treat two or more different bacterial infections at the same time.

In the present invention, any kind of CBD can be used in the methods of the present invention and includes cell-binding domains, which are part of proteins binding to a target bacterial cell, specifically to the cell wall of a target bacterium. Thus, in the present invention, the CBDs are specifically cell wall-binding domains. In general, a CBD in accordance with the present invention binds to bacterial cells, specifically to cell walls of target bacteria, more specifically to cell wall components produced by a target cell, which are non-covalently or covalently associated with the cell wall of a target cell. In other words, the cell-binding domain or cell wall-binding domain is that part of a cell binding protein or cell wall binding protein, which is necessary and sufficient for the binding ability to a bacterial cell or target bacterial cell, specifically for the binding ability to the cell surface of a bacterial cell or target bacterial cell. The bacterial cell or target bacterial cell includes any Gram-positive or Gram-negative bacterial cell.

In various preferred embodiments of the present invention, the CBD is the cell-binding domain of a bacteriophage endolysin, including bacteriophage endolysins against Gram-positive and Gram-negative bacteria. More preferably, the CBD is the cell-binding domain of a bacteriophage endolysin, wherein the endolysin is from a bacteriophage that infects a Gram-positive bacterium. In various embodiments the CBD is the cell-binding domain of a bacteriophage endolysin, wherein the endolysin is from a bacteriophage that infects a Gram-negative bacterium.

In various preferred embodiments of the present invention, the CBD is the cell-binding domain of a bacteriocin, including the cell-binding domain of a bacteriocin from Gram-positive and Gram-negative bacteria. Preferably, the CBD is the cell-binding domain of a bacteriocin from a Gram-positive bacterium. In various embodiments, the CBD is the cell-binding domain of a bacteriocin from a Gram-negative bacterium.

In various preferred embodiments of the present invention, the CBD is the cell-binding domain of a bacterial autolysin, including autolysins from both Gram-positive and Gram-negative bacteria. Preferably, the CBD is the cell-binding domain of an autolysin from a Gram-positive bacterium. In various embodiments, the CBD is the cell-binding domain of an autolysin from a Gram-negative bacterium.

CBDs to be used in the methods of the present invention are capable of specifically binding to bacteria. Thus, while CBDs in accordance with the present invention exhibit cell binding activity, they have no or no significant hydrolytic activity. No or no significant hydrolytic activity in this context is intended to describe the situation whereby the hydrolytic activity is not sufficient to prevent the application of a CBD to bind to a bacterial cell, more specifically to a bacterial cell wall. A CBD to be used in the methods of the present invention is supposed to be a protein, which does not have any hydrolytic activity itself. This also applies to fragments and variants of a CBD according to the present invention, which are also encompassed by the present invention.

The present invention encompasses DNA sequences of any known CBDs and EADs. In the present invention, also DNA sequences coding for functional fragments of known CBDs and EADs as well as DNA sequences coding for mutants and variants of known CBDs and EADs having the same biological function or activity as the known reference CBD or EAD may be used in the methods of the present invention, i.e. binding to the cell wall of a bacterial cell and exhibiting the activity of hydrolysing a bacterial cell wall, respectively.

As used herein, the terms "functional fragment", "mutant" and "variant" refer to a polypeptide, which possesses biological function or activity identified through a defined functional assay and associated with a particular biologic, morphologic, or phenotypic alteration in a bacterial cell or of a bacterial cell. EADs and CBDs in accordance with the present invention specifically also encompass naturally occurring forms like, for example, alternatively spliced or modified forms and naturally-occurring variants thereof, the DNA sequences coding for which can be used in the methods of the present invention.

The DNA sequences encoding fragments and variants of CBDs and EADs that can be used in the methods of the present invention include chemically synthesized DNA sequences (synthetic genes).

Modifications of CBDs and EADs in accordance with the present invention may result in mutant or variant proteins having substantially equivalent activity to a reference CBD or EAD described herein. Such modifications may be deliberate, as by site-directed mutagenesis, or may occur by spontaneous changes in nucleotide and amino acid sequences where these changes produce modified polypeptides having substantially equivalent activity to the respective reference CBD or EAD. Any polypeptides produced by minor modifications of a known CBD or EAD primary amino acid sequence are included herein as long as the biological activity of a cell wall binding domain or an enzymatic active domain exhibiting lytic activity is present. DNA sequences encoding such modified CBD and EAD polypeptides may also be used in the methods according to the present invention.

As used herein, "substantially equivalent activity" refers to polypeptides, wherein changes in one or more nucleotide bases of the respective nucleotide sequence encoding the polypeptide result in substitution of one or more amino acids, but do not affect the functional properties of the polypeptide encoded by the nucleotide sequence. "Substantially equivalent activity" also refers to modifications of CBD and/or EAD encoding nucleic acid sequences such as deletion or insertion that do not substantially affect the functional properties of the resulting transcript and/or protein. It is therefore understood that in the methods according to the present invention more than the nucleotide or amino acid sequences of known CBDs and EADs can be used, i.e. including functional equivalents thereof.

CBDs and EADs for use in the present invention may be identified by analysis of genome sequences using the NCBI website (world wide web at ncbi.nlm.nih.gov); specifically, ORF Finder at the NCBI website may be used for identification (world wide web at ncbi.nlm.nih.gov/gorf/gorf.html). Sequences of predicted proteins can be scanned for homology with known proteins using BLAST searches via the NCBI website (world wide web at ncbi.nlm.nih.gov/BLAST). Multiple sequence alignments of homologous genes and proteins can be performed using ClustalW at the EBI website (world wide web at ebi.ac.uk/Tools/clustalw2/index.html).

In particular, with respect to endolysins the skilled person is in the position to identify CBDs and EADs by homology search in the genome of bacteria and bacterial phages and/or functional screening of DNA libraries of phage genomes. Such homology searches may not only target lysine genes, but also the corresponding holin genes as the holin and lysine happen to be encoded adjacently in a particular genome. By targeting holing genes, it is thus possible to identify adjacent lysins. In addition, bacteriophage endolysin CBDs and EADs may be identified experimentally as described, for example, in Loessner et al. 2002 and Korndorfer et al. 2006, i.e. by determining the domain structure of an endolysin and elucidating the cell wall binding and lytic function of the respective domains. Bacteriophage lysins to be analyzed for CBDs and EADs may be identified by the method described in Schuch et al. 2009. As mentioned therein, the techniques described can be adapted to identify lysins from any phage infecting Gram-positive or even Gram-negative bacteria. Furthermore, endolysin CBDs and EADs may be identified using DNA libraries as described in Schmitz et al. 2008.

Likewise, with respect to autolysins and bacteriocins, the skilled person is in the position to identify CBDs and EADs by homology search in the genome of bacteria. CBDs and EADs of autolysins and bacteriocins may also be identified experimentally.

Basically, the methods according to the present invention are characterized by binding a first domain sequence, which may be a CBD or an EAD and which may be part of a ligation construct of two or more domain sequences selected from CBD and EAD sequences, to a solid support using a tag labelling of said first domain sequence to be bound to the solid support. Furthermore, the methods according to the present invention are basically characterized by ligating one or more domain sequences selected from CBD and EAD sequences to said first domain sequence when bound to the solid support and/or to a ligation construct of two or more domain sequences selected from CBD and EAD sequences, which is bound to the solid support phase by said first domain sequence being bound to the solid support. Thus, ligating one or more domain sequences selected from CBD and EAD sequences includes not only ligating one or more domain sequences selected from CBD and EAD sequences to a single first domain sequence originally bound to the solid support, but also ligating one or more domain sequences selected from CBD and EAD sequences to a ligation construct, which comprises two or more domain sequences and which was originally bound to the solid support by a first domain sequence. Thus, the ligation steps result in ligation products of one or more domain sequences selected from CBD and EAD sequences to a single first domain sequence bound to a solid support or one or more domain sequences selected from CBD and EAD sequences to a ligation construct of two or more domain sequences selected from CBD and EAD sequences, which was originally bound to the solid support by a first domain sequence. Still further, the methods according to the present invention are basically characterized by releasing the ligation product from the solid support after ligation of one or more domain sequences to said first domain sequence bound to the solid support and/or to the ligation construct, which was originally bound to the solid support phase by said first domain sequence being bound to the solid support. Thus, the step of releasing a ligation product from the solid support after performing one or more steps of ligation of one or more domain sequences selected from CBD and EAD sequences provides a DNA coding for a polypeptide, which can then be proven as a lytic chimeric polypeptide in accordance with the present invention.

Accordingly, the present invention provides methods of generating and screening for a chimeric polypeptide comprising at least one CBD and at least one EAD comprising the steps of (i) binding a first domain sequence, which may be a CBD or an EAD and which may be part of a ligation construct of two or more domain sequences selected from CBD and EAD sequences, to a solid support using a tag labelling of the domain sequence to be bound to the solid support, (ii) ligating one or more domain sequences selected from CBD and EAD sequences to said first domain sequence bound to the solid support and/or to said ligation construct comprising one or more domain sequences selected from CBD and EAD sequences, which is bound to the solid support phase by said first domain sequence bound to the solid support, and (iii) releasing from the solid support the ligation product resulting from ligation of one or more domain sequences to the first domain sequence bound to the solid support and/or resulting from ligation of one or more domain sequences to said ligation construct, which was originally bound to the solid support phase by the said first domain sequence bound to the solid support.

In the present invention, one or more domain sequences selected from CBD and EAD sequences are bound to the solid support as a first domain sequence by tag labelling. Thus, a non-limited number of different so-called first domain sequences are bound to the solid support, and to each of which one or more domain sequences selected from CBD and EAD sequences may be ligated. This allows providing a non-limited number of ligation products corresponding to all combinations of CBDs and EADs, which are statistically possible depending on the CBD and EAD sequences applied and the ligation cycles performed, and which are as such not found in nature.

The situation described above accordingly holds for constructs of two or more domain sequences selected from CBD and EAD sequences, which are bound to the solid support phase. That is, in various embodiments of the present invention a non-limited number of constructs of one or more domain sequences selected from CBD and EAD sequences may be bound to the solid support by the first domain sequence carrying a tag labelling. Thus, to each of the originally bound ligation constructs of two or more domain sequences selected from CBD and EAD sequences, one or more domain sequences selected from CBD and EAD sequences may be ligated. This allows providing a non-limited number of ligation products corresponding to all combinations of CBDs and EADs, which are statistically possible depending on the CBD and EAD sequences applied and the ligation cycles performed, and which are as such not found in nature.

More specifically, the methods of the present invention may provide for a non-limited number of ligation products corresponding to all combinations of CBDs and EADs from the different sources or origins described herein. Thus, the generation and screening for lytic chimeric polypeptides provided by the present invention is based on a random shuffling of domain sequences selected from CBD and EAD sequences using a solid support, on which a non-limited number of ligation products of two or more domain sequences selected from CBD and EAD sequences is formed. Thus, the number of first domain sequences and/or ligation constructs of two or more domain sequences selected from CBD and EAD sequences, which are originally to be bound to the solid support in order to form ligation products by repeatedly performing ligation steps on said first domain sequence(s) and/or ligation construct(s), is non-limited and includes even the binding of only one such first domain sequence and/or only one such ligation construct to the solid support.

In accordance with the present invention, the domain sequence originally bound to the solid support or that domain sequence of a ligation construct, which is directly bound to the solid support via tag labelling, is called the $1^{st}$ domain sequence. Furthermore, in accordance with the present invention the ligation construct of two or more domain sequences selected from CBD and EAD sequences, which is originally bound to the solid support via tag labelling of the first domain sequence of such a ligation construct, may also be called a first ligation product.

In the present invention, a solid support having bound first domain sequences and/or ligation constructs of two or more domain sequences selected from CBD and EAD sequences may be called solid support phase. Thus, in the present invention ligating domain sequences to first domain sequences and/or ligation constructs bound to a solid support may also be described as ligating domain sequences to the solid support phase.

In various embodiments, the methods according to the present invention are characterized by the step of providing one or more DNA sequences each encoding at least one CBD, and furthermore one or more DNA sequences each encoding at least one EAD, wherein the EAD is selected from the group consisting of (i) the lytic domain of a bacteriophage lysin, (ii) the lytic domain of a bacteriocin, (iii) the lytic domain of a bacterial autolysin; and (iv) a bacteriophage tail-associated protein having lytic activity. Optionally, step (a) of the methods according to the present invention furthermore provides one or more DNA sequences, wherein each sequence encodes at least one CBD and at least one EAD, wherein the EAD is selected from the group consisting of (i) the lytic domain of a bacteriophage lysin, (ii) the lytic domain of a bacteriocin, (iii) the lytic domain of a bacterial autolysin; and (iv) a bacteriophage tail-associated protein having lytic activity. Thus, while in step (a) basically each of the DNA sequences (one or more) encodes either at least one CBD or at least one EAD, optionally step (a) furthermore includes providing one or more DNA sequences, wherein each DNA sequence encodes both at least one CBD and at least one EAD.

In the present invention, the generation of ligatable, position-specific PCR fragments (see Example 2) may be performed in two ways: either with a primer which is not tag-labelled (i.e., for example, a non-biotinylated primer) or with a primer which is tag-labelled (i.e., for example, a biotinylated primer). PCR products for domain sequences, which are generated with a primer that is not tag-labelled, as well as PCR products for the first domain sequence ("position 1") generated with a primer that is tag-labelled, are to be purified using common purification kits. PCR products for domain sequences except for first domain sequences generated with a primer that is tag-labelled (with, for example, a biotin-tag) may be purified by correspondingly prepared magnetic particles. That is, in case of using the biotin-streptavidin-system, such PCR products may be purified by streptavidin-coated magnetic particles. In particular, PCR products are bound to beads, which are subsequently washed for applying an appropriate buffer or change of buffer and released from the beads by restriction digest at restriction sites previously introduced into the domain sequence. PCR products for first domain sequences generated with a primer that is tag-labelled may not be purified by magnetic particles together with the use of a restriction enzyme because this would remove the tag-labelling from the first domain sequence, which is however required for binding of first domain sequences to a solid support.

In the present invention, the amplification of the domain sequences follows standard procedures using PCR and position-specific primers. Alternatively, domain sequences may be obtained from plasmid preparations, i.e. for the ligation reaction a multiple of domain sequences can be prepared by restriction digest from plasmids, which carry the domain sequences and which are cultured in appropriate hosts for "amplification" of the plasmids. In the present invention, binding of ligation products to a solid support is performed using a tag labelling, preferably a biotin tag labelling. Various peptide tags have become popular in biotechnology, among them those essentially enabling reversible immobilization of proteins to affinity matrices.

In the present invention, the introduction of a tag labelling at the 5'-end or 3'-end of a domain DNA sequence can be performed using standard labelling systems involving the use of, for example, 5'- and 3'-biotinylated primers, respectively. In various embodiments, the tag labelling may be introduced not directly at the 5'-end, but at a base position located more downstream in the 3'-end direction, provided that the tag labelling may still be removed by restriction enzyme digest. In the present invention, a tag labelling is a labelling which provides for a binding of a nucleic acid sequence to a solid support such as a particle, a surface of a device, a foil or a fleece, more specifically a silica bead or an organic polymer bead, which may be magnetic. Thus, in various embodiments of the present invention a tag labelling provides for a chemical tag labelling, e.g. a biotin labelling or a digoxigenin labelling. In various embodiments, the biotin-streptavidin-system is a preferred system to be used in the methods according to the present invention, wherein the binding of a domain sequence, specifically a first domain sequence in accordance with the present invention, or a ligation construct of two or more domain sequences selected from CBD and EAD sequences to a solid support is mediated by streptavidin. In various other embodiments, the digoxigenin-antibody-system is a preferred system to be used in the methods according to the present invention, wherein the binding of a domain sequence, specifically a first domain sequence in accordance with the present invention, or a ligation construct of two or more domain sequences selected from CBD and EAD sequences to a solid support is mediated by an antibody.

In various embodiments of the methods of the present invention, the first domain to be ligated to the solid support may be a nonsense-domain, which is carrying a tag labelling and which may be detached after performing the ligation step(s) ligating EAD and CBD domains to the solid support phase, i.e. in accordance with the step of releasing the obtained ligation product from the solid support.

In the present invention, restriction digests with restriction enzymes are performed by standard procedures and according to the manual of the manufacturer of the respective restriction enzyme.

In the present invention, ligation of domain sequences follows standard procedures. In various embodiments, ligation of the $1^{st}$ and $2^{nd}$ domain sequence is performed in ligase buffer while ligation of the ligated $1^{st}$ and $2^{nd}$ domain with one or more further domain sequences is performed in restriction enzyme buffer of the respective restriction enzyme(s) under addition of ATP. In various embodiments, ligation of domains to the solid phase, i.e. ligation of domains to the solid support having bound already a ligation product, is performed using bound and free domains in a ratio of 1:5, preferably 1:10. In various embodiments, the ratio of bound and free domains is 1:15, more preferably 1:20.

In the methods of the present invention, the domain sequences may be ligated to the solid support phase after a restriction digest has been performed on each of the amplified domain sequences with the appropriate restriction enzyme targeting the restriction site previously introduced into the respective domain sequences in accordance with the present invention. Alternatively, the domain sequences may be ligated to the solid support phase with only that end of the domain sequence being digested with a corresponding restriction enzyme, which is ligated to the preceding domain sequence on the solid support phase. Depending on the orientation of the growing ligation product, i.e. depending on the tag labelling of the first domain sequence being either at the 5'-end or at the 3'-end, the digested end of the domain sequence to be ligated may either be the 3'-end or the 5'-end. In this situation, a restriction digest is performed on the solid support phase, i.e., in particular, on the growing ligation product, using the appropriate restriction enzyme targeting the restriction site introduced into the most recent ligated domain sequence in order to prepare the non-ligated end of the most recent ligated domain sequence for being ligated with a further domain sequence. This alternative way of step-by-step restriction digest and ligation of a domain sequence is preferably applicable in the situation where the ligatable domain sequences are amplified using a primer which is tag-labelled (i.e., for example, a biotinylated primer). Accordingly, the resulting PCR products may be purified by correspondingly prepared magnetic particles and the PCR products are released from the beads by restriction digest, which is performed at that restriction site previously introduced into the domain sequence to be amplified, which is required for ligating the domain sequence to the growing ligation product on the solid support phase. This approach does not require performing a restriction digest on the other restriction site previously introduced at the other end (either 5' or 3') of the domain sequence to be amplified. As described above, a restriction digest on this restriction site is then performed after the domain sequence has been ligated to the solid support phase. In various embodiments of the present invention, the step of releasing the ligation product or ligation products from the solid support is carried out using a restriction enzyme targeting the restriction site at that end of the $1^{st}$ domain, which is carrying the tag labelling. In various other embodiments of the present invention, the step of releasing the ligation product or ligation products from the solid support is carried out by releasing the bound tag from the solid support. In this case, the ligation product together with the tag labelling is released from the solid support. Thus, when using, for example, the biotin-streptavidin system in the methods of the present invention, this means disruption of the streptavidin-biotin bond under appropriate conditions. Where the step of releasing the ligation product from the solid support is carried out by releasing the bound tag from the solid support, subsequent cloning of the released ligation product into an expression vector requires a restriction digest of the ligation product with the respective restriction enzyme targeting the restriction site at that end of the $1^{st}$ domain of the ligation product, which is carrying the tag labelling.

In the present invention, introducing the expression vector carrying the ligation product released from the solid support into an expression host can be performed by methods described in standard laboratory manuals, and includes standard transformation procedures like, for example, electroporation or the use of chemically competent cells.

In the present invention, the expression host, into which the expression vector carrying the ligation product is introduced, includes any host-based system, which allows expression of the ligation product released from the solid support. Host cells can be genetically engineered to incorporate expression systems or portions thereof. Representative examples of appropriate hosts include bacterial cells, such as streptococci, staphylococci, enterococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells and plant cells.

In the present invention, the expression host is preferably a bacterial expression strain. More preferably, the bacterial expression strain is an inducible bacterial expression strain like, for example, the T5 or T7-expression strains. In general, expression hosts and expression vectors (plasmids) that can be used in the present invention are known to the person skilled in the art.

Expression vectors to be used in the present invention provide for or are designed to allow cloning of the ligation product obtained from the solid support by appropriate restriction enzyme sites. The expression system constructs to be used in the present invention may contain control regions that regulate as well as engender expression. Generally, any system or vector suitable to express ligation products and chimeric polypeptides according to the present invention may be used for expression in this regard. The appropriate sequences may be inserted into the expression system by any of a variety of well-known and routine techniques.

In various embodiments, the restriction vector carries an appropriate selection marker like, for example, an ampicillin resistance gene.

In the present invention, selecting an expression clone expressing a lytic chimeric polypeptide encoded by the domain sequences of a ligation product obtained from the solid support includes, but is not limited to, picking single colonies forming a lytic halo on agar plates comprising, for example, *Listeria* cells. Such colonies are transformants carrying an expression vector with a ligation product and expressing a polypeptide, which is lytic to said *Listeria* cells. The single colonies can be isolated by, for example, picking and culturing on appropriate back-up agar plates. An appropriate back-up agar plate comprises an antibiotic in accordance with the expression vector carrying the ligation product obtained from the solid support.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of the invention.

In the present invention, characterizing and identifying a polypeptide obtainable by the methods of the present invention as a lytic polypeptide includes, but is not limited to, testing selected clones for their lytic activity against several bacterial strains, i.e., for example, against different *Listeria* serovars. Thus, a lytic polypeptide obtainable by the methods of the present invention can be characterized for its lytic activity against one or more bacterial strains.

In the present invention, characterizing and identifying a polypeptide obtainable by the methods of the present invention as a lytic polypeptide also includes, but is not limited to, sequencing of the clones showing lytic activity against bacterial strains, i.e. identifying the sequence of the lytic polypeptide encoded by the plasmid carrying the ligation product obtained in the methods of the present invention.

In the present invention, characterizing and identifying a polypeptide obtainable by the methods of the present invention as a lytic polypeptide furthermore includes, but is not limited to, performing tests on expression of the lytic polypeptide encoded by the plasmid carrying the ligation product obtained in the methods of the present invention.

In the present invention, removing non-ligated domain sequences after performing the steps of ligating domains to the solid support phase includes, but is not limited to, washing the solid support phase using an appropriate washing buffer for washing away non-ligated domain sequences. Thus, in the present invention the step of removing non-ligated domain sequences after a ligation step is preferably a washing step. The same holds for the step of removing unbound domain sequences after binding first domain sequences and/or ligation constructs according to the present invention to a solid support.

In general, the methods according to the present invention may comprise one or more washing steps after each step of binding of a first domain sequence or a ligation construct of two or more domain sequences selected from CBD and EAD sequences to a solid support. The same applies to each step of ligating domain sequences to a first domain sequence and/or to a ligation construct of two or more domain sequences selected from CBD and EAD sequences, which are originally bound to the solid support in order to form ligation products by repeatedly performing ligation steps on said first domain sequence(s) and/or said ligation construct (s). As used herein, the washing steps provide for changing buffers, which may become necessary due to, for example, different restriction enzymes to be used when performing the ligation steps of the methods of the present invention. Similarly, a washing step may become necessary between the steps of binding of a first domain sequence or a ligation construct of two or more domain sequences selected from CBD and EAD sequences to a solid support and the subsequent ligation steps. In addition, one or more washing steps may become necessary after performing a restriction digest on the solid support phase as described herein above, i.e., a restriction digest performed on the growing ligation product. Such washing steps may not only become necessary for changing buffers, in particular restriction enzyme buffers, but may also be performed in order to remove, i.e. washing away, undesired products resulting from the restriction digest. Accordingly, such washing steps as described before may be performed after any step of performing a restriction digest in the present invention.

As will be understood by the one of skilled in the art, the method of generating a chimeric polypeptide having at least one CBD and at least one EAD according to the present invention (cf. item [2] under "Summary of the Invention") may furthermore comprise a step of cloning the ligation product obtained in step (l) into a cloning vector prior to characterizing the obtained ligation products. The characterization of a polypeptide obtainable by said method as a chimeric polypeptide in accordance with the present invention includes, but is not limited to, sequencing of the ligation products obtained and thus elucidating the CBD and EAD domain structures. Furthermore, characterization of a polypeptide obtainable by said method as a chimeric polypeptide in accordance with the present invention may be done by testing the polypeptide for its cell wall binding and lytic activity against several bacterial strains, for example, against different *Listeria* serovars.

In the present invention, the terms "protein" and "peptide" may be used interchangeably with the term "enzyme". In other words, a "lytic chimeric polypeptide" obtainable by the methods of the present invention is a polypeptide, which comprises one or more heterologous domains exhibiting lytic activity on pathogenic bacterial cells.

In various embodiments of the present invention, the methods further comprise a step of selecting expression hosts carrying the expression vector with the ligation product cloned therein prior to culturing the expression host under conditions suitable to allow expression of a lytic polypeptide encoded by the domain sequences of the cloned ligation product.

Figure 1:
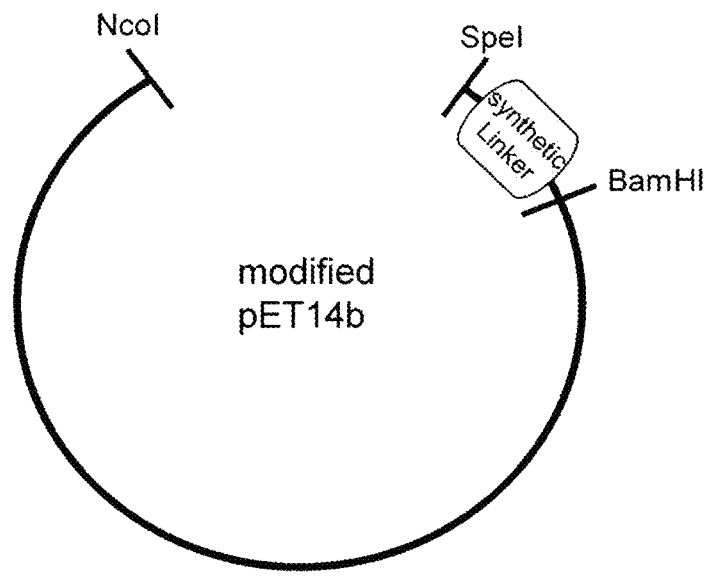
FIG. 1 shows a scheme of the modified cloning vector pET14b. The 5' end of the insert will be ligated to the NcoI site, the 3' end of the insert will be ligated to the SpeI site of the vector. Downstream of the SpeI site lies the sequence for the synthetic linker. For the insert carries no stop codon the translation will include the synthetic linker and a stop at a vector intrinsic codon behind the BamHI-site.

In various embodiments of the present invention, the domain sequences are joined (linked) by a linker sequence, which is a native or a synthetic linker sequence. In various embodiments of the present invention, the "linker sequence" refers to an amino acid sequence that joins two domain sequences of a lytic chimeric polypeptide of the present invention or fragments or variants thereof. In general, as used herein, a linker includes, but is not limited to, an amino acid sequence that covalently links the domains of the lytic chimeric polypeptide obtainable by the present invention. More specifically, the linker comprises at least one peptide bond. As appreciated by one of skill in the art, the linker can comprise additional amino acids. In general, a linker sequence or domain linker as used in the present invention denotes an amino acid sequence functioning to connect single domain sequences with each other. Properties of linker sequences or domain linkers in accordance with the present invention as well as methods to detect those are known to the person skilled in the art. In the present invention, a linker sequence may be incorporated into a chimeric polypeptide obtainable by the methods of the present invention if it is part of a cloning vector as exemplarily shown in FIG. 1. While FIG. 1 shows exemplarily a synthetic linker, the linker of the cloning vector may also be a native linker cloned into the cloning vector. Alternatively, a native linker may be incorporated into a chimeric polypeptide obtainable by the methods of the present invention if a selected domain sequence is isolated together with its native linker sequence. Furthermore, a linker sequence may be incorporated into a chimeric polypeptide obtainable by the methods of the present invention by means of PCR applied in various steps of the methods of the present invention.

The methods for generating a chimeric polypeptide having at least one CBD and at least one EAD according to the present invention provide for a plurality of chimeric polypeptides.

The present invention also provides a DNA library comprising the clones carrying the ligation products obtained in the methods according to the present invention.

Based on comparative test methods available in the art (see, for example, Kusuma and Kokai-Kun 2005), the person skilled in the art can easily determine whether a lytic chimeric polypeptide obtained by the methods of the present invention shows improved biological properties over lytic polypeptides known in the art. Improved biological properties means an improvement with respect to lower working concentration, higher stability, altered specificity and/or hydrolyzing activity on bacterial cell walls.

In various preferred embodiments, the methods of the present invention comprise amplifying the $1^{st}$, $2^{nd}$ and $3^{rd}$ domain sequences, and optionally amplifying one or more further domain sequences.

In various embodiments of the method for generating a chimeric polypeptide according to the first aspect of the invention, step (m), i.e. characterizing the ligation product obtained in step (l), comprises the steps of:

(m) cloning the ligation product obtained in step (l) into an expression vector;

(n) introducing the vector obtained in step (m) into an expression host, preferably into a bacterial expression host;

(o) culturing the expression host of step (n) carrying the vector obtained in step (m) under conditions suitable to allow expression of a lytic polypeptide encoded by the domain sequences of the cloned ligation product;

(p) selecting and isolating an expression clone expressing a lytic polypeptide according to step (o) using the lytic activity of the polypeptide; and (q) characterizing the lytic polypeptide expressed by the isolated expression clone of step (p) and identifying a lytic chimeric polypeptide having at least one CBD and at least one EAD.

In various embodiments of the method of screening for a lytic chimeric polypeptide and the method of generating a chimeric polypeptide according to the second aspect of the invention, steps (h) and (j) and steps (k) and (l) may be combined, as reflected in corresponding steps (h) and (j) of the following embodiments of the claimed methods according to the second aspect of the invention: 1". A method of screening for a lytic chimeric polypeptide comprising the steps of:

(a) providing one or more DNA sequences each encoding at least one cell binding domain (CBD) and one or more DNA sequences each encoding at least one enzymatic active domain (EAD) and optionally one or more DNA sequences each encoding at least one CBD and at least one EAD, wherein the EAD is selected from the group consisting of (i) the lytic domain of a bacteriophage lysin, (ii) the lytic domain of a bacteriocin, (iii) the lytic domain of a bacterial autolysin; and (iv) a bacteriophage tail-associated protein having lytic activity;

(b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second ($2^{nd}$) domain sequence selected from the domain sequences of (a) using a pair of primers designed to introduce:

(i) in case of 5'-end labelling of the $1^{st}$ domain: at the 5'-end the same restriction site as at the 3'-end of the $1^{st}$ domain, and at the 3'-end a restriction site different from the restriction sites introduced into the $1^{st}$ domain sequence, (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;

wherein the pair of primers is further designed such that the restriction sites are different at the 5'-end and the 3'-end of the $3^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;

wherein the pair of primers is further designed such that the restriction sites are different at the 5'-end and the 3'-end of each of said one or more further domain sequences;

(f) performing a restriction digest of the domain sequences of any of steps (b) to (e):

(i) in case of 5'-end labelling of the $1^{st}$ domain: performing a restriction digest of the domain sequence of step (b) with a restriction enzyme targeting the restriction site at the 3'-end and performing a restriction digest of the domain sequences of any of steps (c) to (e) with restriction enzymes targeting the restriction sites at the 5'-ends, (ii) in case of 3'-end labelling of the $1^{st}$ domain: performing a restriction digest of the domain sequence of step (b) with a restriction enzyme targeting the restriction site at the 5'-end and performing a restriction digest of the domain sequences of any of steps (c) to (e) with restriction enzymes targeting the restriction sites at the 3'-ends;

(g) ligating the digested $1^{st}$ and $2^{nd}$ domain sequence obtained in step (f) to obtain a ligation product comprising the $1^{st}$ and $2^{nd}$ domain sequence;

(h) binding the ligation product of step (g) to a solid support using the tag labeling of the $1^{st}$ domain sequence to obtain a bound ligation product comprising the $1^{st}$ and $2^{nd}$ domain sequence, and performing a restriction digest of said bound ligation product:

(i) in case of 5'-end labelling of the $1^{st}$ domain: performing a restriction digest of the bound ligation product with a restriction enzyme targeting the 3'-end of the $2^{nd}$ domain, (ii) in case of 3'-end labelling of the $1^{st}$ domain: performing a restriction digest of the bound ligation product with a restriction enzyme targeting the 5' end of the $2^{nd}$ domain;

(j) optionally ligating the digested $3^{rd}$ domain sequence of step (d) obtained in step (f) to the bound ligation product of step (h) to obtain a bound ligation product comprising the $1^{st}$, $2^{nd}$ and $3^{rd}$ domain sequence, and performing a restriction digest of said bound ligation product:

(i) in case of 5'-end labelling of the $1^{st}$ domain: performing a restriction digest of the bound ligation product with a restriction enzyme targeting the 3'-end of the $3^{rd}$ domain.

(ii) in case of 3'-end labelling of the $1^{st}$ domain: performing a restriction digest of the bound ligation product with a restriction enzyme targeting the 5'-end of the $3^{rd}$ domain.

(k) optionally ligating one or more digested domain sequences of (e) obtained in step (f) to the bound ligation product of step (j) to obtain a bound ligation product comprising one or more further domain sequences of step (e), thereby performing after each ligation step a restriction digest of the bound ligation product as follows:

(i) in case of 5'-end labelling of the $1^{st}$ domain: performing a restriction digest of the bound ligation product with a restriction enzyme targeting the 3'-end of the said further domain sequence that was ligated to the bound ligation product, (ii) in case of 3'-end labelling of the $1^{st}$ domain: performing a restriction digest of the bound ligation product with a restriction enzyme targeting the 5'-end of the said further domain sequence that was ligated to the bound ligation product;

(l) releasing the ligation product obtained in any of steps (h) to (k) from the solid support;

(m) cloning the ligation product obtained in step (l) into an expression vector;

(n) introducing the vector obtained in step (m) into an expression host, preferably into a bacterial expression host;

(o) culturing the expression host of step (n) carrying the vector obtained in step (m) under conditions suitable to allow expression of a lytic polypeptide encoded by the domain sequences of the cloned ligation product;

(p) selecting and isolating an expression clone expressing a lytic polypeptide according to step (o) using the lytic activity of the polypeptide; and (q) characterizing the lytic polypeptide expressed by the isolated expression clone of step (p) and identifying a lytic chimeric polypeptide.

2". A method of generating a chimeric polypeptide having at least one cell binding domain (CBD) and at least one enzymatic active domain (EAD), the method comprising the steps of:

(a) providing one or more DNA sequences each encoding at least one CBD and one or more DNA sequences each encoding at least one EAD, and optionally one or more DNA sequences each encoding at least one CBD and at least one EAD, wherein the EAD is selected from the group consisting of (i) the lytic domain of a bacteriophage lysin;

(ii) the lytic domain of a bacteriocin;

(iii) the lytic domain of a bacterial autolysin; and (iv) a bacteriophage tail-associated protein having lytic activity.

(b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;

(c) amplifying a second ($2^{nd}$) domain sequence selected from the domain sequences of (a) using a pair of primers designed to introduce:

(i) in case of 5'-end labelling of the $1^{st}$ domain: at the 5'-end the same restriction site as at the 3'-end of the first domain, and at the 3'-end a restriction site different from the restriction sites introduced into the $1^{st}$ domain sequence, (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;

(d) optionally amplifying a third ($3^{rd}$) domain sequence selected from the domain sequences of (a) using a pair of primers designed to introduce:

(i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;

wherein the pair of primers is further designed such that the restriction sites are different at the 5'-end and the 3'-end of the $3^{rd}$ domain sequence;

(e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:

(i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain, (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;

wherein the pair of primers is further designed such that the restriction sites are different at the 5'-end and the 3'-end of each of said one or more further domain sequences;

(f) performing a restriction digest of the domain sequences of any of steps (b) to (e):

(i) in case of 5'-end labelling of the $1^{st}$ domain: performing a restriction digest of the domain sequence of step (b) with a restriction enzyme targeting the restriction site at the 3'-end and performing a restriction digest of the domain sequences of any of steps (c) to (e) with restriction enzymes targeting the restriction sites at the 5'-ends, (ii) in case of 3'-end labelling of the $1^{st}$ domain: performing a restriction digest of the domain sequence of step (b) with a restriction enzyme targeting the restriction site at the 5'-end and performing a restriction digest of the domain sequences of any of steps (c) to (e) with restriction enzymes targeting the restriction sites at the 3'-ends;

(g) ligating the digested $1^{st}$ and $2^{nd}$ domain sequence obtained in step (f) to obtain a ligation product comprising the $1^{st}$ and $2^{nd}$ domain sequence;

(h) binding the ligation product of step (g) to a solid support using the tag labeling of the $1^{st}$ domain sequence to obtain a bound ligation product comprising the $1^{st}$ and $2^{nd}$ domain sequence, and performing a restriction digest of said bound ligation product:

(i) in case of 5'-end labelling of the $1^{st}$ domain: performing a restriction digest of the bound ligation product with a restriction enzyme targeting the 3'-end of the $2^{nd}$ domain, (ii) in case of 3'-end labelling of the $1^{st}$ domain: performing a restriction digest of the bound ligation product with a restriction enzyme targeting the 5' end of the $2^{nd}$ domain;

(j) optionally ligating the digested $3^{rd}$ domain sequence of step (d) obtained in step (f) to the bound ligation product of step (h) to obtain a bound ligation product comprising the $1^{st}$, $2^{nd}$ and $3^{rd}$ domain sequence, and performing a restriction digest of said bound ligation product:

(i) in case of 5'-end labelling of the $1^{st}$ domain: performing a restriction digest of the bound ligation product with a restriction enzyme targeting the 3'-end of the $3^{rd}$ domain.

(ii) in case of 3'-end labelling of the $1^{st}$ domain: performing a restriction digest of the bound ligation product with a restriction enzyme targeting the 5'-end of the $3^{rd}$ domain.

(k) optionally ligating one or more digested domain sequences of (e) obtained in step (f) to the bound ligation product of step (j) to obtain a bound ligation product comprising one or more further domain sequences of step (e), thereby performing after each ligation step a restriction digest of the bound ligation product as follows:

(i) in case of 5'-end labelling of the $1^{st}$ domain: performing a restriction digest of the bound ligation product with a restriction enzyme targeting the 3'-end of the said further domain sequence that was ligated to the bound ligation product, (ii) in case of 3'-end labelling of the $1^{st}$ domain: performing a restriction digest of the bound ligation product with a restriction enzyme targeting the 5'-end of the said further domain sequence that was ligated to the bound ligation product;

(l) releasing the ligation product obtained in any of steps (h) to (k) from the solid support;

(m) characterizing the ligation product obtained in step (l) and identifying chimeric polypeptides having at least one CBD and at least one EAD.

3". The method of item 1" or 2", further comprising a washing step after binding the first ligation product to the solid support in step (h) to remove unbound ligation products and/or non-ligated domain sequences.

4". The method of any one of items 1" to 3", wherein steps (g) and (h) are replaced by a step of binding the digested $1^{st}$ domain sequence to a solid support using the tag labeling at the 5'-end or 3'-end, respectively, and a subsequent step of ligating the digested $2^{nd}$ domain sequence of step (c) obtained in step (f) to the bound $1^{st}$ domain sequence to obtain a bound ligation product comprising the $1^{st}$ and $2^{nd}$ domain sequence, followed by performing a restriction digest of said bound ligation product:

(i) in case of 5'-end labelling of the $1^{st}$ domain: performing a restriction digest of the bound ligation product with a restriction enzyme targeting the 3'-end of the $2^{nd}$ domain, (ii) in case of 3'-end labelling of the $1^{st}$ domain: performing a restriction digest of the bound ligation product with a restriction enzyme targeting the 5' end of the $2^{nd}$ domain.

5". The method of item 4", further comprising a step of removing unbound domain sequences after binding the first ligation product to the solid support, and optionally a further step of removing non-ligated domain sequences after ligating the second domain sequence to the bound first domain sequence.

6". The method for screening a lytic chimeric polypeptide of any one of items 1" and 3" to 5", further comprising a step of removing non-ligated domain sequences and/or undesired products resulting from the restriction digest after each ligation and restriction step performed in any of steps (h) to (k).

7". The method for generating chimeric polypeptides having at least one CBD and at least one EAD of any one of items 2" to 5", further comprising a step of removing non-ligated domain sequences and/or undesired products resulting from the restriction digest after each ligation and restriction step performed in steps (h) to (k).

8". The method of any one of items 2" to 5", wherein step (m) comprises the steps of:

(m) cloning the ligation product obtained in step (l) into an expression vector;

(n) introducing the vector obtained in step (m) into an expression host, preferably into a bacterial expression host;

(o) culturing the expression host of step (n) carrying the vector obtained in step (m) under conditions suitable to allow expression of a lytic polypeptide encoded by the domain sequences of the cloned ligation product;

(p) selecting and isolating an expression clone expressing a lytic polypeptide according to step (o) using the lytic activity of the polypeptide; and (q) characterizing the lytic polypeptide expressed by the isolated expression clone of step (p) and identifying a lytic chimeric polypeptide having at least one CBD and at least one EAD.

9". The method of any one of items 1" to 8", wherein the domain sequences of (a) are cloned into a vector prior to amplification.

10". The method of any one of items 1" to 9", wherein the step of releasing the ligation product or ligation products from the solid support is carried out using a restriction enzyme targeting the restriction site at that end of the 1$^{st}$ domain, which is carrying the tag labelling.

11". The method of any one of items 1" to 10", wherein in case of repeated ligation steps optionally after any repeated ligation step part of the obtained bound ligation product is separated from the method prior to performing a subsequent ligation step.

12". The method of any one of items 1" to 11", wherein the solid support is a particle, a surface of a device, a foil or a fleece.

13". The method of item 12", wherein the particle is a silica bead or an organic polymer bead being magnetic.

14". A lytic chimeric polypeptide obtainable by the method for screening a lytic chimeric polypeptide of any one of items 1" and 3" to 13".

15". A chimeric polypeptide or a plurality of chimeric polypeptides obtainable by the method of generating chimeric polypeptides having at least one CBD and at least one EAD of any one of items 2" to 13".

16". A library of chimeric polypeptides obtainable by the method of any one of items 2" to 13".

EXAMPLES

Example 1: Cloning of Selected Domains

Table 1 shows selected domains used for library construction.

TABLE 1

Selected domains with description of protein source, domain borders of the amino acid sequence and enzymatic specificity of EADs.

| Protein source | SEQ ID NO: | Domain | Domain borders | Specificity |
|---|---|---|---|---|
| Endolysin, Ply511 | 1 | EAD511 | 1-195 | Amidase 2 |
| Endolysin, Ply511 | 1 | CBD511 | 194-141 + Linsyn | |
| Endolysin, Ply500 | 2 | EAD500 | 1-154 | VanY |
| Endolysin, Ply500 | 2 | CBD500 | 148-189 + Linsyn | |
| Endolysin, PlyP40 | 3 | EADP40 | 1-225 | Chalaropsis Lysozyme |
| Endolysin, PlyP40 | 3 | CBDP40 | A: 226-344 + Linsyn<br>B: 192-344 + Linsyn<br>C: 192-344 | |
| Endolysin, PlyP35 | 4 | EADP35 | 1-150 | VanY |
| Endolysin, PlyP35 | 4 | CBDP35 | 140-291 + Linsyn | |
| Endolysin, PlyB054 | 5 | EADB054 | 1-194 | Amidase 3 |
| Endolysin, PlyPSA | 6 | EADPSA | 1-182 | Amidase 3 |
| Endolysin, Ply006 | 7 | CBD006 | 157-235 + Linsyn | |
| Endolysin, PlyB025 | 8 | CBDB025 | 127-276 + Linsyn | |
| Lytic Tail protein, gp29 of P100 | 9 | EADgp29 | 641-795 + Linsyn | NlpC/p60 (CHAP) |
| Autolysin, L. monocytogenes | 10 | MurA | A: 52-327<br>B: 142-327 | Lysozym type 2 |
| Autolysin, L. monocytogenes | 11 | IspC | 1-226 | Lysozym type 2 |
| Bacteriocin, S. coelicolor Milner | 12 | Mutanolysin | 79-294 + Linsyn | Chalaropsis Lysozyme |
| Autolysin, S. aureus USA 300 | 13 | Sle1 | 201-334 + Linsyn | NlpC/p60 (CHAP) |

Linsyn: synthetic linker sequence, amino acid sequence: GGSKPGGTKPGGSKP.

The domains were amplified via PCR primers with the following design:

Forward primer (SEQ ID NO: 15)

CACACACCATGGCG (begin domain)

Reverse primer SpeI (SEQ ID NO: 16)

TGTGTGACTAGT (end domain without STOP codon)

Reverse primer BamHI

```
                                              (SEQ ID NO: 17)
TGTGTGGGATCC
(end domain without STOP codon)
```

Forward primer contain a NcoI-site, and reverse primer for attachment of a synthetic linker sequence have a SpeI-site, reverse primer for cloning without synthetic linker sequence have a BamHI-site. Restriction sites are shown in bold and underlined.

The purified PCR products were digested with NcoI and SpeI or NcoI and BamHI and ligated in a modified plasmid vector pET14b as shown in FIG. 1. This pET14b holds the sequence for the 3' synthetic linker region. The synthetic linker sequence is positioned between the SpeI site and the pET14b-BamHI site.

After transformation of *E. coli* HMS174 (DE3) using common procedures, positive clones were selected with ampicillin resistance. Clones that expressed the right sized protein were sequenced.

Example 2: Generation of Ligatable, Position Specific PCR Fragments

Figure 2:
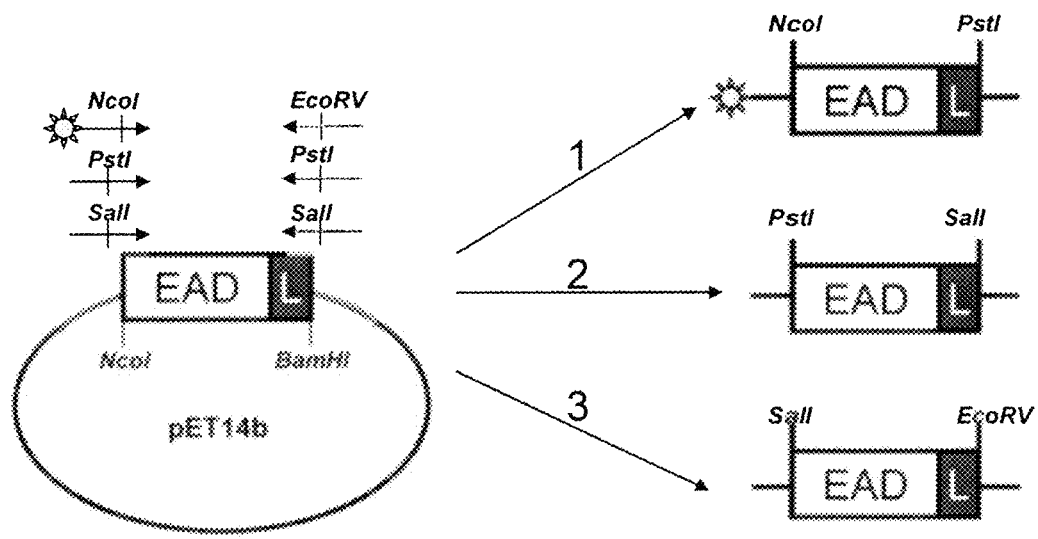
FIG. 2 shows a scheme for the introduction of position specific restriction sites by position specific primer combinations. In particular.
Figure 3:
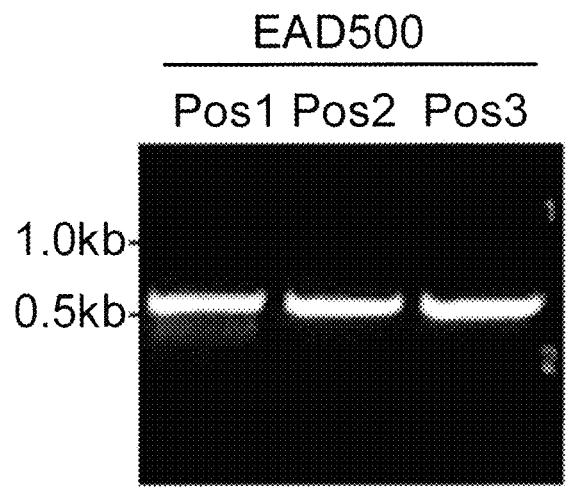
FIG. 3: PCR of EAD500 with position specific primer combinations and thus restriction sites of position 1, 2 and 3.

For introduction of the position specific restriction sites, the domains were amplified via PCR by position specific primer combinations (see FIG. 2 and Table 1). As PCR templates served the domains cloned in pET14b. FIG. 3 shows exemplarily the PCR products for position 1, 2 and 3 of EAD500.

TABLE 2

Position specific primer pairs.

```
Pos. 1    forward:
          B-5'-GTTTAACTTTAAGAAGGAGATATACCATGGCG-3'
          (SEQ ID NO: 18)
          reverse:
          5'-CCTTTCGGGCTTTGTTACTGCAGGGATCC-3'
          (SEQ ID NO: 19)

Pos. 2    forward:
          5'-GTTTAACTTTAAGAAGGAGACTGCAGATGGCG-3'
          (SEQ ID NO: 20)
          reverse:
          5'-CCTTTCGGGCTTTGTTAGTCGACGGATCC-3'
          (SEQ ID NO: 21)

Pos. 3    forward:
          5'-GTTTAACTTTAAGAAGGAGAGTCGACATGGCG-3'
          (SEQ ID NO: 22)
          reverse:
          5'-CCTTTCGGGCTTTGTTAGATATCGGATCC-3'
          (SEQ ID NO: 23)
```

B: 5'-attached Biotin-tag
CCATGG: NcoI-site
CTGCAG: PstI-site
GTCGAC: SalI-site
GATATC: EcoRV-site PCR for domain position 3 was performed twice: with non-biotinylated forward primer and with biotinylated forward primer. PCR products for position 1 and without biotin-tag are to be purified using common purification kits. PCR products with biotin-tag (all except for position 1) can be purified per streptavidin coated magnetic particles: binding to beads, washing and removing of beads by restriction digest.

Example 3: Test for Activity of Cloned Domains

All cloned domains were tested for domain activity. EADs were tested for *Listeria* lytic activity, CBDs were tested for *Listeria* binding activity.

3-1. Testing *Listeria* Lytic Activity of EADs

*E. coli* HMS (174) clones containing the pET14bEAD constructs were spotted on LB Top Agar plates containing IPTG for the induction of protein expression, ampicillin for the plasmid selection pressure and 120 µl heat inactivated *Listeria* cells of *Listeria monocytogenes* EGDe (J.Kreft), serotype 1/2a. Each domain was spotted and incubated at 30° C. and afterwards at room temperature. In case of *Listeria* lysis, the spotted *E. coli* clone is surrounded by a clearing in the agar. As a result, all tested EADs show lysis on *Listeria monocytogenes* EGDe.

Generation of heat inactivated *Listeria* cells: *Listeria* were grown in Tryptose Broth (TB), 30° C., shaking until OD=1. After harvesting, the cells were resuspended in ½₀₀ volume PBST (1×PBS+0.1% Tween) pH 8. The cells were heat inactivated for 20 minutes at 80° C. and stored at −20° C.

3-2. Testing *Listeria* Binding Activity of CBDs

Protein purification of C-His tagged proteins: The CBDs were subcloned in pQE60 NcoI and BamHI-sites. After transformation of *E. Coli* M15, CBDs were expressed with C-terminal His-tag.

Cell disruption was performed by sonication of the cell pellet in wash buffer (50 mM sodiumchloride buffer (NaPi) pH 7.5, 1 M NaCl, 20 mM Imidazole, 0.05% Tween). After centrifugation the supernatant was used for common affinity chromatography with Ni-sepharose. Washing steps were performed with wash buffer; elution was performed with elution buffer (50 mM *NaPi* pH 7.5, 1 M NaCl, 250 mM Imidazole, 0.05% Tween). The purified proteins were dialyzed against 25 mM Tris pH 8, 250 mM NaCl, 2.5 mM EDTA.

ELISA for cell binding test: Cell ELISA

Tested *Listeria* strains:
WSLC 2011: *Listeria innocua*, serotype 6a
WSLC 1485: *Listeria monocytogenes*, serotype 3a
EGDe (J.Kreft): *Listeria monocytogenes*, serotype 1/2a
Scott A 1685: *Listeria monocytogenes*, serotype 4b

*Listeria* strains were cultivated in TB until OD600=1. After washing the cells twice in 1×PBS pH 7.2, 96 well plates (MaxiSorp, Nunc) were coated with 10^8 cfu in 1×PBS for 1 h at room temperature. Anti-His-pUD-conjugate in PBST (0.05% Tween) pH 7.2 with 0.5% BSA was added for 1 h at room temperature after 3 washing steps with PBST. Before the substrate ABTS was added, the wells were washed twice with PBST and once with PBS.

The absorption was measured at 405/600 nm per ELISA reader. Result of binding is shown in Table 3.

TABLE 3

Qualification of cell binding. Shown is the minimal amount of signal to conclude strong cell binding.

| CBD-C His | Cell-ELISA |
| --- | --- |
| CBD006 | — |
| CBD025 | — |
| CBD511 | 30 fold background signal |
| CBD500 | 37 fold background signal |
| CBDP40-A, -B, -C | — |
| CBDP35 | 75 fold background signal |

Example 4: Specific Capture of Biotinylated DNA with Streptavidin Magnetic Particles (No Binding of Non-Biotinylated DNA) and Release by Restriction Digest 75 μg of streptavidin coated Beads (Microcoat) were washed with 500 μl 1×SSC (0.3 M sodiumcitrate, 3 M NaCl pH 7) and incubated with 3.76 pmol biotinylated DNA of 600 bp, 3.76 pmol biotinylated DNA of 1.4 kb and 3.76 pmol non-biotinylated DNA of 800 bp. After incubation at room temperature for 1 h the supernatant was removed (=S1) for agarose gel analysis. After two washing steps with 200 μl SSC the beads were washed with restriction buffer 1×NEB P3. The beads were resuspended in 20 μl 1×NEB P3 containing 10 U NcoI (NEB). The digest was performed for 2 h at 37° C. The supernatant (=S2) was removed for agarose gel analysis. S1, S2 and the beads were prepared for agarose gel analysis with gel buffer.

Figure 4:
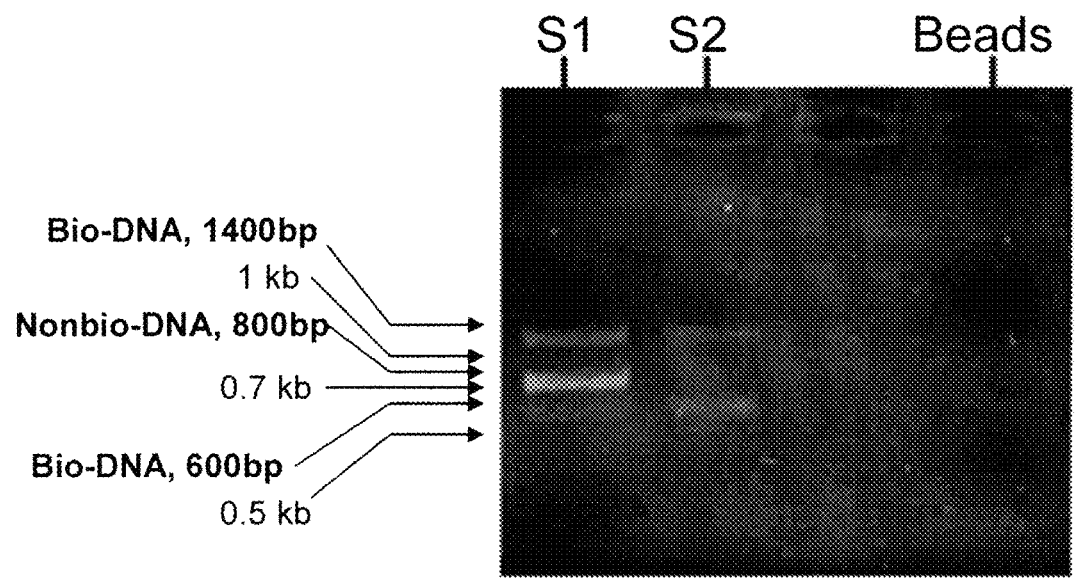
FIG. 4: Agarose gel analysis of S1, S2 and Beads.

FIG. 4 shows that S1 still contains biotinylated DNA (600 bp and 1.4 kbp). This means, that the binding capacity of the beads was exceeded. The entire non-biotinylated DNA (800 bp) is also found in S1, thus showing that the beads do not bind unspecific to DNA. Captured biotinylated DNA could be removed completely of the beads by restriction digest.

Example 5: Random Ligation of 4 N-Terminal EADs and 4 C-Terminal CBDs

Figures 5, 6:
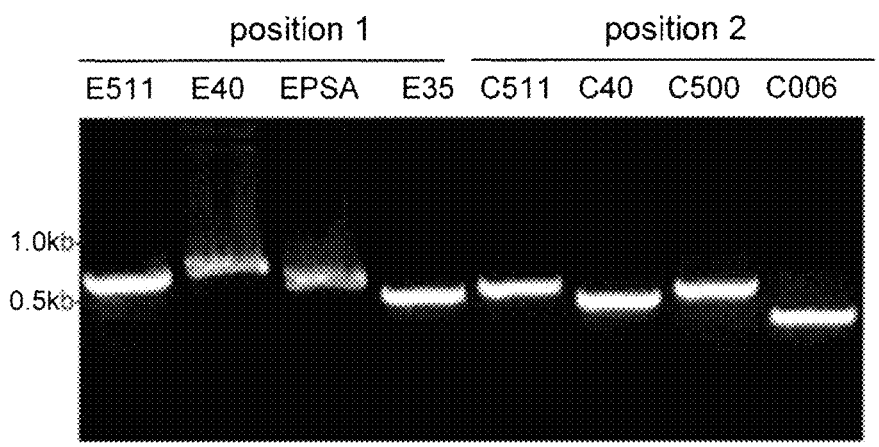
FIG. 5 shows the 16 possible constructs of the ligation of the 4 N-terminal EADs (EAD511, EADP35, EADP40 and EADPSA) combined with the 4 C-terminal CBDs (CBD006, CBD500, CBD511, CBDP40 variant A). In the random ligation every EAD should be ligated to every CBD.
FIG. 6: PCR fragments of EADs and CBDs for position 1 and position 2, respectively. E: EAD, C: CBD.

Four EADs for position 1 and four CBDs for position 2 were selected to be ligated randomly to 16 possible variants (see FIG. 5). For CBDP40 the variant A was chosen (see Table 1).

5-1. Generation of Position Specific PCR-Fragments of Domains

The EADs were amplified via specific PCR for position 1, the CBDs were amplified via specific PCR for position 2 (see Example 2). The PCR products were analyzed per agarose gel electrophoresis as shown in FIG. 6 and purified by common gel purification kits. All PCR products were digested with PstI and purified by common PCR purification kits.

5-2. Ligation of PstI-Digested Fragments and Capture by Streptavidin Coated Magnetic Particles Ligation was performed with a pool of 0.2 pmol of each digested fragment, T4 Ligase (NEB) and T4 Ligase buffer for 3 h at 16° C.

Figure 7:
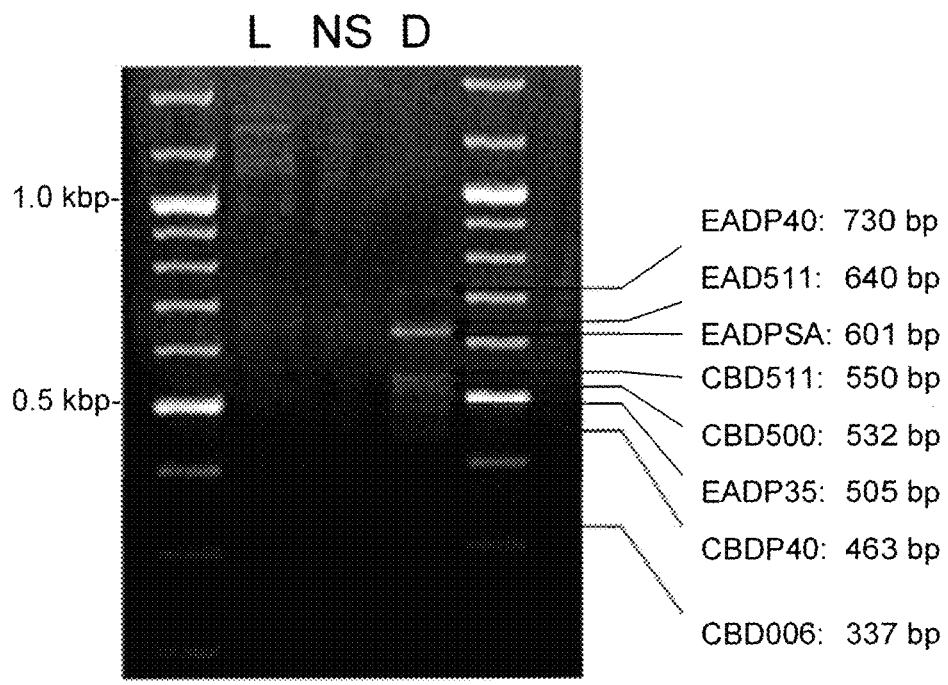
FIG. 7: Analysis of ligation and DNA-capture on 1.5% agarose gel. L: Ligation, NS: Supernatant after NcoI digest, D: pooled domains.

One third of the ligation was removed for gel analysis (L). The rest of ligated DNA was incubated with 750 μg magnetic streptavidin beads (MyOne Dynal-Beads Ti) which were washed twice with 500 μl 1×BW buffer (5 mM Tris pH 7.5, 0.5 mM EDTA, 1 M NaCl) before usage. After 30 minutes of shaking at room temperature the supernatant was removed. Three washing steps with 1×NEB4 buffer equilibrated the beads for digest in 1×NEB4 with SalI (NEB) for 2 h. The supernatant was removed (S-SalI) and the beads were washed with 1×NEB4. For cutting the DNA off the beads, NcoI-HF digest was performed in 1×NEB4 buffer for 2 h. The half of the supernatant (NS) was analyzed by agarose gel analysis (see FIG. 7). After heat inactivating the NcoI-HF enzyme (20 min., 80° C.) the remaining DNA was used for cloning (D).

Figure 8:
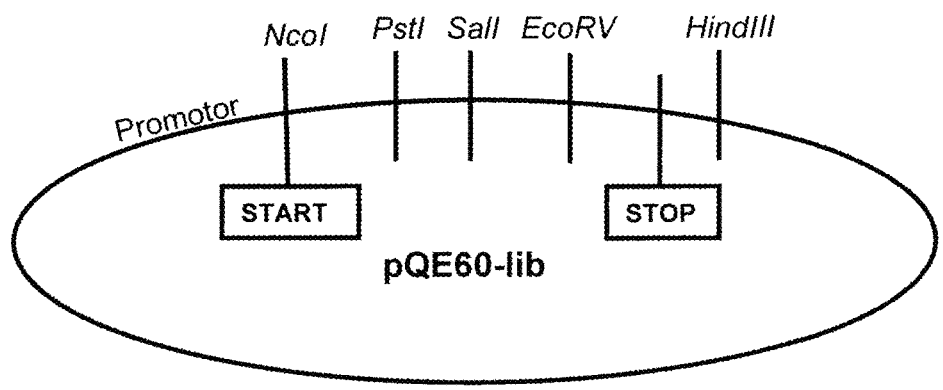
FIG. 8: Scheme of pQE60-lib with modified cloning site.

5-3. Cloning in Expression Vector and Transformation of *E. coli*, Plating on Selection Plates The remaining DNA was ligated via NcoI and SalI in pQE60-lib, a pQE60 with a modified multiple cloning site (see FIG. 8).

Figure 9:
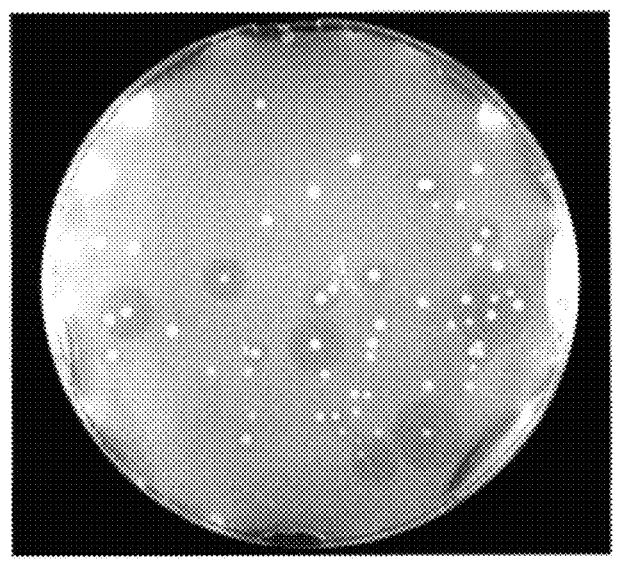
FIG. 9: Induced *E. coli* M15 cells show lysis after plasmid transformation and colony growth.

Ultracompetent *E. coli* cells M15 were transformed with the ligated DNA and plated on lysis selection plates containing LB Top Agar, 120 μl heat inactivated *Listeria* cells of WSLC 2011 (see Example 3-1), IPTG and Amp. Colonies that express a functionable and soluble *Listeria* lytic protein show lysis (see FIG. 9).

5-4. Confirmation of 16 Possible Variants and Test for Functionability

Figure 10:
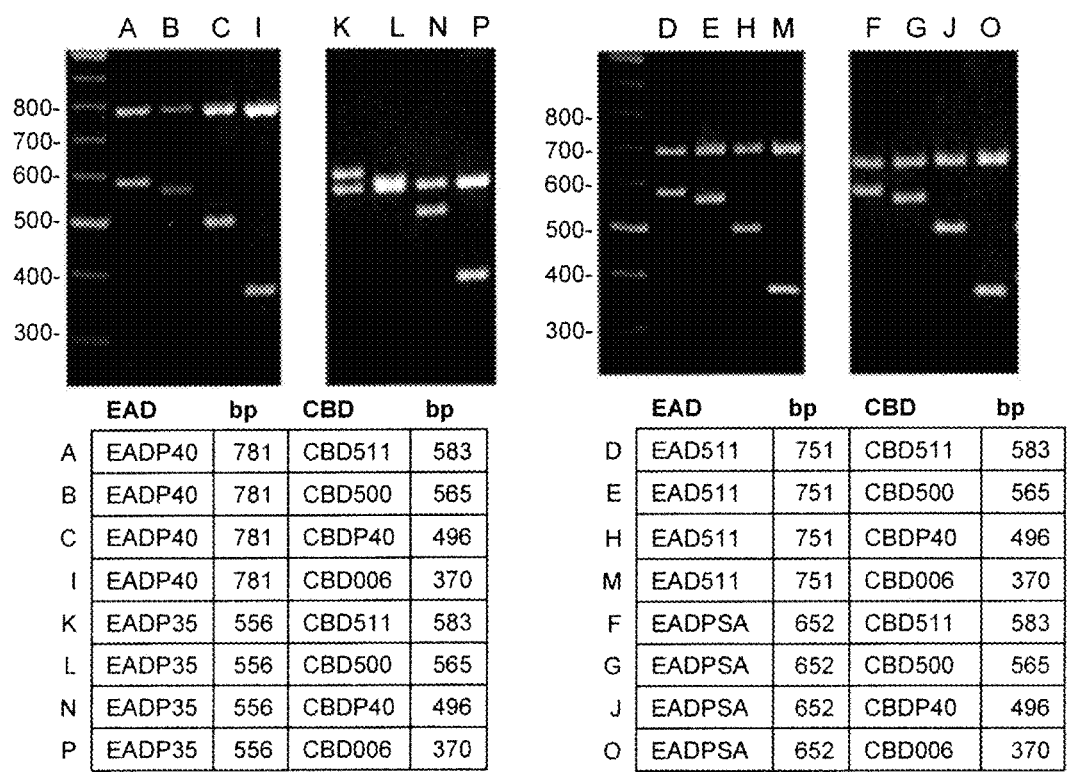
FIG. 10: Confirmation of the 16 possible variants.

To show that all possible domain combinations out of 4 N-terminal EADs and 4 C-terminal CBDs were generated, Colony PCR was performed on 88 clones with pQE forward and reverse primer. The PCR product was digested by PstI and analyzed on agarose gels. The result was confirmed by domain specific PCR. All but one construct was found using this procedure. The last construct (B in FIG. 10) was identified by Colony PCR on further 93 clones using cloning primer of EADP40-forward and CBD500-reverse, B was found two times. In conclusion all variants existed (see FIG. 10).

Figure 11:
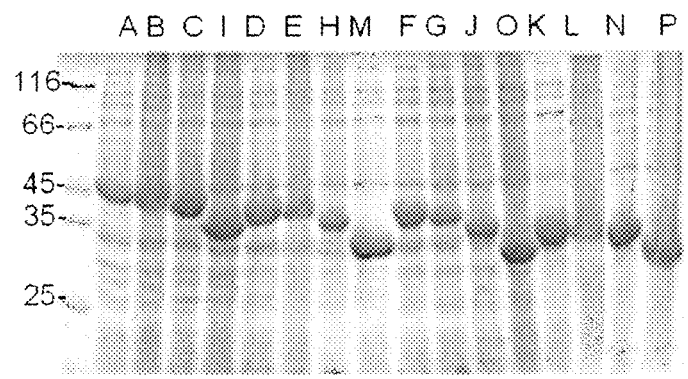
FIG. 11 shows the SDS gel analysis of protein expression of the 16 variants A-P. All proteins have the correct size. Hence, the domain fragments are ligated correctly without frame shifts. The numeration is the same as in FIG. 10.
Figure 13A:
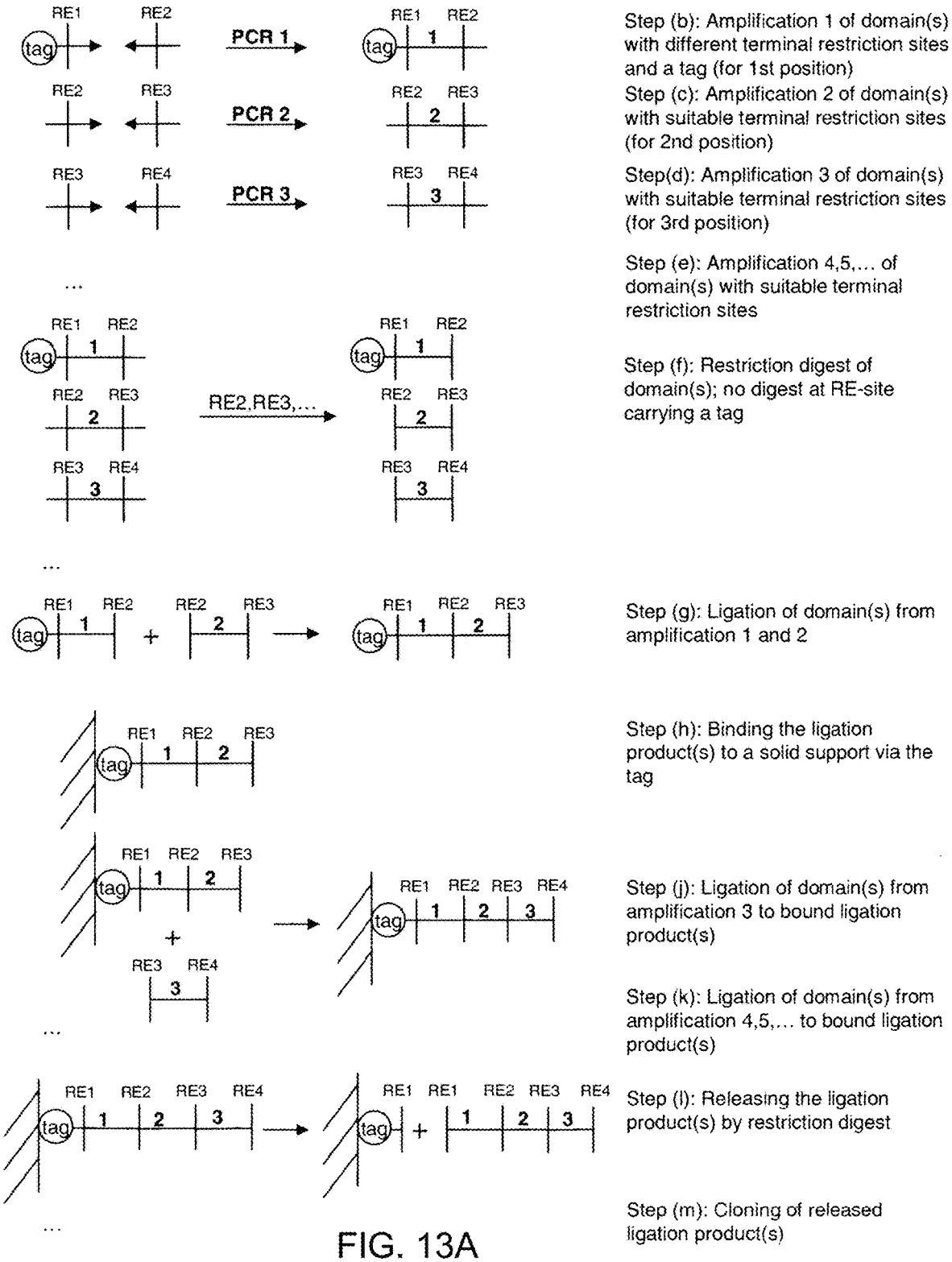
FIG. 13A-B.
Figure 13B:
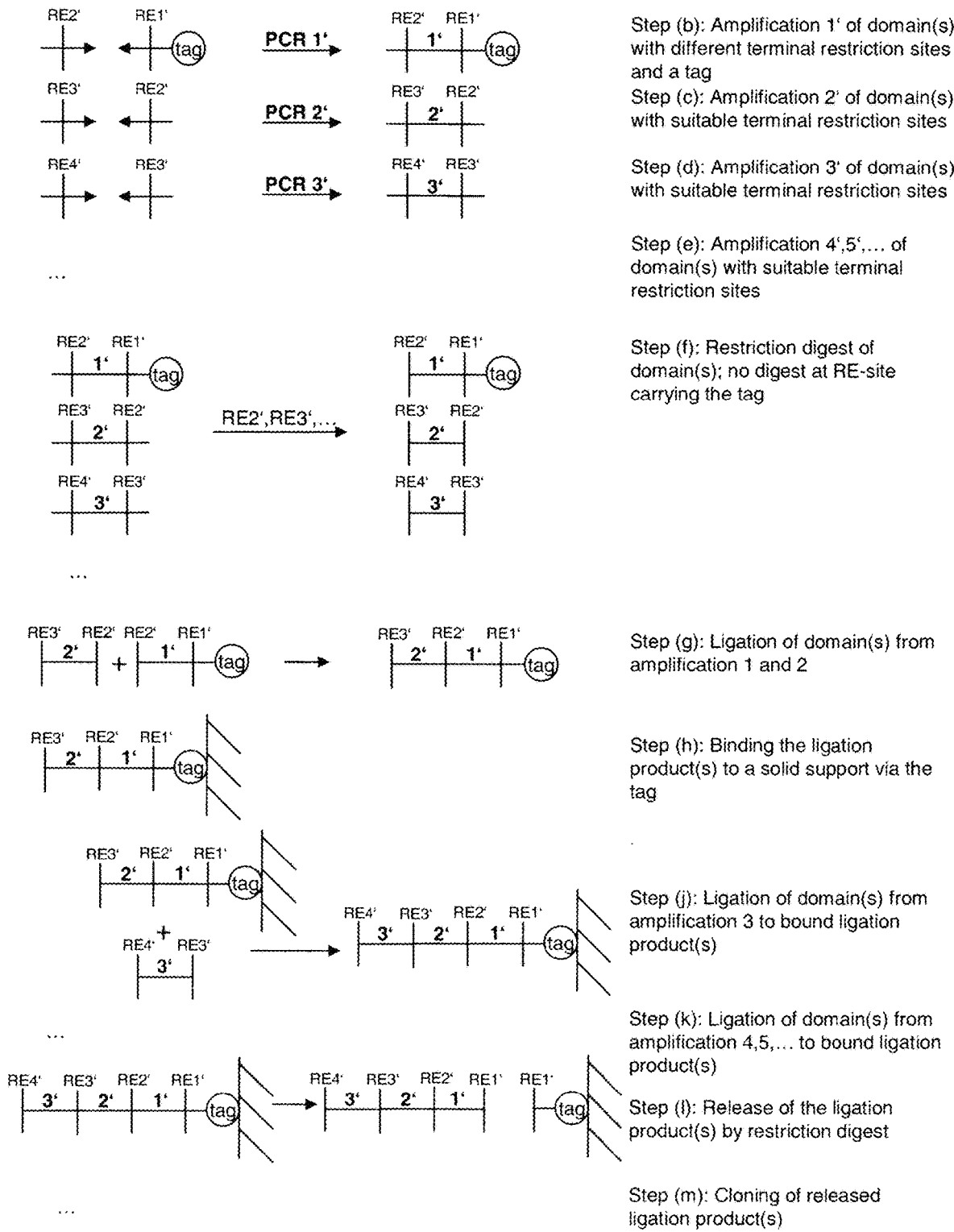

Expression was tested of all 16 variants for affirmation of the correct assembly of the two domains. As FIG. 11 shows, all 16 proteins have the right molecular weight.

The *Listeria* lytic activity was tested on LB Top agar plates with heat inactivated *Listeria* cells (see Example 3-1). The proteins behaved as expected along the corresponding CBDs, an exception were the constructs with CBDP40-A, that showed no serovar specific lytic activity (see FIG. 12). This result implies that CBDP40-A is inactive.

Example 6: Random Ligation of 19 Domains to 2-Domain Proteins and 3-Domain Proteins For the generation of 2- and 3-domain proteins every domain from Table 1 except for CBDP40-A was chosen, altogether this means the random combination of 19 different domains. That is, every domain can appear at every position. For 2 domain proteins, there are 361 possible domain combinations. For 3 domain proteins there are 6859 possible domain combinations.

6-1. 2-Domain Proteins

For every domain position specific PCR for position 1 and 2 was performed. Both fragments were digested with PstI. 0.06 pmol of each fragment were ligated by T4 Ligase in T4 buffer (NEB) and captured with 120 μl streptavidin beads (Microcoat) (twice washed with 1×BW) in 1×BW (2×BW=10 mM Tris pH 7.5, 1 mM EDTA, 2 M NaCl). The supernatant with unbound DNA was removed and the beads were washed with 1×NEB4. After 2 h digest with SalI-HF in 1×NEB4 (NEB) the beads were washed again. For release of DNA of beads NcoI-HF digest was performed in 1×NEB4 buffer for 2 h. After heat inactivating the NcoI-HF enzyme (20 min, 80° C.) the DNA was used for cloning.

The DNA was ligated via NcoI and SalI in pQE60-lib, ultracompetent *E. coli* cells M15 were transformed and plated on lysis selection plates containing LB Top Agar, 120 μl heat inactivated *Listeria* cells of WSLC 2011 (see Example 3-1), IPTG and ampicillin. Colonies that expressed a functionable and soluble *Listeria* lytic protein showed lysis and were collected.

The collected *E. coli* clones were tested for lysis on several strains:
  WSLC 2011: *Listeria innocua*, serotype 6a
  WSLC 1485: *Listeria monocytogenes*, serotype 3a
  EGDe (J.Kreft): *Listeria monocytogenes*, serotype 1/2a
  Scott A 1685: *Listeria monocytogenes*, serotype 4b
  1057 clones were analyzed, i.e. nearly 3-fold more clones than possible variants. 49 clones showed lysis on *L. innocua*

WSLC 2011 and were picked and sequenced. Sequencing showed that the 49 clones contained 21 different combinations, and 11 of the 21 different combinations lysed all of the 4 tested serovars. For validation 20 clones independent of lytic behaviour were sequenced. As a result, there were 18 different domain combinations and one clone with a domain foreign fragment. All domains were found except for CBDP35.

6-2. 3-Domain Proteins

The construction of 3-domain proteins follows the same protocol as for 2-domain proteins but after the SalI-HF digest the DNA is not released of the beads but ligated with a 10 fold amount of SalI digested fragment for position 3 (0.6 pmol of each domain) in 1×NEB4 buffer with T4 Ligase and 1 mM ATP. Afterwards the DNA is digested by EcoRV-HF in NEB4 for 2 hours and released of the beads by NcoI digest in 1×NEB4 buffer for 2 h. After heat inactivating the NcoI-HF enzyme (20 min., 80° C.) the DNA was used for cloning.

The DNA was ligated via NcoI and EcoRV in pQE60-lib, ultracompetent *E. coli* cells M15 were transformed with the ligation and plated on lysis selection plates containing LB Top Agar, 120 µl heat inactivated *Listeria monocytogenes* cells of EGDe (see Example 3-1), IPTG and ampicillin. Colonies that expressed a functionable and soluble *Listeria* lytic protein showed lysis and were collected.

The collected *E. coli* clones were tested for lysis on several strains:

WSLC 2011: *Listeria innocua*, serotype 6a

WSLC 1485: *Listeria monocytogenes*, serotype 3a

EGDe (J.Kreft): *Listeria monocytogenes*, serotype 1/2a

Scott A 1685: *Listeria monocytogenes*, serotype 4b 13482 clones were analyzed, i.e. means nearly 2-fold more clones than possible variants. About 940 clones showed lysis on *L. monocytogenes* EGDe and were picked. 240 clones showed lysis on at least 3 of the 4 tested serovars. Sequencing has revealed 132 different 3-domain proteins with at least one CBD and at least one EAD. In the 240 sequence clones all domains were found in almost every possible position.

REFERENCES

1. UK patent application GB 2 255 561 A (Nov. 11, 1992).
2. Nelson D. et al., 2001, PNAS 98(7):4107-4112.
3. Rashel M. et al., 2007, J. Infect. Dis. 196(8):1237-1247.
4. U.S. Pat. No. 5,997,862 (Dec. 7, 1999).
5. Takác M. and U. Blasi, 2005, Antimicrob. Agents Chemother. 49(7):2934-2940.
6. Navarre W. et al., 1999, J. Biol. Chem. 274(22):15847-15856.
7. Sass P. and G. Bierbaum, 2007, Appl. Environ. Microbiol. 73(1):347-352.
8. O'Flaherty S. et al., 2005, J. Bacteriol. 187(20):7161-7164.
9. WO 2008/001342 (Jan. 3, 2008)
10. Becker S. et al., 2008, FEMS Micobiol. Lett. 287(2):185-191.
11. Horgan M. et al., 2009, Appl. Environ. Microbiol. 75(3):872-874.
12. Kokai-Kun J. F. et al., 2007, J. Antimicrob. Chemother. 60(5):1051-1059.
13. Kusuma C. et al., 2007, Antimicrob. Agents Chemother. 51(2):475-482.
14. DeHart H. P. et al., 1995, Appl. Environ. Microbiol. 61(4):1475-1479.
15. Ehlert K. et al., 1997, J. Bacteriol. 197(23):7573-7576.
16. Stranden A. M. et al., 1997, J. Bacteriol. 197(1):9-16.
17. Diaz E. et al., 1990, Proc. Natl. Acad. Sci. USA 87:8125-8129.
18. Croux C. et al., 1993, Mol. Microbiol. 9(5):1019-1025.
19. Donovan D. M. et al., 2006, Appl. Environ. Microbiol. 72(4):2988-2996.
20. Loessner M. J. et al., 2002, Molecular Microbiology 44(2):335-349.
21. Korndorfer I. P. et al., 2006, J. Mol. Biol. 364(4):678-689.
22. Schuch R. et al., 2009, in: Martha R. J. Clokie, Andrew M. Kropinski (eds.), Bacteriophages: Methods and Protocols, vol. 2: Molecular and Applied Aspects, Vol. 502, Humana Press.
23. Schmitz J. E. et al., 2008, Appl. Environ. Microbiol. 74(5):1649-1652.
24. Kusuma M. and Kokai-Kun F., 2005, Antimicrob. Agents Chemother. 49(8):3256-63.

---

SEQUENCE LISTING

```
SEQ ID NO: 1: amino acid sequence of endolysin Ply511 (341 amino acid residues;
origin: bacteriophage A511)
  1 MVKYTVENKI IAGLPKGKLK GANFVIAHET ANSKSTIDNE VSYMTRNWKN
 51 AFVTHFVGGG GRVVQVANVN YVSWGAGQYA NSYSYAQVEL CRTSNATTFK
101 KDYEVYCQLL VDLAKKAGIP ITLDSGSKTS DKGIKSHKWV ADKLGGTTHQ
151 DPYAYLSSWG ISKAQFASDL AKVSGGGNTG TAPAKPSTPA PKPSTPSTNL
201 DKLGLVDYMN AKKMDSSYSN RDKLAKQYGI ANYSGTASQN TTLLSKIKGG
251 APKPSTPAPK PSTSTAKKIY FPPNKGNWSV YPTNKAPVKA NAIGAINPTK
301 FGGLTYTIQK DRGNGVYEIQ TDQFGRVQVY GAPSTGAVIK K SEQ ID NO: 2: amino acid sequence of endolysin Ply500 (289 amino acid residues;
origin: bacteriophage A500)
  1 MALTEAWLIE KANRKLNAGG MYKITSDKTR NVIKKMAKEG IYLCVAQGYR
 51 STAEQNALYA QGRTKPGAIV TNAKGGQSNH NYGVAVDLCL YTNDGKDVIW
101 ESTTSRWKKV VAAMKAEGFK WGGDWKSFKD YPHFELCDAV SGEKIPAATQ
151 NTNTNSNRYE GKVIDSAPLL PKMDFKSSPF RMYKVGTEFL VYDHNQYWYK
201 TYIDDKLYYM YKSFCDVVAK KDAKGRIKVR IKSAKDLRIP VWNNIKLNSG
251 KIKWYAPNVK LAWYNYRRGY LELWYPNDGW YYTAEYFLK SEQ ID NO: 3: amino acid sequence of endolysin PlyP40 (344 amino acid residues;
origin: bacteriophage P40)
  1 MVLVLDISKW QPTVNYSGLK EDVGFVVIRS SNGTQKYDER LEQHAKGLDK
 51 VGMPFGLYHY ALFEGGQDTI NEANMLVSAY KKCRQLGAEP TFLFLDYEEV
101 KLKSGNVVNE CQRFIDHVKG QTGVKVGLYA GDSFWKTHDL DKVKHDLRWV
151 ARYGVDNGKP STKPSIPYDL WQYTSKGRIK AIASPVDMNT CSSDILNKLK
```

```
201 GSKAPVKPAP KPTPSKPAPA KPAPKTTTKY VNTAHLNIRE KASADSKVLG
251 VLDLNDSVQV ISESGGWSKL KSGNKQVYVS SKYLSKSKTT PKAKPSSKQY
301 YTIKSGDNLS YIAKKYKTTV KQIQNWNGIK DANKIYAGQK IRVK

SEQ ID NO: 4: amino acid sequence of endolysin PlyP35 (291 amino acid residues;
origin: bacteriophage P35)
  1 MARKFTKAEL VAKAEKKVGG LKPDVKKAVL SAVKEAYDRY GIGIIVSQGY
 51 RSIAEQNGLY AQGRTKPGNI VTNAKGGQSN HNFGVAVDFA IDLIDDGKID
101 SWQPSATIVN MMKRRGFKWG GDWKSFTDLP HFEACDWYRG ERKYKVDTSE
151 WKKKENINIV IKDVGYFQDK PQFLNSKSVR QWKHGTKVKL TKHNSHWYTG
201 VVKDGNKSVR GYIYHSMAKV TSKNSDGSVN ATINAHAFCW DNKKLNGGDF
251 INLKRGFKGI THPASDGFYP LYFASRKKTF YIPRYMFDIK K SEQ ID NO: 5: amino acid sequence of endolysin PlyB054 (321 amino acid residues;
origin: bacteriophage B054)
  1 MAKKLKLAIY AGHGGVDSGA TGEGYREDDL TLDIAKRTTK VLRGAGHTVI
 51 NNRTTDVNRN ISADAKLANR EKVDAVIEFH FDAAGASAEG TTGFYCEGSS
101 SSKKLAQCVN DKLDDVFKDR NVKPDTSTRH GRLGILRETN AVATLQEVAF
151 ITNKNDMIKY NQRADEIAKK AAEGILSYFN EKLPEQNPNR HDGAVVDSIP
201 ALPKPDFKTV PSKMYKAGSE LLVYDHNKYW YKTYINDKLC YIYKSFCISN
251 GKKDSKGRIP IKIKSVKDLR IPVWDNTKLS SGKIKWYAPN TKLSWYNNKK
301 GYLELYYPNQ GWYYTANYFL K SEQ ID NO: 6: amino acid sequence of endolysin PlyPSA (314 amino acid residues;
origin: bacteriophage PSA)
  1 MSNYSMSRGH SDKCVGAEDI LSEIKEAEKV LNAASDELKR EGHNVKTFID
 51 RTSTTQSANL NKIVNWHNAN PADVHISVHL NAGKGTGVEV WYYAGDEKGR
101 KLAVEISAKM AKALGLPNRG AKATKDLRFL NSTKGTAVLL EVCFVDRKED
151 ANAIHKSGMY DKLGIAIAEG LTGKTVAAKN PNRHSGAVVD SVPMLSKMDF
201 KSSPIKMYKA GSSLLVYEHN KYWYKAYIND KLCYIYKSFC ISNGKKDAKG
251 RIKVRIKSAK DLRIPVWNNT KLNSGKIKWY SPGTKLSWYD NKKGYLELWY
301 EKDGWYYTAN YFLK SEQ ID NO: 7: amino acid sequence of endolysin Ply006 (235 amino acid residues;
origin: bacteriophage A006)
  1 MALTEAWLIE KANRKLNVSG MNKSVADKTR NVIKKMAKKG IYLCVAQGYR
 51 SSAEQNALYA QGRTKPGAVV TNAKGGQSNH NYGVAVDLCL YTSDGKNVIW
101 ESTTSRWKTV VSAMKAEGFE WGGDWKSFKD YPHFELYDAA GGEKAPSTSA
151 SKPATSTSSN KNVYYTENPR KVKTLVQCDL YNSVDFTEKH KTGGTYPAGT
201 VFTISGMGKT KGGTPRLKTK SGYYLTANKK FVKKI SEQ ID NO: 8: amino acid sequence of endolysin PlyB025 (276 amino acid residues;
origin: bacteriophage B025)
  1 MTMYYEERSR NNIAKLAANT RAKALEWFNW CCKNGIEVLV YETIRTKEQQ
 51 AANVANGKSQ TMRSYHIVGQ AFDFVMAKGK TVDWGGYKTA KAKKVIAKAK
101 ALGFSWGGDW SGFVDCPHMQ YEYKGYGTDK FTADKLVANN KTGKQGVYAR
151 DFLNIRTKAT WDSPVAFKVP IYYYAQILWD TKNGDWVQIE FQGKKGWYKP
201 SFKEYWYEKD PCTSYICVAD VNFRKSSKWD SPVAQKKKKG ETVRMVKKAK
251 NGWLEFGLTN GVIGYIPNSA KYVKKK SEQ ID NO: 9: amino acid sequence of lytic tail protein gp29 (795 amino acid
residues; origin: bacteriophage P100)
  1 MTTVKRMPEF DLKFVTEKND YLIRYDARNP SSDTLAEKVI SVTTKNAMSD
 51 DSAVFSIVVA GDMEWDKILD SNDVVILKIY PNLRVMMPDN VVVLVGLISE
101 VRREGDYSNN SIIYRITGQS FAKSFMQFQL GVIQEVSVVI TDIGWLPDSK
151 ADGVEFTGKT AAEIGKSITD RFKKYMKYNF NREYTMENFL DYSFSSWKDY
201 EKLADPTPFI NYEGSLKQLL DDVTAKPFNE LFFESTSDEK CKMIMRRTPF
251 NKEDWDKLPS YKISTEAVIS DSLAKGDTEA YSIFNVTSGN MAGATSVDLN
301 SPPQYHQALV DKYGYKKLEV DNRYLFESST DGSSTTEKAD VGSKEKTKTV
351 ITYSKFNSFM RSYTSDQVRM NQSSIAKSLV DSYDKLTTSQ ANQLLAKYSA
401 VGAISEADFK KIVGDIAEGD NTGTATLDFD SVNSWFSLNY SSLSEVSTNR
451 DATIKAFVKN FANTDEDQAT KIVALYISSQ GVMTKEKFDA IIKESTSSST
501 KDPDNTTGNS SSALQYFSKT IYNWYSENAN FYAGDIKVIG SPVYRLGSKL
551 LVEDKQQGDE WEFYIESVSH EYSYTAGYTT TLGVTRGLNN KGKDRFTHLW
601 GKSSDFKGGL LGEKTSAELI QEAGSTSSGS DGSGDVSAPD VQGSDVAVAA
651 LRYGLAHKKP EKKSVYSFGG GRGSSNPMEG KEPYAMDCSS FVWWCYKACG
701 VTLAGAQTQA ILGDDRFNTV SSRGSKSKEI FKKMQVGDLV YFYDNNTHIG
751 MYAGEGKFLG CNGDGSWDTN GGVQLKPMDS GYWWTQFQGH VIRFV SEQ ID NO: 10: amino acid sequence of autolysin MurA from Listeria monocytogenes
residues, origin: Listeria monocytogenes EGDe (J.Kreft), serotype 1/2a)
  1 MQKTRKERIL EALQEEKKNK KSKKFKTGAT IAGVTAIATS ITVPGIEVIV
 51 SADETAPADE ASKSAEANTT KEASATATPE NTAKQTVGPQ QTETKEQTKT
101 PEEQAATNQ VEKAPAEPAT VSNPDNATSS STPATYNLLQ KSALRSGATV
151 QSFIQTIQAS SSQIAAENDL YASVMIAQAI LESAYGTSEL GSAPNYNLFG
201 IKGAYNGQSY TKQTLEDDGK GNYYTITAKF RKYPSYHQSL EDYAQVIRKG
251 PSWNPNYYSK AWKSNTTSYK DATKALTGTY ATDTAYATKL NDLISRYNLT
```

SEQUENCE LISTING

```
301 QYDSGKTTGG NSGSTGNSSN TGNTNTSNAK IYTVVKGDSL WRIANNHKVT
351 VANLKAWNNL KSDFIYPGQK LKVSAGSTTS DTNTSKPSTG TSTSKPSTGT
401 STNAKVYTVV KGDSLWRIAN NNKVTIANLK AWNNLKSDFI YPGQKLKVSA
451 GSTSNTNTSK PSTNTNTSKP STNTNTNAKV YTVAKGDSLW RIANNNKVTI
501 ANLKAWNNLK SDFIYPGQKL KVSAGSTTNT NTAKPSTNNP SNSTVKTYTV
551 KKGDSLWAIS RQYKTTVDNI KAWNKLTSNM IHVGQKLTIK
```

SEQ ID NO: 11: amino acid sequence of autolysin IspC from *Listeria monocytogenes* (774 amino acid residues; origin: *Listeria monocytogenes* LI 0521, serotype4b)
```
  1 MINKKWMKIV MIPMLVVPMY GLTTVGGQLQ DSLTGENSFV KEVEAATTAS
 51 QQAFIDKIAP AAQASQEKYH LLSSITLAQA ILESGWGKSG LATQGYNLFG
101 IKGKYNGQSV IMTTSEYVNG EWIKIDAEFR KYPSWNESVT DHTLLLVNGT
151 SWNKDLYKKV VDATDYKVTA MEPQKAGYAT SPTYGASLIQ VIENYDLAKY
201 DVLYDKILTQ KSTSGKATVT SPTGNGVWTL PYKVKGVQSV SPASTYANKD
251 IDLVSVATTK RGTYYQFKYN GKVVGWVDGK ALTIYDSVNY DKVNVGRAKI
301 TSPVSNGIWS KPYNVYGREF VTNATTYAQQ EIKLLREAQT AKGTYYQFSI
351 NNKTIGWIDK RALTIYPYDS IISSKNVNLD GQITNPTGNG IWTKAYKLEG
401 TTSVAQATKY ANKDVKISQQ IETQHGTYYN ISIDGKAIGW LDRNAITLYD
451 QEEYNKTVAI DAVVKNVKGN AVWTEPYRTV GTKLIGPAET YLNKEVEVVR
501 EAKTPKGTYY QFKSGGKVIG WLDKKAFDVY DNINYNKAVN LDAVVENVTG
551 NAVWTAPYKS KGVKLVTSAA TYKGKATKIT REAQTSRGTY YEFSVDGKVI
601 GWLDKKAFDV YDNINYNKAV NLDAVVENVT GNAVWTAPYK SKGVKLVTSA
651 ATYKDKATKI TREAQTSRGT YYEFSVNGKV IGWLDKKAFD VYDSIEYNKA
701 INMTGLLSNA PGNGIWTEPY RVIGTKNVGQ ATAYANKTVQ LIREAKTTRA
751 TYYQMSVNGK IVGWVDKRAF TNVK
```

SEQ ID NO: 12: amino acid sequence of bacteriocin from *Streptomyces coelicolor* Wier (294 amino acid residues; origin: *Streptomyces coelicolor* Wier)
```
  1 MPAYSSLARR GRRPAVVLLG GLVSASLALT LAPTAAAAPL APPPGKDVGP
 51 GEAYMGVGTR IEQGLGAGPD ERTIGPADTS GVQGIDVSHW QGSINWSSVK
101 SAGMSFAYIK ATEGTNYKDD RFSANYTNAY NAGIIRGAYH FARPNASSGT
151 AQADYFASNG GGWSRDNRTL PGVLDIEHNP SGAMCYGLST TQMRTWINDF
201 HARYKARTTR DVVIYTTASW WNTCTGSWNG MAAKSPFWVA HWGVSAPTVP
251 SGFPTWTFWQ YSATGRVGGV SGDVDRNKFN GSAARLLALA NNTA
```

SEQ ID NO: 13: amino acid sequence of autolysin from *Staphylococcus aureus* USA300 (334 amino acid residues; origin: *Staphylococcus aureus* USA300)
```
  1 MQKKVIAAII GTSAISAVAA TQANAATTHT VKPGESVWAI SNKYGISIAK
 51 LKSLNNLTSN LIFPNQVLKV SGSSNSTSNS SRPSTNSGGG SYYTVQAGDS
101 LSLIASKYGT TYQNIMRLNG LNNFFIYPGQ KLKVSGTASS SNAASNSSRP
151 STNSGGGSYY TVQAGDSLSL IASKYGTTYQ KIMSLNGLNN FFIYPGQKLK
201 VTGNASTNSG SATTTNRGYN TPVFSHQNLY TWGQCTYHVF NRRAEIGKGI
251 STYWWNANNW DNAAAADGYT IDNRPTVGSI AQTDVGYYGH VMFVERVNND
301 GSILVSEMNY SAAPGILTYR TVPAYQVNNY RYIH
```

SEQ ID NO: 14: artificial sequence (amino acid sequence designed to act as a linker)
GGSKPGGTKPGGSKP SEQ ID NO: 15: artificial sequence (nucleotide sequence designed to act as a primer)
CACACACCATGGCG SEQ ID NO: 16: artificial sequence (nucleotide sequence designed to act as a primer)
TGTGTGACTAGT SEQ ID NO: 17: artificial sequence (nucleotide sequence designed to act as a primer)
TGTGTGGGATCC SEQ ID NO: 18: artificial sequence (nucleotide sequence designed to act as a primer)
GTTTAACTTTAAGAAGGAGATATACCATGGCG SEQ ID NO: 19: artificial sequence (nucleotide sequence designed to act as a primer)
CCTTTCGGGCTTTGTTACTGCAGGGATCC SEQ ID NO: 20: artificial sequence (nucleotide sequence designed to act as a primer)
GTTTAACTTTAAGAAGGAGACTGCAGATGGCG SEQ ID NO: 21: artificial sequence (nucleotide sequence designed to act as a primer)
CCTTTCGGGCTTTGTTAGTCGACGGATCC SEQ ID NO: 22: artificial sequence (nucleotide sequence designed to act as a primer)
GTTTAACTTTAAGAAGGAGAGTCGACATGGCG SEQ ID NO: 23: artificial sequence (nucleotide sequence designed to act as a primer)
CCTTTCGGGCTTTGTTAGATATCGGATCC

The invention claimed is:

1. A method of generating a chimeric polypeptide having at least one cell binding domain (CBD) and at least one enzymatic active domain (EAD), the method comprising the steps of:
   (a) providing one or more DNA sequences each encoding at least one CBD and one or more DNA sequences each encoding at least one EAD, and optionally one or more DNA sequences each encoding at least one CBD and at least one EAD, wherein the EAD is selected from the group consisting of
      (i) the lytic domain of a bacteriophage lysin; and
      (ii) a bacteriophage tail-associated protein having lytic activity;
   (b) amplifying a first ($1^{st}$) domain sequence selected from the domain sequences of (a) using a pair of primers designed to introduce different restriction sites at the 5'-end and at the 3'-end, and a tag labeling at the 5'-end or at the 3'-end;
   (c) amplifying a second ($2^{nd}$) domain sequence selected from the domain sequences of (a) using a pair of primers designed to introduce:
      (i) in case of 5'-end labelling of the $1^{st}$ domain: at the 5'-end the same restriction site as at the 3'-end of the first domain, and at the 3'-end a restriction site different from the restriction sites introduced into the $1^{st}$ domain sequence,
      (ii) in case of 3'-end labelling of the $1^{st}$ domain: at the 3'-end the same restriction site as at the 5'-end of the $1^{st}$ domain, and at the 5'-end a restriction site different from the restriction sites introduced into the $1^{st}$ domain sequence;
   (d) amplifying a third ($3^{rd}$) domain sequence selected from the domain sequences of (a) using a pair of primers designed to introduce:
      (i) in case of 5'-end labelling of the $1^{st}$ domain: at the 5'-end the same restriction site as at the 3'-end of the preceding $2^{nd}$ domain, and at the 3'-end a restriction site that is different from that at the 5'-end of the $1^{st}$ domain,
      (ii) in case of 3'-end labelling of the $1^{st}$ domain: at the 3'-end the same restriction site as at the 5'-end of the preceding $2^{nd}$ domain, and at the 5'-end a restriction site that is different from that at the 3'-end of the $1^{st}$ domain;
   wherein the pair of primers is further designed such that the restriction sites are different at the 5'-end and the 3'-end of the $3^{rd}$ domain sequence;
   (e) optionally amplifying one or more further domain sequences selected from the domain sequences of (a) for extending the series of domain sequences according to steps (b) to (d), using for each of said one or more further domain sequences a pair of primers designed following the principle of steps (c) and (d) so as to introduce:
      (i) in case of 5'-end labelling of the $1^{st}$ domain: at the 5'-end the same restriction site as at the 3'-end of the preceding domain, and at the 3'-end a restriction site that is different from that at the 5'-end of the $1^{st}$ domain,
      (ii) in case of 3'-end labelling of the $1^{st}$ domain: at the 3'-end the same restriction site as at the 5'-end of the preceding domain, and at the 5'-end a restriction site that is different from that at the 3'-end of the $1^{st}$ domain;
   wherein the pair of primers is further designed such that the restriction sites are different at the 5'-end and the 3'-end of each of said one or more further domain sequences;

(f) performing a restriction digest of the amplified domain sequences of any of steps (b) to (e) using restriction enzymes targeting the restriction sites introduced in any of steps (b) to (e), wherein a restriction digest is not performed on the restriction site introduced to an end carrying a tag labelling;

(g) ligating the digested $1^{st}$ and $2^{nd}$ domain sequence obtained in step (f) to obtain a ligation product comprising the $1^{st}$ and $2^{nd}$ domain sequence;

(h) binding the ligation products of step (g) to a solid support using the tag labeling of the $1^{st}$ domain sequence to obtain a bound ligation product comprising the $1^{st}$ and $2^{nd}$ domain sequence;

(j) optionally ligating the digested $3^{rd}$ domain sequence of (d) obtained in step (f) to the bound ligation product of step (h) to obtain a bound ligation product comprising the $1^{st}$, $2^{nd}$ and $3^{rd}$ domain sequence;

(k) optionally ligating one or more digested domain sequences of (e) obtained in step (f) to the bound ligation product of step (j) to obtain a bound ligation product comprising one or more further domain sequences of (e);

(l) releasing the ligation product obtained in any one of steps (h) to (k) from the solid support; and (m) characterizing the ligation product obtained in step (l) and identifying chimeric polypeptides having at least one CBD and at least one EAD.

2. The method of claim 1, further comprising a washing step after binding the first ligation product to the solid support in step (h) to remove unbound ligation products and/or non-ligated domain sequences.

3. The method of claim 1, wherein steps (g) and (h) are replaced by a step of binding the digested $1^{st}$ domain sequence to a solid support using the tag labeling at the 5'-end or 3'-end, respectively, and a subsequent step of ligating the digested $2^{nd}$ domain sequence of (c) obtained in step (f) to the bound $1^{st}$ domain sequence to obtain a bound ligation product comprising the $1^{st}$ and $2^{nd}$ domain sequence.

4. The method of claim 3, further comprising a step of removing unbound domain sequences after binding the first ligation product to the solid support, and optionally a further step of removing non-ligated domain sequences after ligating the second domain sequence to the bound first domain sequence.

5. The method of claim 1, further comprising a step of removing non-ligated domain sequences after each ligation step performed in steps (j) and (k).

6. The method of claim 1, wherein the domain sequences of (a) are cloned into a vector prior to amplification.

7. The method of claim 1, wherein the step of releasing the ligation product or ligation products from the solid support is carried out using a restriction enzyme targeting the restriction site at that end of the $1^{st}$ domain, which is carrying the tag labelling.

8. The method of claim 1, wherein in case of repeated ligation steps optionally after any repeated ligation step part of the obtained bound ligation product is separated from the method prior to performing a subsequent ligation step.

9. The method of claim 1, wherein the solid support is a particle, a surface of a device, a foil or a fleece.

10. The method of claim 9, wherein the particle is a silica bead or an organic polymer bead being magnetic.

11. The method of claim 1, wherein step (a) further includes providing one or more DNA sequences each encoding at least one CBD and at least one EAD.

* * * * *

UNITED STATES PATENT AND TRADEMARK OFFICE
CERTIFICATE OF CORRECTION

PATENT NO. : 10,655,113 B2
APPLICATION NO. : 16/390576
DATED : May 19, 2020
INVENTOR(S) : Anna Scherzinger et al.

Page 1 of 1

It is certified that error appears in the above-identified patent and that said Letters Patent is hereby corrected as shown below:

In the Claims

In Claim 1, Column 79, Line 14, delete "optionally".

Signed and Sealed this
First Day of September, 2020

Andrei Iancu
*Director of the United States Patent and Trademark Office*